(12) United States Patent
Jacob

(10) Patent No.: US 9,012,411 B2
(45) Date of Patent: Apr. 21, 2015

(54) FORMULATIONS FROM DERIVATIVES OF CURCUMIN, PACLITAXEL, AND ASPIRIN

(75) Inventor: James N. Jacob, Saunderstown, RI (US)

(73) Assignee: Organomed Corporation, Coventry, RI (US)

( * ) Notice: Subject to any disclaimer, the term of this patent is extended or adjusted under 35 U.S.C. 154(b) by 58 days.

(21) Appl. No.: 13/537,814

(22) Filed: Jun. 29, 2012

(65) Prior Publication Data

US 2013/0029922 A1 Jan. 31, 2013

Related U.S. Application Data

(63) Continuation-in-part of application No. PCT/US2010/062481, filed on Dec. 30, 2010.

(60) Provisional application No. 61/282,211, filed on Dec. 31, 2009.

(51) Int. Cl.

| | |
|---|---|
| A61K 31/12 | (2006.01) |
| A61K 31/015 | (2006.01) |
| A61K 31/202 | (2006.01) |
| A61K 31/337 | (2006.01) |
| A61K 31/616 | (2006.01) |
| A61K 36/9066 | (2006.01) |
| A61K 31/7034 | (2006.01) |
| C07C 69/157 | (2006.01) |
| C07C 69/42 | (2006.01) |
| C07C 69/587 | (2006.01) |
| C07C 69/92 | (2006.01) |
| C07H 13/04 | (2006.01) |

(52) U.S. Cl.
CPC ............. *A61K 36/9066* (2013.01); *A61K 31/12* (2013.01); *A61K 31/337* (2013.01); *A61K 31/616* (2013.01); *A61K 31/7034* (2013.01); *C07C 69/157* (2013.01); *C07C 69/42* (2013.01); *C07C 69/587* (2013.01); *C07C 69/92* (2013.01); *C07H 13/04* (2013.01)

(58) Field of Classification Search
CPC ..... A61K 31/12; A61K 31/337; C07H 13/04; C07C 69/92; C07C 69/587; C07C 69/42
USPC ....................... 514/23, 159; 536/119; 560/194
See application file for complete search history.

(56) References Cited

U.S. PATENT DOCUMENTS

| | | | |
|---|---|---|---|
| 3,279,990 | A | 10/1966 | Rose et al. |
| 3,843,626 | A | 10/1974 | Sutton |
| 4,242,330 | A | 12/1980 | Hussain et al. |
| 4,906,471 | A | 3/1990 | Liu |
| 5,108,750 | A | 4/1992 | Liu |
| 5,700,784 | A | 12/1997 | Shinojima et al. |
| 6,218,367 | B1 * | 4/2001 | Jacob ............................. 514/25 |
| 6,979,470 | B2 | 12/2005 | Babish et al. |
| 7,205,011 | B2 | 4/2007 | Chen et al. |
| 7,682,636 | B2 | 3/2010 | Babish et al. |
| 7,736,679 | B2 | 6/2010 | Antony |
| 2003/0147979 | A1 | 8/2003 | Mae et al. |
| 2003/0153512 | A1 | 8/2003 | Hergenhahn et al. |
| 2005/0008682 | A1 | 1/2005 | Tramontana |
| 2005/0181036 | A1 | 8/2005 | Aggarwal et al. |
| 2005/0208157 | A1 | 9/2005 | Navarro et al. |
| 2005/0215487 | A1 * | 9/2005 | Holick et al. .................... 514/23 |
| 2005/0267221 | A1 | 12/2005 | Wellen |
| 2006/0067998 | A1 | 3/2006 | Kurzrock et al. |
| 2006/0210656 | A1 | 9/2006 | Aggarwal |
| 2006/0228403 | A1 | 10/2006 | Zimmerman |
| 2007/0060644 | A1 | 3/2007 | Vander Jagt et al. |
| 2007/0148263 | A1 | 6/2007 | Antony |
| 2008/0193573 | A1 | 8/2008 | Gow et al. |
| 2009/0104294 | A1 | 4/2009 | Wenk et al. |
| 2009/0131373 | A1 | 5/2009 | Giori et al. |
| 2009/0280199 | A1 | 11/2009 | Russell |
| 2009/0291102 | A1 | 11/2009 | Fortin |
| 2010/0048901 | A1 | 2/2010 | Takahashi et al. |
| 2010/0196496 | A1 | 8/2010 | Fortin |

FOREIGN PATENT DOCUMENTS

| | | | |
|---|---|---|---|
| CN | 1739509 | A | 3/2006 |
| DE | 10245988 | * | 1/2005 |
| KR | 20100060674 | A | 6/2010 |
| WO | 86/03206 | A1 | 6/1986 |
| WO | WO2006117077 | * | 11/2006 |
| WO | 2008/150899 | A1 | 12/2008 |

OTHER PUBLICATIONS

Sharma et al. Curcumin: The story so far. European Journal of Cancer 41:1955-1968, 2005.*

Cassileth, B. "Turmeric (*Curcuma longa, Curcuma domestica*)" Oncology, vol. 24 No. 6 http://www.cancernetwork.com/display/article/10165/1568482 (Accessed Oct. 26, 2010).

Gopalan, B. et al. "Supercritical Carbon Dioxide Extraction of Turmeric (*Curcuma longa*)" J. Agric. Food Chem. 2000, 48, pp. 2189-2192.

Kao, L. et al. "Supercritical $CO_2$ Extraction of Turmerones From Turmeric and High-Pressure Phase Equilibrium of $CO_2$ + turmerones" J. of Supercritical Fluids, 2007, 43, pp. 276-282.

Kunnumakkara, A. B. et al. "Curcumin Potentiates Antitumor Activity of Gemcitabine in an Orthotopic Model of Pancreatic Cancer Through Suppression of Proliferation, Angiogenesis, and Inhibition of Nuclear Factor-Kappab-Regulated Gene Products" Cancer Res., 2007, 67(8), pp. 3853-3861.

Saw, C. L. L. et al. "synergistic anti-Inflammatory Effects of Low Doses of Curcumin in Combination With Polyunsaturated Fatty Acids: Docosahexaenoic Acid or Eicosapentaenoic Acid" Biochemical Pharmacology, 2010, 79 (3), pp. 421-430.

(Continued)

*Primary Examiner* — Yong Chu
*Assistant Examiner* — Yih-Horng Shiao
(74) *Attorney, Agent, or Firm* — Nixon Peabody LLP

(57) ABSTRACT

The invention provides novel compounds and formulations of turmeric oil, fish oil, aspirin and anti-cancer drugs (paclitaxel) having anti-inflammatory, analgesic and/or anti-cancer activity.

17 Claims, 53 Drawing Sheets

(56) References Cited

OTHER PUBLICATIONS

Turmeric. http://www.hairdye.eu/turmeric_en.html (Accessed Oct. 26, 2010).

Jayaprakasha, G. K., et al., "Chemical composition of turmeric oil a byproduct from turmeric oleoresin industry and its inhibitory activity against different fungi" Z Naturforsch C, 2001, 01-02, vol. 56, No. 1-2, pp. 40-44.

Jeong, S. O., "dimethoxycurcumin, a synthetic curcumin analogue, induces heme oxygenase-1 expression through Nrf2 activiation in RAW264.7 macrophages" Journal of Clinical Biochemistry and Nutrition, Jan. 2009, vol. 44, No. 1, pp. 79-84.

Lin, L., et al., "Antitumor agents 250. design and synthesis of new curcumin analogues as potential anti-prostate cancer agents" Journal of Medicinal Chemistry, Jun. 29, 2006, vol. 49, No. 13, pp. 3963-3972.

\* cited by examiner

Di(acetylsalicyloyl)-curcumin
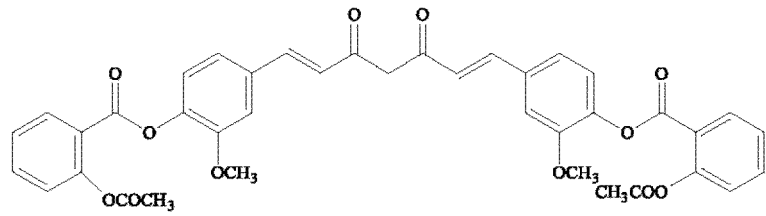
Monoacetylsalicyloyl-curcumin
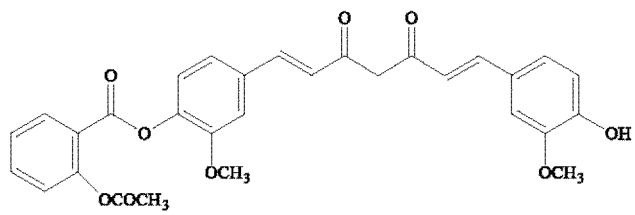
Diacetylcurcumin
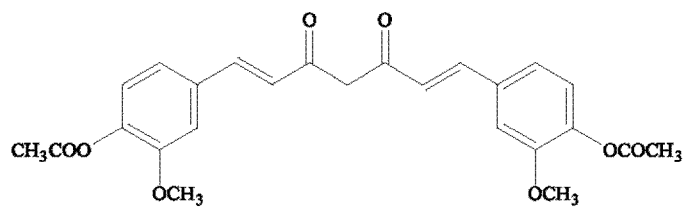
Diglutaroyl curcumin
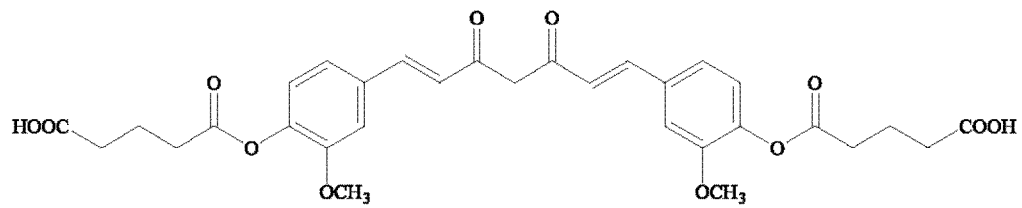
Monoglutaroyl curcumin
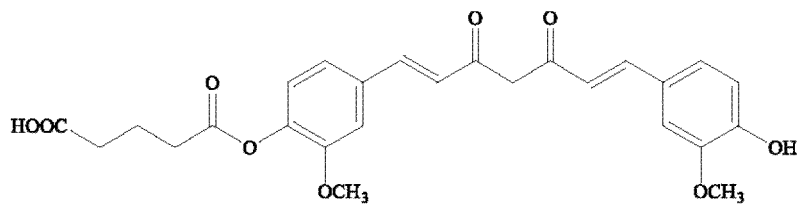
*FIG. 1A*

Di-glucose-glutaroyl-curcumin
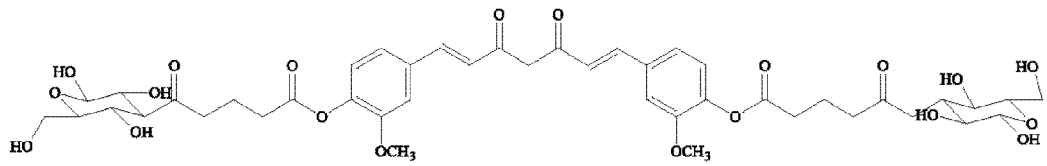
Mono-glucose-glutaroyl-curcumin
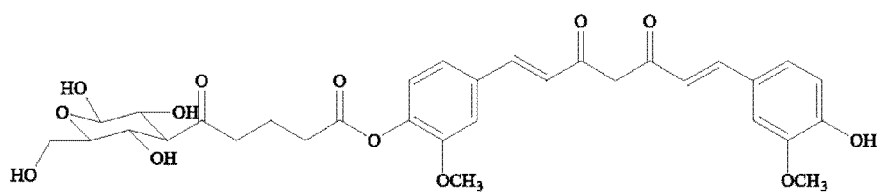
Monolinoleol-curcumin
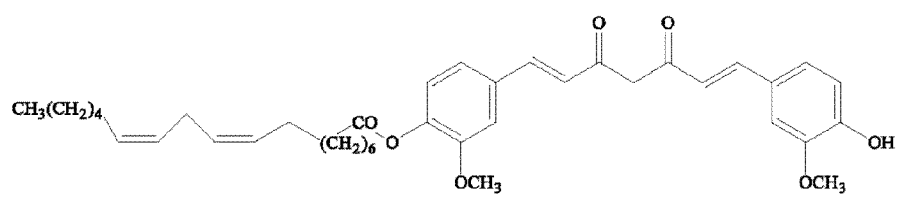
Di-linoleoyl-curcumin
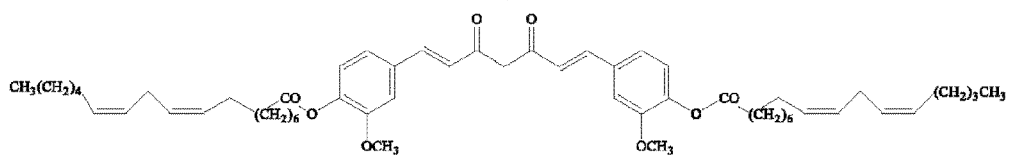
Peptide-curcumin conjugate
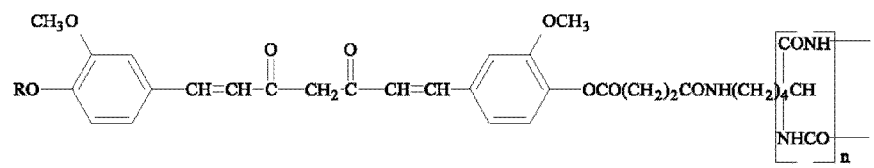
R = H or succinoyl or another group. Curcumin attached to a lysine containing peptide.
*FIG. 1B*

*p<0.05 as compared to group 1 (Normal saline)
# p<0.05 as compared to group 7 (Aspirin)

FORMULATIONS FROM DERIVATIVES OF CURCUMIN, PACLITAXEL, AND ASPIRIN

CROSS REFERENCE TO RELATED APPLICATIONS

This application claims benefit under 35 U.S.C. §120 and is a Continuation-in-Part of International PCT Application No. PCT/US2010/062481, filed Dec. 30, 2010, which claims benefit under 35 U.S.C. §119(e) to U.S. Provisional Application Ser. No. 61/282,211, filed Dec. 31, 2009. Contents of both applications are incorporated by reference herein in their entireties.

FIELD OF THE INVENTION

The invention relates to compositions and methods for treatment of inflammatory diseases and cancer.

BACKGROUND OF THE INVENTION

Turmeric is an Asian spice and a traditional remedy since 600 BC. The turmeric plant (*Curcuma longa*) is a member of the ginger family (Zingiberaceae). The rhizome (underground stem) is used to obtain turmeric powder or ground turmeric. Turmeric was used for many centuries in Ayurveda, an Indian traditional medical system, for treating and preventing a number of illnesses. Modern scientific studies of the powerful biologically active compounds contained in the natural product, turmeric has been shown to have many health benefits including strong anti-cancer properties. It decreases symptoms of skin cancers and reduces the incidence of chemically caused breast cancer in animals.

Curcumin is an active ingredient derived from turmeric and it imparts the yellow color in turmeric. It has several biological activities with beneficial effects on cancer prevention and cure, and on a variety of other diseases such as arthritis, wound healing and Alzheimer's disease. In addition to curcumin there are several other biologically active compounds in turmeric which have not received much attention but have strong biological activity. Curcumin has been shown to be effective in three ways in attacking cancer. It suppresses transformation, proliferation, and metastasis of tumors. Curcumin has been shown to have protective and therapeutic effects against cancers of the blood, skin, pancreas, lung, oral cavity, and intestinal tract. Curcumin is shown to be multi-targeted since it modulates multiple cell signaling pathways. Curcumin asserts its anti-tumor activity by altering the dysregulated cell cycle via (a) cyclin-dependent, (b) p53-dependent and (c) p53-independent pathways.

However, curcumin is poorly bio-available following oral administration. The results suggest that doses of curcumin required to furnish hepatic levels sufficient to exert pharmacological activity are probably not feasible in humans and further research on both the biological activity and bioavailability of dietary polyphenols is needed to properly assess their usefulness for the prevention and treatment of disease.

SUMMARY OF THE INVENTION

The inventor has discovered a series of novel compounds and formulations having anti-inflammatory, analgesic and/or anti-cancer activity. Accordingly, in one aspect, the invention provides a turmeric oil extract obtained by high vacuum distillation of turmeric oil and collecting a distillate at 70-100° C., at 105 to 118° C. or at 100-130° C.

In another aspect, the invention provides curcumin derivatives having the structure shown in formula (I):

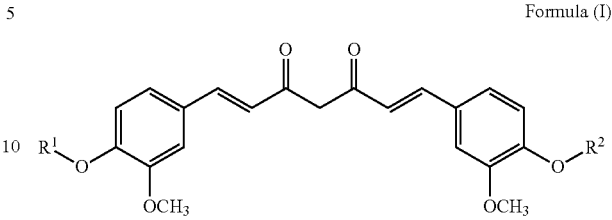

Formula (I)

wherein:
$R^1$ and $R^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)$R^3$, —C(O)O$R^3$, or —C(O)N$R^3R^3$, provided that at least one of $R^1$ and $R^2$ is not H, or both of $R^1$ and $R^2$ are not octyl or hexadecyl, or one of $R^1$ or $R^2$ is not H and the other is not octyl or hexadecyl;

$R^3$ is independently for each occurrence H, optionally substituted alkyl, optionally substituted alkenyl, optionally substituted alkynyl, optionally substituted cyclyl, optionally substituted heterocyclyl, optionally substituted aryl, optionally substituted heteroaryl; and analogs, derivatives, isomers, prodrugs, and pharmaceutically acceptable salts thereof.

The inventor has also discovered that carbohydrate-aspirin conjugates unexpectedly have enhanced anti-inflammatory and/or anti-cancer activity relative to unconjugated aspirin. Thus, the invention provides compounds of formula (II) as anti-inflammatory and anti-cancer agents. A compound of formula (II) is:

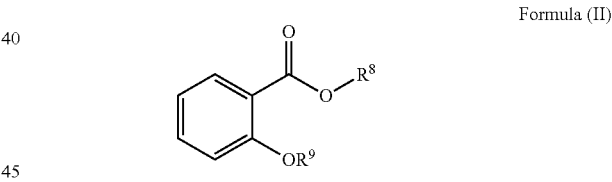

Formula (II)

wherein:
$R^8$ is a carbohydrate;
$R^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof.

In yet another aspect, the invention provides a composition comprising turmeric oil or a turmeric oil extract and at least one compound selected from the group consisting of anti-cancer agents, anti-inflammatory agents, compounds of formula (I), compounds of formula (II), fish oil, fish oil extract, and any combinations thereof.

The invention also provides a composition comprising curcumin and/or a curcumin derivative of formula (I) and at least one compound selected from the group consisting of anti-cancer agents, anti-inflammatory agents, compounds of formula (II), fish oil, fish oil extract, and any combinations thereof.

The invention further provides a method for treating a subject for inflammation, or a disease or condition associated with inflammation, the method comprising administering a therapeutically effective amount of a turmeric oil extract described herein, a compound described herein, a composition described herein, and any combinations thereof to a subject in need thereof.

The invention also provides a method of treating a subject for cancer, the method comprising administering a therapeutically effective amount of a turmeric oil extract described herein, a compound described herein, a composition described herein, and any combinations thereof to a subject in need thereof.

BRIEF DESCRIPTION OF THE DRAWINGS

FIGS. 1A-1B depict exemplary curcumin derivatives of formula (I).

FIG. 2A shows the full spectra, and FIG. 2B shows the peaks from 5.2 ppm to 6.4 ppm.

FIG. 3A shows the full spectra; FIG. 3B shows peaks from 0 ppm to 2.6 ppm; FIG. 3C shows the peaks from 4.7 ppm to 6.3 ppm.

In FIG. 17A, concentration is micromolar (μM), and in FIG. 17B concentration is molar (M).

In FIG. 18A, concentration is micromolar (μM), and in FIG. 18B concentration is molar (M).

In FIG. 19A, concentration is micromolar (μM), and in FIG. 19B concentration is molar (M).

In FIGS. 22A and 22B concentration of compounds is in molar (M).

In FIGS. 23A and 23B concentration of compounds is in molar (M).

In FIGS. 24A and 24B concentration is in molar (M) with respect to paclitaxel.

In FIGS. 25A and 25B concentration is in molar (M).

DETAILED DESCRIPTION OF THE INVENTION

Figure 2A:
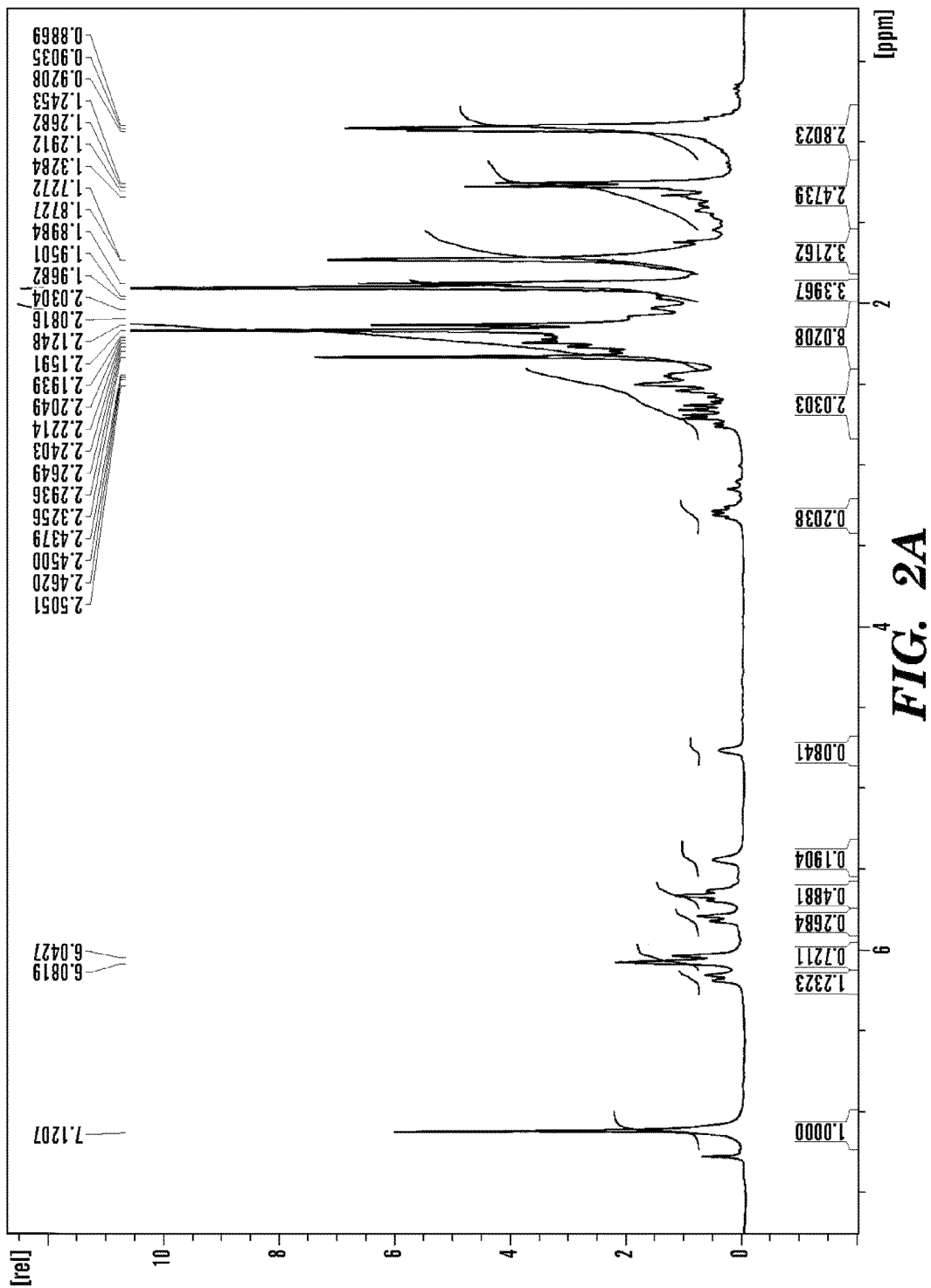
FIGS. 2A and 2B show the NMR spectra of turmeric oil extract fraction NJ-78-12.
Figure 2B:
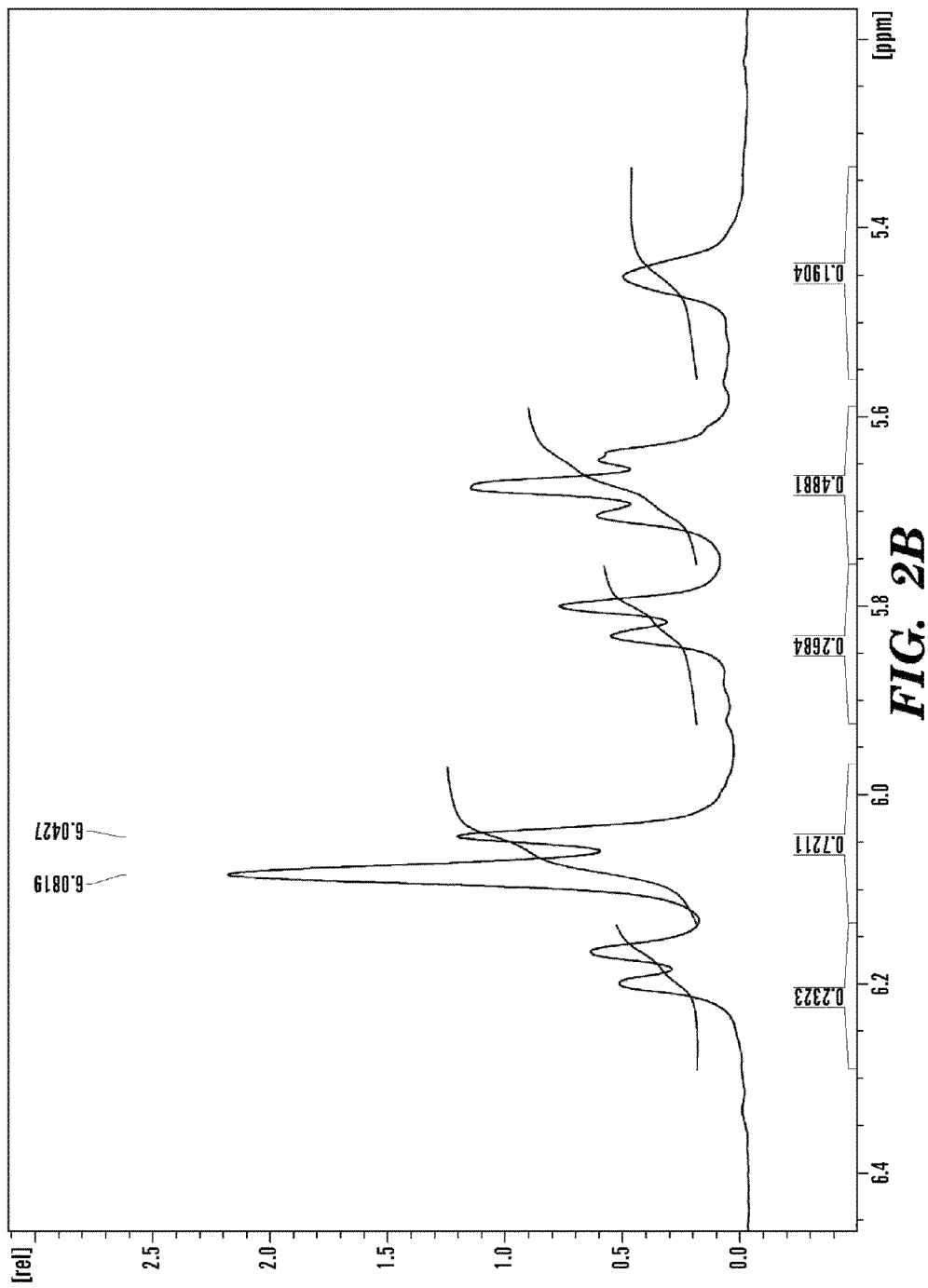
Figure 3A:
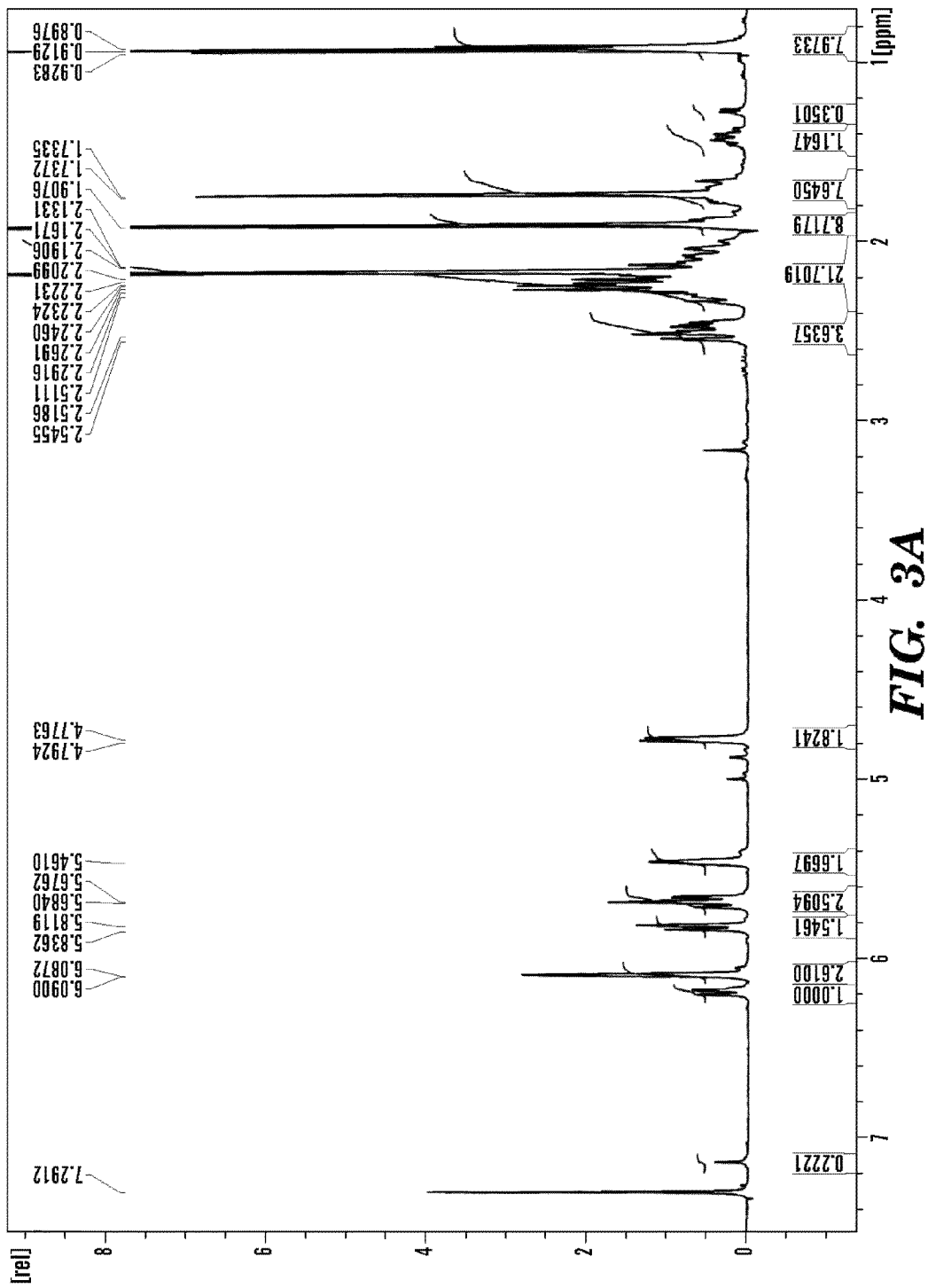
FIGS. 3A-3C show the NMR spectra of turmeric oil extract fraction MT-133-3.
Figure 3B:
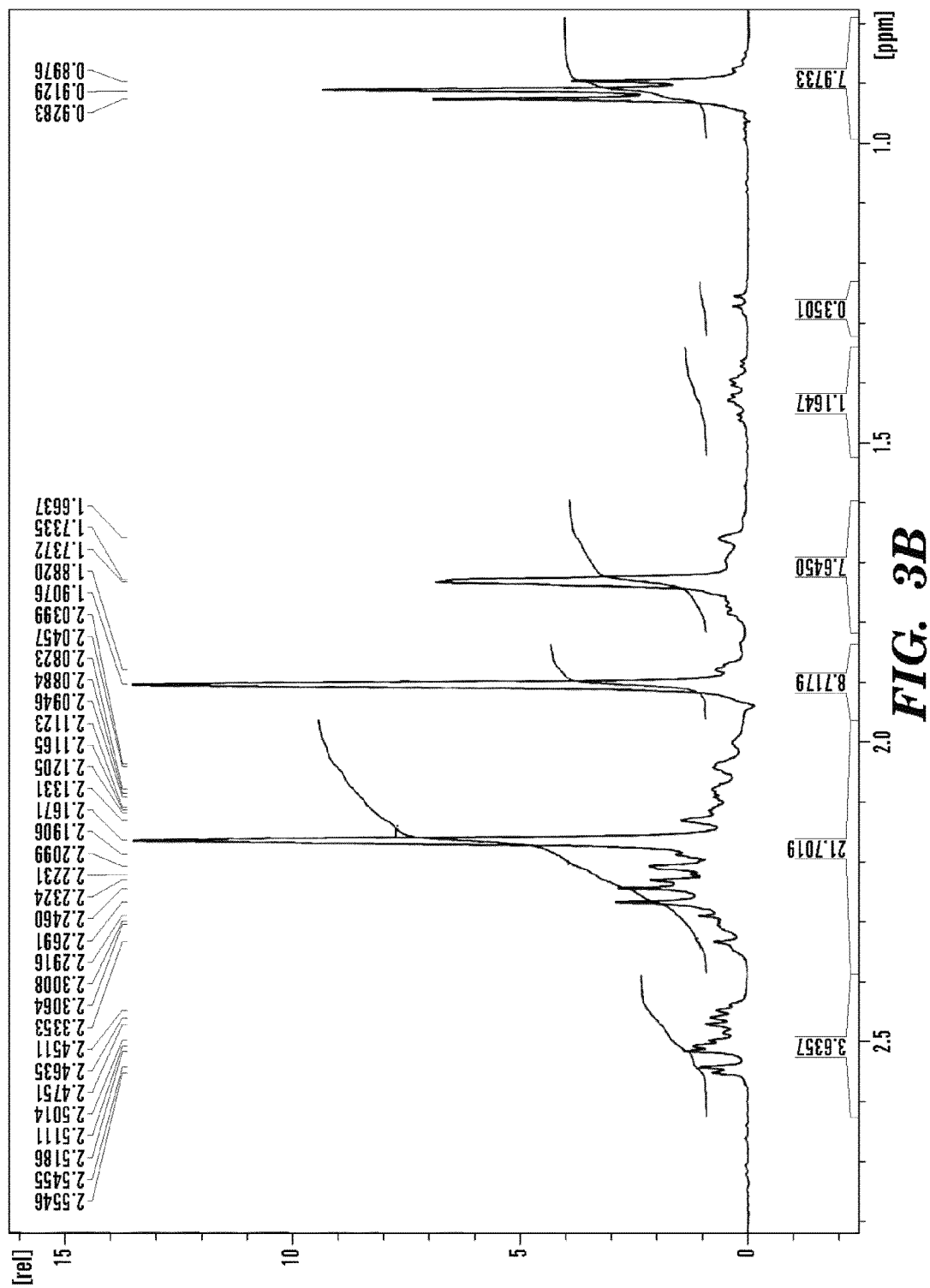
Figure 3C:
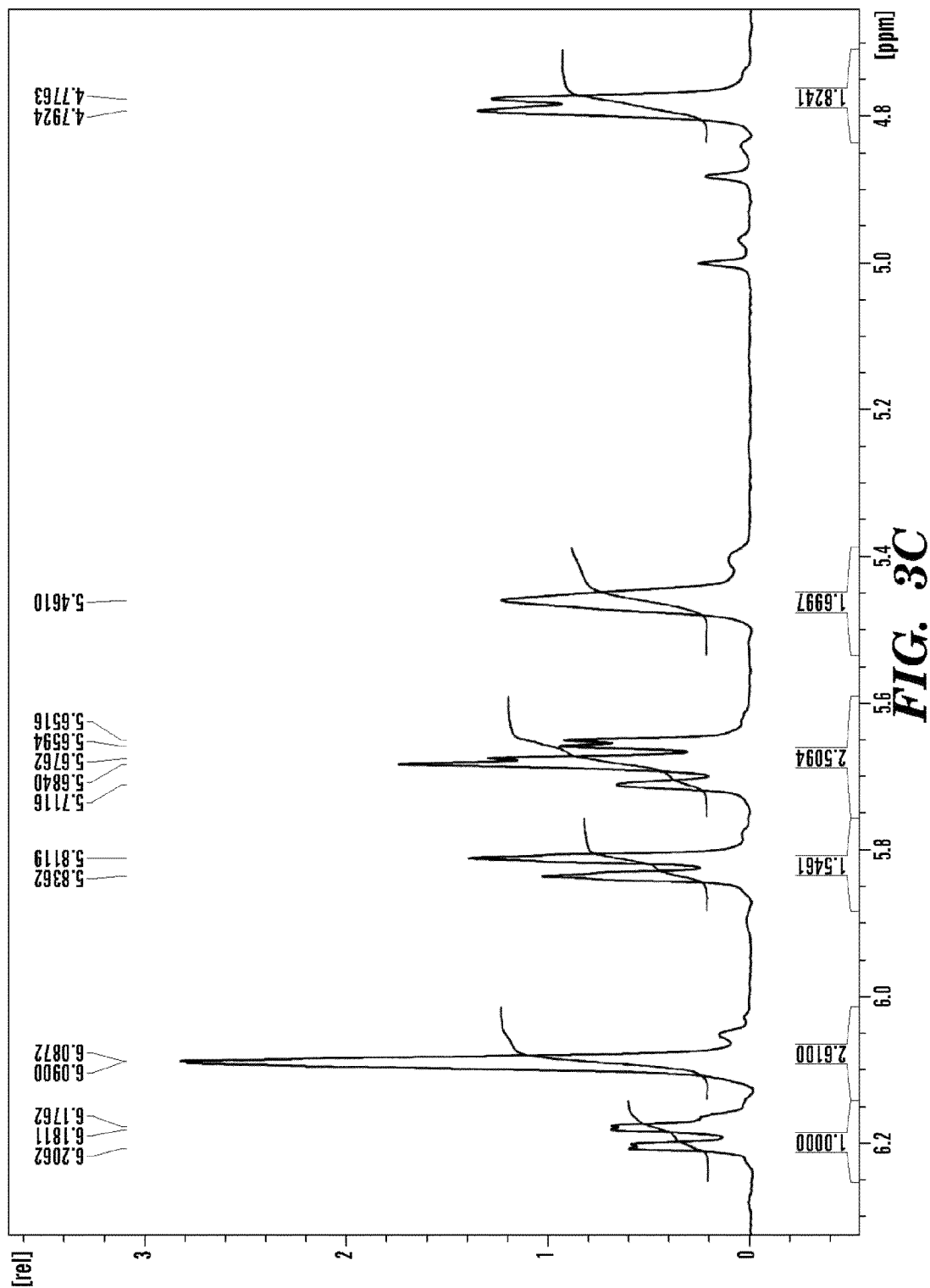
Figure 4A:
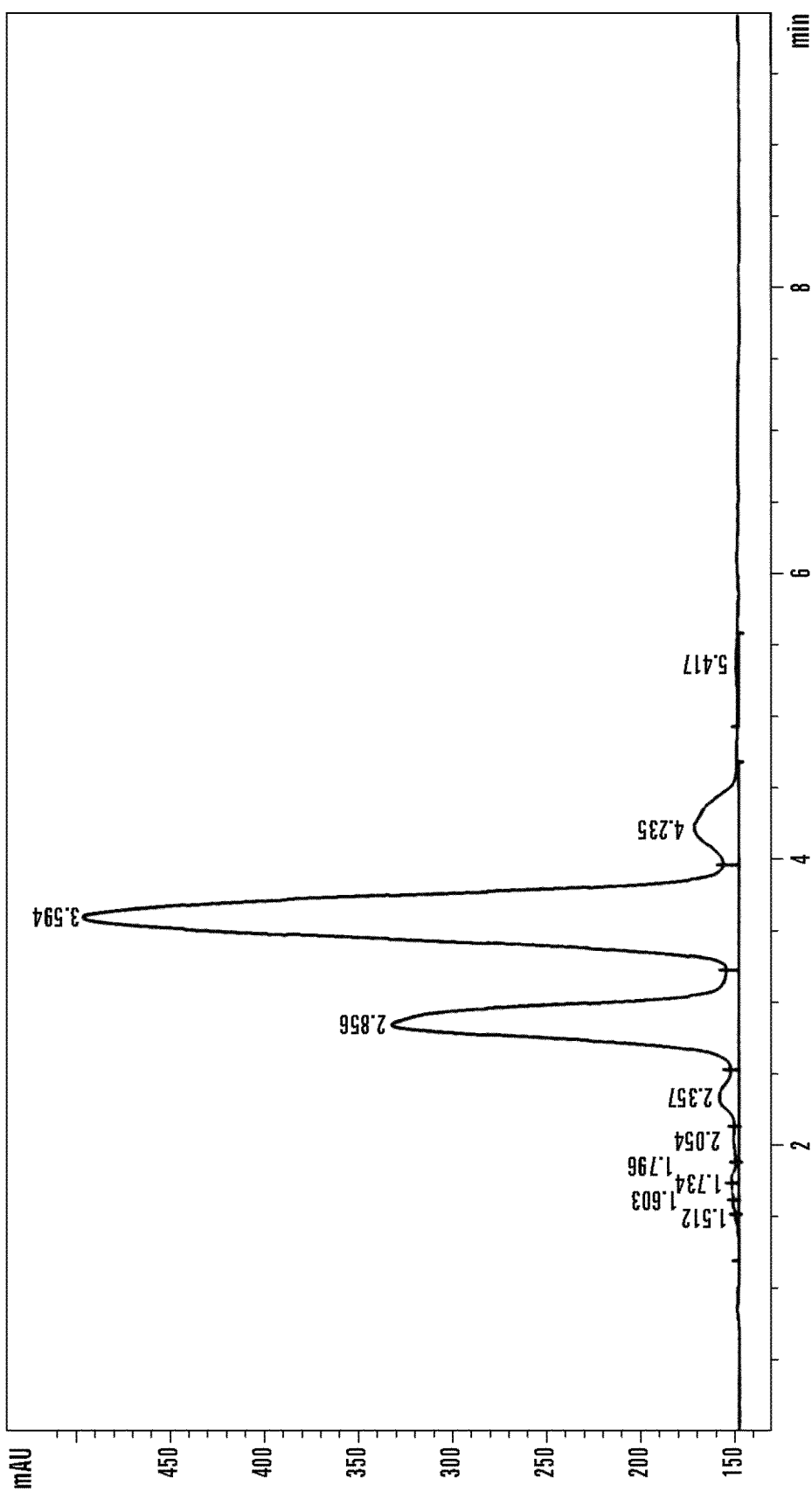
FIGS. 4A and 4B are HPLC spectra of NJ-78-12 (FIG. 4A) and MT-133-3 (FIG. 4B).
Figure 4B:
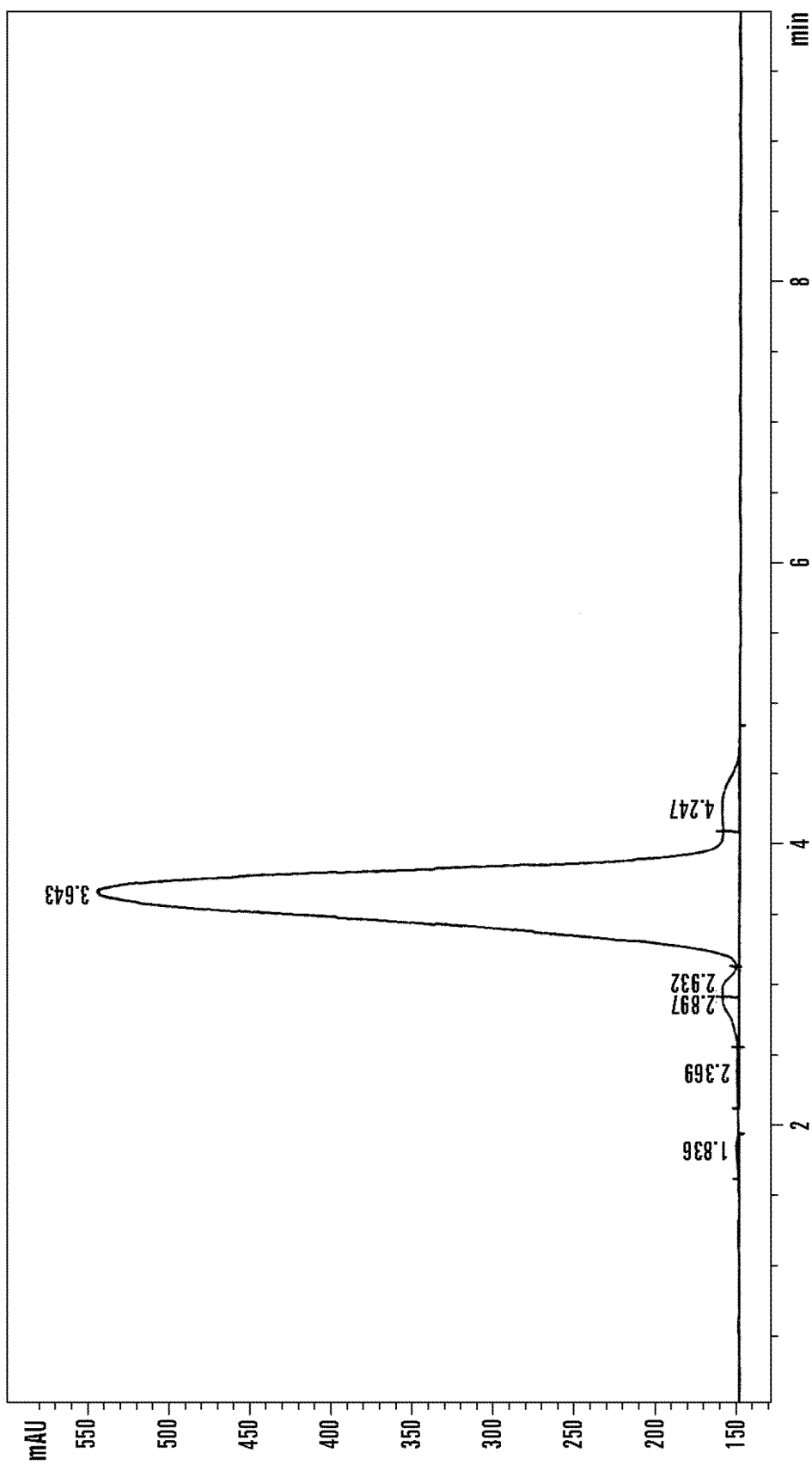

The inventor has discovered a series of novel compounds and formulations having anti-inflammatory, analgesic and/or anti-cancer activity.

Turmeric Oil Extract

In one aspect, described herein is a turmeric oil extract obtained by high vacuum distillation of turmeric oil and collecting a distillate at 70-100° C., at 105 to 118° C. or at 100-130° C. As used herein, the term "high vacuum" refers to pressure less than 250 torr of base vacuum. In some embodiments, distillation is at a pressure less than about 200 torr, less than about 150 torr, less than about 100 torr, less than about 50 torr, less than about 25 torr, less than about 10 torr, less than about 0.1 torr, or less than about 0.01 torr. In one embodiment, distillation is at pressure in the range of 0.1 torr to 100 torr.

In some embodiments the extract is obtained by a method comprising the steps of: (i) extracting a turmeric powder with hexane; (ii) distilling the extract of (i) to obtain a distillate at 115-135° C. under high vacuum; (iii) distilling the distillate of (ii) to obtain a distillate at 95-112° C. under high vacuum; (iv) distilling the distillate of (iii) to obtain a distillate at 100-110° C. under high vacuum; and (v) distilling the distillate of (iv) to obtain the extract as a distillate at 120-123° C. under high vacuum. This extract is also referred to as NJ-78-12 herein. It is to be understood that a distillate of (ii), (iii), or (iv) is also a turmeric oil extract of the invention.

In some embodiments the extract is obtained by a method comprising the steps of: (i) extracting a turmeric powder with hexane; (ii) distilling the extract of (i) to obtain a distillate at 115-135° C. under high vacuum; (iii) distilling the distillate of (ii) to obtain a distillate at 95-112° C. under high vacuum; (iv) distilling the distillate of (iii) to obtain a distillate at 100-110° C. under high vacuum; (v) distilling the distillate of (iv) to obtain a distillate at 100-120° C. and at 124° C. under high vacuum; (vi) combining the distillates obtained in (v) and obtaining the extract by eluting the combined distillates from a column using one volume of hexane, one volume 0.5% of ethyl acetate/hexane, and half volume 1% ethyl acetate/Hexane. This fraction is also referred to as MT-133-3 herein.

Further fractions from the column can also be obtained as follows: after elution of fraction MT-133-3, eluting with half volume of 1% ethyl acetate/Hexane to obtain the fraction referred to as MT-133-4; followed by two volumes of 2% ethyl acetate/Hexane to obtain fractions referred to as MT-133-5, MT-133-6 and MT-133-7; followed by one volume of 5% ethyl acetate/hexane to obtain fractions MT-133-8 and MT-133-9; followed by ¼ volume of methanol to obtain fraction MT-133-10. It is to be understood that a distillate of (ii), (iii), (iv) or (v) is also a turmeric oil extract of the invention.

Furthermore, any of the fractions obtained from the column chromatography purification, either alone or in a mixture with one or more of the other fractions is also considered a turmeric oil extract of the invention.

In some embodiments the extract is obtained by a method comprising the steps of: (i) extracting a turmeric powder with hexane; (ii) distilling the extract of (i) to obtain a first distillate at below 108° C. under vacuum, a second distillate at 108° C.-122° C. under vacuum, and a third distillate at 122° C.-143° C. under vacuum; (iii) purifying the second distillate from (ii) using flash column chromatography with hexane-ethylacetate. This extract is also referred to as BR-110-6 herein.

In some embodiments the extract is obtained by a method comprising the steps of: (i) extracting a turmeric powder with hexane; (ii) distilling the extract of (i) to obtain a first distillate at below 108° C. under vacuum, a second distillate at 108° C.-122° C. under vacuum, and a third distillate at 122° C.-143° C. under vacuum; (iii) purifying the second distillate from (ii) using flash column chromatography with hexane-ethylacetate; (iv) combining the purified product from (iii) (e.g., BR-110-6) with the third distillate of (ii); and (v) distilling the combined mixture of (iv) to obtain a distillate at 118° C.-137° C. under vacuum. This distillate is also referred to as BR-132-4 herein and corresponds to fractions MT-133-4 to MT-133-9 described herein.

In some embodiments the extract is obtained by a method comprising the steps of: (i) extracting a turmeric powder with hexane; (ii) distilling the extract of (i) to obtain a first distillate at below 108° C. under vacuum, a second distillate at 108° C.-122° C. under vacuum, and a third distillate at 122° C.-143° C. under vacuum; (iii) purifying the second distillate from (ii) using flash column chromatography with hexane-ethylacetate; (iv) combining the purified product from (iii) (e.g., BR-110-6) with the third distillate of (ii); (v) distilling the combined mixture of (iv) to obtain a distillate at 118° C.-137° C. under vacuum. This distillate is also referred to as BR-132-4 herein and corresponds to fractions MT-133-4 to MT-133-9 described herein; and (vi) purifying the distillate of (v) to obtain two fractions. These purified fractions are also referred to as NJ-106-1 and NJ-106-2 herein.

In some embodiments the extract is obtained by a method comprising the steps of: (i) extracting a turmeric powder with hexane; (ii) distilling the extract of (i) to obtain a distillate at 115° C.-135° C.; (iii) distilling the distillate of (ii) to obtain a first distillate at 95° C.-108° C. under vacuum and a second distillate at 108° C.-112° C.; (iv) distilling the second distillate from (iii) to obtain a first distillate at 100° C.-120° C., a second distillate at 120° C.-123° C., and a third distillate at 124° C. under high vacuum. These turmeric oil extracts are also referred to as NJ-78-11 (first distillate), NJ-78-12 (second distillate), and NJ-78-13 (third distillate) herein.

In some embodiments, the method of obtaining the turmeric oil extract further comprises the step of purifying the extract obtained by the above methods. The skilled artisan is well aware of methods of purifying compounds. Such methods include, but are not limited to, column chromatography, high pressure liquid chromatography, size-exclusion chromatography, crystallization, distillation, filtration, and the like.

The turmeric oil fraction of the invention may contain one or more sesquiterpenes including, but not limited to, Ar-turmerone α-turmerone, and β-turmerone.

In some embodiments, the turmeric oil fraction comprises a mixture of compounds with at least one compound comprising at least 50%, at least 60%, at least 70%, at least 75%, at least 80%, at least 85%, at least 90%, or at least 95% of the mixture of the compounds. The amount of the compounds in the turmeric oil fraction can be determined using any techniques available to the skilled artisan, including, but not limited to, high performance liquid chromatography (HPLC), liquid chromatography, size exclusion chromatography, thin layer chromatography (TLC), NMR, and IR.

In some embodiments, the turmeric oil extract is at least 65%, at least 70%, at least 75%, at least 80%, at least 85%, at least 90%, or at least 95% pure as determined by NMR, HPLC, LC and/or TLC. In some embodiments, the purity of the turmeric oil extract is determined by HPLC with the following conditions: X-Terra C-18 column (4.6×150 mm, 5 μm), Acetonitrile/water (85/15), 1 mL/min, UV detection at 253 nm.

The turmeric oil extract of the invention can be identified based on its elemental composition. By elemental composition is meant the different types of atoms present in a compound. Thus, the turmeric oil extract of the invention can be identified by the amount and/or ratio of the different atoms present in the extract. Methods of determining element compositions are well known to the skilled artisan and many commercial entities provide services to determine the elemental compositions. In some embodiments, the turmeric oil extract comprises from about 70 to about 75% carbon and from about 5 to about 10% hydrogen. In some further embodiments of this, the turmeric oil extract comprises about 73% carbon and 8% hydrogen. In some embodiments, the turmeric oil extract comprises about 73.8% carbon and about 8.7% hydrogen.

Alternatively, or in addition, the turmeric oil extract of the invention can be identified based on NMR spectra. Accordingly, in some embodiments, at least one compound in the turmeric oil extract has an NMR spectra as shown in FIG. 2, 3, 32-38 or 44. In some embodiments, the turmeric oil extract comprises at least two compounds having an NMR spectra shown in FIG. 2, 3, 32-38, or 44. In one embodiment, the turmeric oil extract comprises a compound having an NMR spectra shown in FIG. 32 and a compound having an NMR spectra shown in FIG. 33. In one embodiment, the turmeric oil extract comprises a compound having an NMR spectra shown in FIG. 44A and a compound having an NMR spectra shown in FIG. 44B. Methods of predicting NMR spectra for a compound of known structure are known to the skilled artisan. For example, commercially available computer program ACD/NMR Predictors from Advanced Chemistry Development, Inc. (Toronto, Ontario, Canada) can predict the following nuclei—$^1$H, $^{13}$C, $^{15}$N, $^{19}$F, and $^{31}$P—for 1D spectra, and $^1$H and $^{13}$C (and $^{15}$N) for 2D spectrum.

The turmeric oil extract of the invention can also be identified based on GC mass spectra of the extract. Accordingly, in some embodiments, at least one compound in the turmeric oil extract has an GC mass spectrum as shown in FIGS. 41-43 and 45-48. It is to be understood, that in some embodiments, at least one compound in the turmeric oil extract has a fragmentation pattern as shown in FIG. 41-43 or 45-48. In some embodiments, the turmeric oil extract has an $R_f$ of 0.42 by TLC (ethyl acetate/hexane 15/85).

The turmeric oil extracts described herein have anti-inflammatory activity and/or anti-cancer activity. Furthermore, the turmeric oil extracts are also analgesic. Moreover, as discussed herein, the turmeric oil extracts show synergistic anti-inflammatory activity and/or analgesic activity with anti-inflammatory agents. The turmeric oil extracts described herein also enhance the anti-cancer activity of anti-cancer agents and show a synergistic effect with anti-cancer agents. In some embodiments, the turmeric oil fraction has anti-cancer activity pancreatic, breast or prostate cancer.

In some embodiments, the turmeric oil fraction comprises a mixture of β-turmerone/curlone, α-turmerone, and ar-turmerone.

In some embodiments, the turmeric oil fraction comprises at least 35% β-turmerone/curlone. In some embodiments, the turmeric oil fraction comprises from about 40% to about 65% (e.g., about 40, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%) β-turmerone/curlone.

In some embodiments, the turmeric oil fraction comprises at least 20% α-turmerone. In some embodiments, the turmeric oil fraction comprises from about 25% to about 50% (e.g., about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%) α-turmerone.

In some embodiments, the turmeric oil fraction comprises at least 1% ar-turmerone. In some embodiments, the turmeric oil fraction comprises from about 1% to about 15% (e.g., about 1%, about 2%, about 3%, about 4%, about 5%, about 6%, about 7%, about 8%, about 9%, about 10%, about 11%, about 12%, about 13%, about 14%, or about 15%) ar-turmerone.

In some embodiments, the turmeric oil fraction comprises from about 40% to about 65% β-turmerone/curlone, from about 25% to about 50% α-turmerone, and from about 1% to about 15% ar-turmerone.

In one embodiment, the turmeric oil fraction comprises about 53% β-turmerone/curlone, about 36% α-turmerone, and about 4% ar-turmerone.

In some embodiments, the turmeric oil fraction comprises a mixture of β-sesquiphellandrene, 7-epi-zingiberene, and ar-curcumene.

In some embodiments, the turmeric oil fraction comprises at least 35% β-sesquiphellandrene. In some embodiments, the turmeric oil fraction comprises from about 40% to about 60% (e.g., about 40, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%) β-sesquiphellandrene.

In some embodiments, the turmeric oil fraction comprises at least 15% 7-epi-zingiberene. In some embodiments, the turmeric oil fraction comprises from about 20% to about 40% (e.g., 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, or about 40%) 7-epi-zingiberene.

In some embodiments, the turmeric oil fraction comprises at least 5% ar-curcumene. In some embodiments, the turmeric oil fraction comprises from about 10% to about 30% (e.g. 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about or about 30%) ar-curcumene.

In some embodiments, the turmeric oil fraction comprises from about 40% to about 60% β-sesquiphellandrene, from about 20% to about 40% 7-epi-zingiberene, and from about 10% to about 30% ar-curcumene.

In one embodiment, the turmeric oil fraction comprises about 50% β-sesquiphellandrene, about 31% 7-epi-zingiberene, and about 19% ar-curcumene.

In some embodiments, the turmeric oil fraction comprises from about 40% to about 65% ar-turmerone, from about 25% to about 50% α-turmerone, and from about 5% to about 20% β-turmerone.

In one embodiment, the turmeric oil fraction comprises about 53% ar-turmerone/curlone, about 36% α-turmerone, and about 9% β-turmerone.

In some embodiments, the turmeric oil fraction comprises from about 55% to about 80% α-turmerone, from about 10% to about 30% β-turmerone, and from about 0.5% to about 5% ar-turmerone.

In one embodiment, the turmeric oil fraction comprises about 78% α-turmerone, about 20% 3-turmerone, and about 2% ar-turmerone.

It is to be understood that amounts of the various components in the turmeric oil fractions can be based on moles or weights.

Curcumin Derivatives

In another aspect, the invention provides a curcumin derivative having the structure shown in formula (I):

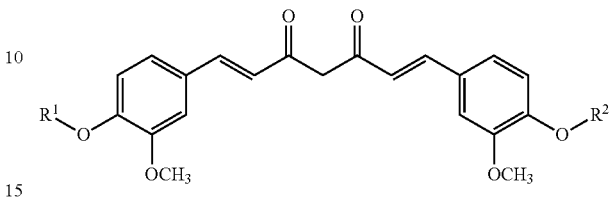

Formula (I)

wherein: $R^1$ and $R^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)$R^3$, —C(O)O$R^3$, or —C(O)N$R^3R^3$, provided that at least one of $R^1$ and $R^2$ is not H, or provided that both of $R^1$ and $R^2$ are not octyl or hexadecyl, or provided that one of $R^1$ or $R^2$ is not H and the other is not octyl or hexadecyl; $R^3$ is independently for each occurrence H, optionally substituted alkyl, optionally substituted alkenyl, optionally substituted alkynyl, optionally substituted cyclyl, optionally substituted heterocyclyl, optionally substituted aryl, optionally substituted heteroaryl; and analogs, derivatives, isomers, prodrugs, and pharmaceutically acceptable salts thereof.

One of skill in the art is well aware that curcumin can exist in at least two tautomeric forms, keto and enol. Without wishing to be bound by theory, the enol form is more energetically stable in the solid phase and in solution. Accordingly, while curcumin derivatives of formula (I) are shown in the keto form herein, the curcumin derivatives of formula (I) can exist in either the keto or the enol tautomer.

In some embodiment, $R^1$ and $R^2$ are the same.

In some embodiments, one of $R^1$ and $R^2$ is H.

In some embodiments, at least one of $R^1$ and $R^2$ is selected from the group consisting of acetyl, myristoleoyl, palmitoleoyl, sapienoyl, oleoyl, linoleoyl, α-linoleoyl, α-linolenoyl, γ-linolenoyl, arcchidionoyl, eicosapentaenoyl, erucoyl, docosahexaenoyl, lauroyl, myrsitoyl, palmitoyl, stearoyl, arachidoyl, behenoyl, lignoceroyl, certoyl and any combinations thereof.

In some embodiments, at least one of $R^1$ and $R^2$ is —C(O)$R^3$, —C(O)O$R^3$, or —C(O)N$R^3R^3$.

In some embodiments, $R^3$ is an optionally substituted aryl. The optionally substituted aryl can be substituted at the 2-, 3-, 4-, or 5-position or any combinations of these positions. One preferred optionally substituted aryl is a 2-substituted phenyl.

In some embodiments, at least one of $R^1$ and $R^2$ is —C(O)$R^3$ and $R^3$ is an optionally substituted aryl. Accordingly, at least one of $R^1$ and $R^2$ can be

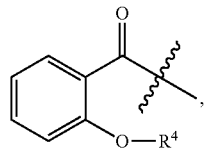

wherein $R^4$ is H, optionally substituted alkyl, optionally substituted alkenyl, optionally substituted alkynyl, or optionally substituted acyl. In some embodiments of this, $R^4$ is H or acetyl, i.e. $R^1$ and/or $R^2$ can be

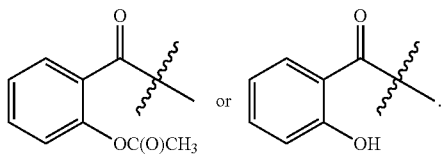

In some embodiments, at least one of $R^1$ and $R^2$ is —C(O)$R^3$; and $R^3$ is an alkenyl comprising 1, 2, 3, 4, 5 or 6 double bonds. When $R^3$ is an alkenyl, it can also comprise 1, 2, 3 or 4 triple bonds in addition to the double bonds.

In some embodiments, at least one of $R^1$ and $R^2$ is —C(O)$R^3$ and $R^3$ is an alkynyl comprising 1, 2, 3, 4, 5 or 6 triple bonds.

In some embodiments, at least one of $R^1$ and $R^2$ is -linker-$R^5$, wherein $R^5$ is a carbohydrate, a peptide, and analogs and derivatives thereof.

As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylherероaryl, where one or more methylenes can be interrupted or terminated by O, S, S(O), $SO_2$, $N(R^{11})_2$, C(O), cleavable linking group, substituted or unsubstituted aryl, substituted or unsubstituted heteroaryl, substituted or unsubstituted heterocyclic; where $R^{11}$ is hydrogen, acyl, aliphatic or substituted aliphatic.

In some embodiments, the linker is —C(O)$(CH_2)_m$C(O)O—, wherein m is an integer from 1 to 10. Preferably m is 1, 2, 3, 4, or 5. Accordingly, at least one of $R^1$ and $R^2$ can be —C(O)$(CH_2)_5$C(O)O$R^5$.

As used herein, the term "carbohydrate" includes, but is not limited to, compounds that contain oxygen, hydrogen and carbon atoms, typically $(C.H_2.O)n$ wherein n=3. Carbohydrates include, but are not limited to, compounds such as monosaccharides, oligosaccharides, polysaccharides, glycoproteins, glycolipids and the like. The hydroxyl and amino groups of the monosaccharide can be present as free or as protected groups. Preferred protecting groups include acetonide, t-butoxy carbonyl groups, etc. The monosaccharide can be of L or D configuration. A cyclic monosaccharide may contain a 5 or 6 membered ring in the α or β configuration. Exemplary monosaccharides include, but are not limited to, glucose, glyceraldehydes, erythrose, threose, ribulose, xylulose, ribose, arabinose, deoxyribose, xylose, lyxose, psicose, fructose, sorbose, tagatose, allose, altrose, mannose, gulose, idose, galactose, talose, fucose, fuculose, rhamnose, sedoheptulose, octose, nonose (Neuraminic acid), and the like.

While a monosaccharide can be linked at any carbon, it is preferred that a hexose is linked at the C4 position. Accordingly, in some embodiments, at least one of $R^1$ and $R^2$ is

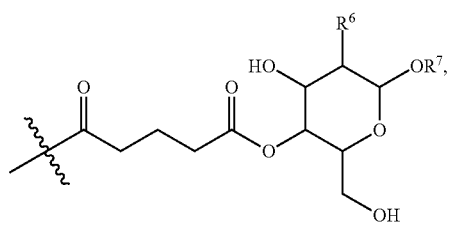

wherein $R^6$ is OH, amino, mono($C_1$-$C_6$alkyl)amino, di($C_1$-$C_6$alkyl)amino, $C_1$-$C_6$alkyl, cyclyl, or alkoxy; and $R^7$ is a H, alkyl, cyclyl, heterocyclyl, aryl, heteroaryl, carbohydrate, or a peptide. It is to be understood that the pyranose moiety can have the α or β configuration at C1.

In some embodiments, $R^6$ is OH.

In some embodiments, $R^7$ is H.

In some embodiments, the carbohydrate is glucose and $R^1$ and/or $R^2$ can be

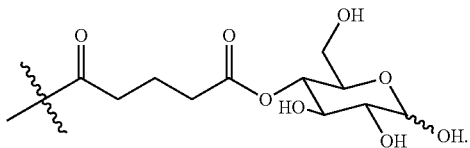 [SMILES: *C(=O)CCCC(=O)OC1C(CO)OC(O)C(O)C1O]

The term "peptide" as used herein is intended to be a generic term which broadly includes short peptides (typically less than 100 amino acids). "Peptide" as used generically herein also includes modified peptides. Generally, a peptide of the invention comprises two or more amino acids. A peptide can be linked by its N-terminus, C-terminus, and/or an amino acid side chain. In some embodiments, the peptide is linked by the side chain of a lysine amino acid present in the peptide.

In some embodiments, $R^1$ and $R^2$ both are not —C(O)$CH_3$.

In some embodiments, a curcumin derivative of formula (I) is not a curcumin derivative described in U.S. Pat. App. Pub. No. 2007/0060644, content of which is herein incorporated by reference in its entirety.

In some embodiments, a curcumin derivative of formula (I) is not a curcumin derivative described in Majhi, et al., "Binding of curcumin and its long chain derivatives to the activator binding domain of novel protein kinase C", *Bioorganic & Medicinal chemistry*, 2010, 18: 1591-1598, content of which is herein incorporated by reference.

Some exemplary curcumin derivatives of formula (I) are shown FIGS. 1A and 1B and include di(acetylsalicyloyl)-curcumin monoacetylsalicyloyl-curcumin, diacetyl-curcumin, monoacetyl-curcumin, diaglutaroyl-curcumin, monoglutaroyl-curcumin, di-gluocose-glutaroyl-curcumin, mono-gluocose-glutaroyl-curcumin, monolinoleol-curcumnin, di-linoleoyl-curcumin and peptide-curcumin conjugates.

The curcumin derivatives described herein have anti-inflammatory activity, anti-cancer activity, and/or are analgesic. Furthermore, the turmeric oil extracts are also analgesic. Furthermore, the inventor has discovered that the curcumin derivatives also show a synergistic effect with anti-inflammatory agents and/or anti-cancer agents.

Aspirin Conjugates

Aspirin (acetylsalicylic acid) is not very water soluble, only 0.33 g in 100 mL. Accordingly, some of the undesirable side effects of aspirin result from undissolved particles in the gastrointestinal mucosa causing ulcers and bleeding. The inventor has discovered that carbohydrate-aspirin conjugates unexpectedly have enhanced anti-cancer and anti-inflammatory activity relative to unconjugated aspirin. Accordingly, in one aspect, the invention provides compounds of formula (II) for treatment of inflammation, an inflammatory disease or condition, or cancer in subject in need thereof.

A compound of formula (II), also referred to as a carbohydrate-salicylic acid conjugate, a salicylic, a carbohydrate-aspirin conjugate or an aspirin conjugate herein, has the following structure:

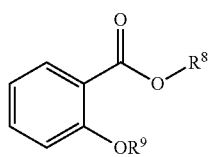

Formula (II)

wherein: $R^8$ is a carbohydrate; $R^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof.

In some embodiments, $R^8$ is selected from the group consisting of glucose, glyceraldehydes, erythrose, threose, ribulose, xylulose, ribose, arabinose, deoxyribose, xylose, lyxose, psicose, fructose, sorbose, tagatose, allose, altrose, mannose, gulose, idose, galactose, talose, fucose, fuculose, rhamnose, sedoheptulose, octose, nonose (Neuraminic acid), and the like.

In some embodiments, $R^9$ is H or acetyl.

In some embodiments, a compound of formula (II) is of formula (IIa):

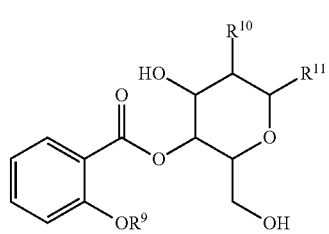

Formula (IIa)

wherein: $R^{10}$ is OH, amino, mono($C_1$-$C_6$alkyl)amino, di($C_1$-$C_6$alkyl)amino, cyclyl, or alkoxy; and $R^{11}$ is H, alkyl, cyclyl, heterocyclyl, aryl, heteroaryl, carbohydrate, or a peptide.

In some embodiments, $R^{10}$ is OH.

In some embodiments, $R^{11}$ is H or an acyl, e.g., $C_1$-$C_6$acyl such as acetyl.

In some embodiments, a compound of formula (II) has the structure shown in formula (IIb):

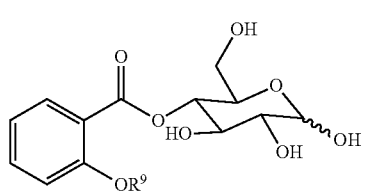

Formula (IIb)

The compounds of formula (II) have enhanced anti-cancer and/or anti-inflammatory activity relative to the anti-cancer and/or anti-inflammatory activity of aspirin. Accordingly, in some embodiments, a compound of formula (II) is at least 10%, at least 20%, at least 30, at least 40%, at least 50%, at least 60%, at least 70%, at least 80%, at least 90%, at least 95%, or at least 100% more active than a unconjugated aspirin under the same conditions. The activity can be as determined in vitro or in vivo.

Furthermore, the compounds of formula (II) have increased solubility relative to the solubility of unconjugated aspirin. Accordingly, in some embodiments, a compound of formula (II) is at least 10%, at least 20%, at least 30%, at least 40%, at least 50%, at least 60%, at least 70%, at least 80%, at least 90%, at least 95%, or at least 100% more soluble than aspirin under the same conditions. The at least amount can be based on weight and/or moles.

Compounds of formula (II) are also described in U.S. Pat. Nos. 3,279,990; 4,241,055; 4,242,330; 4,975,269; 5,157,030; 5,550,762; 5,700,784; and 5,723,453, Int. Pat. App. Pub. No. WO/1986/003206, and French Pat. No. FR M1453, content of all of which is herein incorporated by reference in its entirety.

Compositions Comprising Turmeric Oil or Turmeric Oil Extract

The inventor has also discovered that turmeric oil and/or a turmeric oil extract enhances the anti-inflammatory activity of anti-inflammatory agents and enhances the anti-cancer activity of anti-cancer agents. Accordingly, in another aspect, the invention provides a composition comprising turmeric oil or a turmeric oil extract and a compound selected from the group consisting of anti-cancer agents, an anti-inflammatory agents, curcumin, curcumin derivatives (e.g. compounds of formula (I)), curcumin derivatives, salicylic acid conjugates (e.g. compounds of formula (II)), fish oil, fish oil extract, aspirin and any combinations thereof, wherein the curcumin ether derivative is of formula (III):

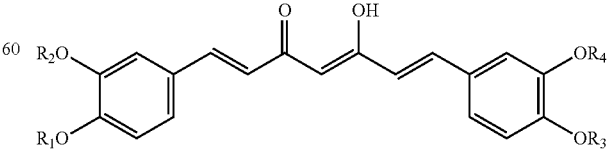

Formula (III)

wherein $R_1$, $R_2$, $R_3$, and $R_4$ are independently H, alky, acyl, trialkylsilyl (—Si(alkyl)$_3$), aryl dialkylsilyl (—Si (alkyl)$_2$aryl), diarylalkylsilyl (—Si(aryl)$_2$alkyl), or triarylsilyl (—Si(aryl)$_3$), each of which can be optionally substituted.

In some compounds of formula (III), at least one of (e.g., one, two, three, or four) $R_1$, $R_2$, $R_3$, and $R_4$ is trialkylsilyl (—Si(alkyl)$_3$), aryl dialkylsilyl (—Si(alkyl)$_2$aryl), diarylalkylsilyl (—Si(aryl)$_2$alkyl), or triarylsilyl (—Si(aryl)$_3$).

In some compounds of formula (III), each of $R_1$, $R_2$, $R_3$, and $R_4$ is independently selected from trialkylsilyl (—Si(alkyl)$_3$), aryl dialkylsilyl (—Si(alkyl)$_2$aryl), diarylalkylsilyl (—Si(aryl)$_2$alkyl), or triarylsilyl (—Si(aryl)$_3$).

In some compounds of formula (III), each of $R_1$, $R_2$, $R_3$, and $R_4$ is independently selected trialkylsilyl (—Si(alkyl)$_3$).

In some compounds of formula (III), $R_2$ and $R_4$ are both alkyl, and $R_1$ and $R_3$ are both alkyl or one of $R_1$ and $R_3$ is H and the other is alkyl.

In some compounds of formula (III), $R_2$ and $R_4$ are both $CH_3$; and $R_1$ and $R_3$ are both alkyl or one of $R_1$ and $R_3$ is H and the other is alkyl.

In some compounds of formula (III), at least one of $R_1$ or $R_3$ is octyl, hexadecyl, or octadecyl.

In some compounds of formula (III), both of $R_1$ and $R_3$ are octyl, hexadecyl, or octadecyl.

In some compounds of formula (III), at least one of (e.g., one, two, three, or four) $R_1$, $R_2$, $R_3$, and $R_4$ is acyl.

Generally, the turmeric oil or the turmeric oil extract and the other component can be present in any ratio (weight ratio or molar ratio) in the composition. Accordingly, the turmeric oil or the turmeric oil extract and the other component can be present at a ratio of 99:1 to 1:99. In some embodiments, the composition comprises turmeric oil or the turmeric extract and the other compound in a 90:10 to 10:9, 80:20 to 20:80, 70:30 to 30:70, 60:40 to 40:60, or 50:50 ratio. In some embodiments, the turmeric oil or turmeric oil extract and the compound ratio is 5:1 to 15:1. In one embodiment, the turmeric oil or turmeric oil extract and the compound ratio is 10:1. In one embodiment, ratio of the turmeric oil or turmeric oil extract to the compound is 1:1.

In some embodiments, in addition to the turmeric oil and/or turmeric oil extract, the composition comprises two of: anticancer agents, an anti-inflammatory agents, curcumin, curcumin derivatives (e.g. compounds of formula (I)), curcumin ether derivatives (e.g. compounds of formula (III)), salicylic acid conjugates (e.g. compounds of formula (II)), fish oil, fish oil extract, and aspirin.

In some embodiments, in addition to the turmeric oil and/or turmeric oil extract, the composition comprises three of: anticancer agents, an anti-inflammatory agents, curcumin, curcumin derivatives (e.g. compounds of formula (I)), curcumin ether derivatives (e.g. compounds of formula (III)), salicylic acid conjugates (e.g. compounds of formula (II)), fish oil, fish oil extract, and aspirin.

When the composition comprises more than one of the above mentioned compounds, ratio of each compound to the turmeric oil or the turmeric oil can be determined separately or ratio for the total of the compounds can be determined. Accordingly, in some embodiments, the composition comprises at least 50%, at least 60%, at least 70%, at least 75%, at least 80%, at least 85%, at least 90%, or at least 95% turmeric oil and/or turmeric oil extract.

Some exemplary compositions of this aspect include, but are not limited to, turmeric oil and aspirin; turmeric oil and a compound of formula (II); turmeric oil and a compound of formula (IIa); turmeric oil and curcumin; turmeric oil and a compound of formula (I); turmeric oil and a compound of formula (III); turmeric oil and di(acetylsalicyloyl)-curcumin; turmeric oil and monoacetylsalicyloyl-curcumin; turmeric oil and diacetyl-curcumin; turmeric oil and monoacetyl-curcumin; turmeric oil and diaglutaroyl-curcumin; turmeric oil and monoglutaroyl-curcumin; turmeric oil and di-gluocose-glutaroyl-curcumin; turmeric oil and mono-gluocose-glutaroyl-curcumin; turmeric oil and monolinoleol-curcumnin; turmeric oil and di-linoleoyl-curcumin; turmeric oil and an anticancer agent; turmeric oil and an anti-inflammatory agent; turmeric oil and fish oil; turmeric oil and fish oil extract; turmeric oil and a curcumin diglutarate monolipid conjugate; turmeric oil and a curcumin diglutarate-dilipid conjugate; turmeric oil and a curcumin-diglutarate-distearin monoester; turmeric oil, a curcumin diglutarate monolipid conjugate and an anti-cancer agent; turmeric oil, a curcumin diglutarate monolipid conjugate and a compound of formula (II); turmeric oil, a curcumin diglutarate monolipid conjugate and an anti-inflammatory agent; turmeric oil, a curcumin diglutarate monolipid conjugate and a compound of formula (II); turmeric oil and aspirin; turmeric oil, aspirin and a curcumin diglutarate monolipid conjugate; turmeric oil and glucose-aspirin conjugate; turmeric oil, aspirin-glucose conjugate and a curcumin diglutarate monolipid conjugate; turmeric oil, an anti-cancer agent and an anti-inflammatory agent; turmeric oil, an anti-cancer agent and a compound of formula (I); turmeric oil, an anti-cancer agent and a compound of formula (III); turmeric oil, an anti-cancer agent and a compound of formula (II); turmeric oil, an anti-inflammatory agent and a compound of formula (I); turmeric oil, an anti-inflammatory agent and a compound of formula (III); turmeric oil, an anti-inflammatory agent and a compound of formula (II); turmeric oil, a compound of formula (I) and a compound of formula (II); turmeric oil, a compound of formula (III) and a compound of formula (II); turmeric oil and aspirin; turmeric oil, aspirin and curcumin; turmeric oil and glucose-aspirin conjugate; and turmeric oil, aspirin-glucose conjugate and curcumin. While these exemplary compositions recite turmeric oil, it is to be understood that a turmeric extract can be substituted for the turmeric oil or added in addition to the turmeric oil in these exemplary compositions.

In some embodiments, the composition comprises a turmeric oil fraction and paclitaxel or a paclitaxel-carbohydrate conjugate. In some further embodiments of this, the composition comprises a turmeric oil fraction and a paclitaxel-carbohydrate conjugate selected from the group consisting of 2'-(GABA-succinoyl)paclitaxel, 2'-(glucose-GABA-succinoyl)paclitaxel, 2'-(glucose-succinoyl)paclitaxel, 2'-(glucose-glutamyl)paclitaxel, 2'-(glucosamide-GABA-succinoyl)paclitaxel, 2'-(glucoseamide-succinoyl)paclitaxel, 2'-(glucoseamide-glutamyl)paclitaxel, 7-(GABA-succinoyl)paclitaxel, 7-(glucose-GABA-succinoyl)paclitaxel, 7-(glucose-succinoyl)paclitaxel, 7-(glucose-glutamyl)paclitaxel, 7-(glucosamide-GABA-succinoyl)paclitaxel, 7-(glucoseamide-succinoyl)paclitaxel, and 7-(glucoseamide-glutamyl)paclitaxel.

Without wishing to be bound by a theory, combining an anti-inflammatory or an anti-cancer agent with turmeric oil and/or a turmeric oil extract leads to enhanced activity for the anti-inflammatory or the anti-cancer agent. Accordingly, in some embodiments, the activity of an anti-inflammatory or an anti-cancer agent is increased by at least 10%, at least 20%, at least 30%, at least 40%, at least 50%, at least 60%, at least 70%, at least 80%, at least 90%, at least 1-fold, at least 2-fold, at least 4-fold, at least 5-fold or more, relative to the activity of the anti-inflammatory, the anti-cancer agent, the turmeric oil or the turmeric oil extract alone. The skilled artisan is well aware of methods and assays for measuring anti-inflammatory or anti-cancer activity of a compound. For example, anti-inflammatory activity can be measured using an assay designed to test the ability of a compound to antagonize the local edema which is characteristic of the inflammatory response. Examples of such assays include, but are not limited to, the carrageenan rat edema test, the oxazolone-induced inflamed mouse ear test, and the arachidonic acid-induced inflamed mouse ear test. Similarly, anti-cancer activity can be determined, for example, by using the LIVE/DEAD® Cell Viability Assays from Invitrogen (Carlsbad, Calif., USA). Without wishing to be bound by a theory, the turmeric oil and/or the turmeric oil extract has a synergistic anti-inflammatory, analgesic and/or anti-cancer activity in combination with an anti-inflammatory and/or anti-cancer agent.

In some embodiments, the turmeric oil fraction increases activity of paclitaxel, e.g., anti-cancer activity, by at least 10%, at least 20%, at least 30%, at least 40%, at least 50%, at least 60%, at least 70%, at least 80%, at least 90%, at least 1-fold, at least 2-fold, at least 4-fold, at least 5-fold or more, relative to the activity of paclitaxel alone.

Compositions Comprising Curcumin or Curcumin Derivative

In one aspect, the invention provides a composition comprising curcumin, a curcumin derivative of formula (I), or a curcumin ether derivative of formula (III) and a compound selected from the group consisting of anti-cancer agents, anti-inflammatory agents, compounds of formula (II), fish oil, fish oil extract, aspirin and any combinations thereof. Generally, curcumin or curcumin derivate and the other component can be present in any ratio (weight ratio or molar ratio) in the composition. Accordingly, the curcumin or the curcumin derivative and the other component can be present at a ratio of 99:1 to 1:99. In some embodiments, the composition comprises the curcumin or the curcumin derivative and the other compound in a 90:10 to 10:90, 80:20 to 20:80, 70:30 to 30:70, 60:40 to 40:60, or 50:50 ratio. In some embodiments, the curcumin or the curcumin derivative and the compound ratio is 5:1 to 15:1. In one embodiment, the curcumin or the curcumin derivative and the compound ratio is 10:1. In one embodiment, the curcrumin or the curcumin derivative and the compound ratio is 1:1. In some embodiments, the composition comprises curcumin and fish oil in a 2:1 ratio by weight.

In some embodiments, the composition comprises curcumin or curcumin derivative, fish oil and lecithin. In some further embodiments of this, the curcumin or curcumin derivative, fish oil and lecithin are present in a ratio of 1-10: 1-10:1-10 by weight. In one embodiment, the curcumin or curcumin derivative, fish oil and lecithin are present in a ratio of 4:2.5:1 by weight. Without wishing to be bound by theory, lecithin can increase the mixing ability of the various components of the composition and also has its own beneficial effect.

The term "lecithin" is used herein in its art-recognized manner. See, for example, the United States Pharmacopeia/ National Formulary, published by the United States Pharmacopeial Convention, Inc. (Rockville, Md.). The term lecithin as conventionally used in the art refers to pure phosphatidyl choline and also to crude phospholipid mixtures, containing a variety of other compounds such as fatty acids, triglycerides, sterols, carbohydrates and glycolipids.

Lecithin includes a complex mixture of acetone-insoluble phosphatides, of which phosphatidylcholine is a significant component. The term lecithin is also used as a synonym for phosphatidylcholine. Commercially supplied lecithin is typically derived from egg yolk, soybeans, or corn. As used herein, the term "lecithin" encompasses phosphatidyl choline obtained naturally or synthetically, including de-oiled or de-gummed products; derivatives of lecithin and combinations of various types of lecithin. Commercial lecithin is currently available in more than forty different formulations (from sources such as American Lecithin Co.; Lucas Meyer Inc. and Central Soya Inc. among others) varying from crude oily extracts from natural sources to purified and synthetic phospholipids, all intended to be encompassed by the term "lecithin" as used herein.

Lecithin can be made more hydrophilic by hydroxylation of unsaturated fatty acid constituents, fractionation or compounding with dispersing agents. Moreover, lecithin may be hydroxylated by treating the phosphatides with hydrogen peroxide or peracids in the presence of water-soluble aliphatic carboxylic acids. Alternatively, lecithin may also be hydrolyzed enzymatically to yield a powdered soybean lecithin. Another lecithin derivative is lysolecithin, which results from the interaction of the enzyme phospholipase with lecithin, for example in pancreatic juices. Therefore lecithin derivatives are compounds which can be the result of hydroxylation or enzymatic reaction, as mentioned above or other chemical modification of lecithin, included in the broad term "lecithin".

Some examples of suitable lecithins available from Central Soya Inc. of Iowa include BLENDMAX, CENTROBAKE, CENTROCAP, CENTROL CA, CENTROLENE, CENTROMIX, CENTROPHASE, CENTROPHIL, NATHIN and PRECEPT. These names may represent either a single lecithin, or a series of lecithin products, all of which are considered useful for the purposes described herein.

When the composition comprises more than one of the above mentioned compounds, ratio of each compound to the curcumin or curcumin derivative can be determined separately or ratio for the total of the compounds can be determined. Accordingly, in some embodiments, the composition comprises at least 50%, at least 60%, at least 70%, at least 75%, at least 80%, at least 85%, at least 90%, or at least 95% curcumin derivative.

Without wishing to be bound by theory, a composition described herein may comprise a small amount (0.1%-5%) of curcumin in the composition as an antioxidant to preserve the composition.

Some exemplary compositions of this aspect include, but are not limited to, curcumin derivative and aspirin; curcumin derivative and a compound of formula (II); curcumin derivative and curcumin; curcumin ether derivative and aspirin; curcumin ether derivative and a compound of formula (II); aspirin and di(acetylsalicyloyl)-curcumin; aspirin and monoacetylsalicyloyl-curcumin; aspirin and diacetyl-curcumin; aspirin and monoacetyl-curcumin; aspirin and diaglutaroyl-curcumin; aspirin and monoglutaroyl-curcumin; aspirin and di-gluocose-glutaroyl-curcumin; aspirin and mono-gluocose-glutaroyl-curcumin; aspirin and monolinoleol-curcumnin; aspirin and di-linoleoyl-curcumin; a compound of formula (II) and di(acetylsalicyloyl)-curcumin; a compound of formula (II) and monoacetylsalicyloyl-curcumin; a compound of formula (II) and diacetyl-curcumin; a compound of formula (II) and monoacetyl-curcumin; a compound of formula (II) and diaglutaroyl-curcumin; a compound of formula (II) and monoglutaroyl-curcumin; a compound of formula (II) and di-gluocose-glutaroyl-curcumin; a compound of formula (II) and mono-gluocose-glutaroyl-curcumin; a compound of formula (II) and monolinoleol-curcumnin; a compound of formula (II) and di-linoleoyl-curcumin; a compound of formula (IIb) and di(acetylsalicyloyl)-curcumin; a compound of formula (IIb) and monoacetylsalicyloyl-curcumin; a compound of formula (IIb) and diacetyl-curcumin; a compound of formula (IIb) and monoacetyl-curcumin; a compound of formula (IIb) and diaglutaroyl-curcumin; a compound of formula (IIb) and monoglutaroyl-curcumin; a compound of formula (IIb) and di-gluocose-glutaroyl-curcumin; a compound of formula (IIb) and mono-gluocose-glutaroyl-curcumin; a compound of formula (IIb) and monolinoleol-curcumin; a compound of formula (IIb) and di-linoleoyl-curcumin; a compound of formula (IIc) and di(acetylsalicyloyl)-curcumin; a compound of formula (IIc) and monoacetylsalicyloyl-curcumin; a compound of formula (IIc) and diacetyl-curcumin; a compound of formula (IIc) and monoacetyl-curcumin; a compound of formula (IIc) and diaglutaroyl-curcumin; a compound of formula (IIc) and monoglutaroyl-curcumin; a compound of formula (IIc) and di-gluocose-glutaroyl-curcumin; a compound of formula (IIc) and mono-gluocose-glutaroyl-curcumin; a compound of formula (IIc) and monolinoleol-curcumnin; a compound of formula (IIc) and di-linoleoyl-curcumin; curcumin and aspirin; curcumin and glucose-aspirin conjugate; curcumin and fish oil; and curcumin, fish oil and lecithin;

In some embodiments, the composition comprises a curcumin derivative of formula (I), or a curcumin ether derivative of formula (III) and paclitaxel or a paclitaxel-carbohydrate conjugate. In some further embodiments of this, the composition comprises a curcumin derivative of formula (I), or a curcumin ether derivative of formula (III) and a paclitaxel-carbohydrate conjugate selected from the group consisting of 2'-(GABA-succinoyl)paclitaxel, 2'-(glucose-GABA-succinoyl)paclitaxel, 2'-(glucose-succinoyl)paclitaxel, 2'-(glucose-glutamyl)paclitaxel, 2'-(glucosamide-GABA-succinoyl)paclitaxel, 2'-(glucoseamide-succinoyl)paclitaxel, 2'-(glucoseamide-glutamyl)paclitaxel, 7-(GABA-succinoyl) paclitaxel, 7-(glucose-GABA-succinoyl)paclitaxel, 7-(glucose-succinoyl)paclitaxel, 7-(glucose-glutamyl)paclitaxel, 7-(glucosamide-GABA-succinoyl)paclitaxel, 7-(glucoseamide-succinoyl)paclitaxel, and 7-(glucoseamide-glutamyl)paclitaxel.

Without wishing to be bound by theory, combining an anti-inflammatory or an anti-cancer agent with curcumin and/or the curcumin derivative leads to enhanced activity for the anti-inflammatory or the anti-cancer agent. Accordingly, in some embodiments, the activity of an anti-inflammatory or an anti-cancer agent is increased by at least 10%, at least 20%, at least 30%, at least 40%, at least 50%, at least 60%, at least 70%, at least 80%, at least 90%, at least 1-fold, at least 2-fold, at least 4-fold, at least 5-fold or more, relative to the activity of the anti-inflammatory, the anti-cancer agent, the curcumin or the curcumin derivative alone. Without wishing to be bound by a theory, the curcumin and the curcumin derivative have a synergistic anti-inflammatory, analgesic and/or anti-cancer activity in combination with an anti-inflammatory and/or anti-cancer agent.

In some embodiments, the composition comprises two or more of turmeric oil fractions, curcumin, curcumin derivarives, and fish oil. Without wishing to be bound by a theory, a composition comprising two or more of turmeric oil fractions, curcumin, curcumin derivarives, and fish oil have enhanced anti-inflammatory and analgesic activity relative to the turmeric oil fraction, curcumin, curcumin derivative or fish oil alone. In other words, a composition comprising two or more of turmeric oil fractions, curcumin, curcumin derivarives, and fish oil has a synergistic anti-inflammatory and analgesic activity.

Methods of Use

The extracts, compounds and compositions described herein have anti-inflammatory, analgesic and/or anti-cancer properties. Accordingly, in one aspect the inventions provides a method of treating a subject for inflammation, or a disease or condition associated with inflammation, the method comprising administering a therapeutically effective amount of a turmeric oil extract, a curcumin derivative, a curcumin ether derivative, a salicylic acid conjugate, turmeric oil extract comprising composition, a curcumin derivative comprising composition, or any combinations thereof to a subject in need thereof.

As used herein, an anti-inflammation treatment aims to prevent or slow down (lessen) an undesired physiological change or disorder, such as the development or progression of the inflammation. Beneficial or desired clinical results include, but are not limited to, alleviation of a symptom or symptoms, diminishment of extent of disease, stabilized (i.e., not worsening) state of disease, delay or slowing of inflammatory disease progression, amelioration or palliation of the disease state, and remission (whether partial or total). An anti-inflammatory treatment can also mean prolonging survival as compared to expected survival if not receiving treatment. In one aspect, an anti-inflammatory treatment can completely suppress the inflammatory response.

As used herein, "inflammation" refers to the complex biological response of vascular tissues to harmful stimuli, such as pathogens, damaged cells, or irritants. Inflammation is a protective attempt by the organism to remove the injurious stimuli as well as initiate the healing process for the tissue. Accordingly, the term "inflammation" includes any cellular process that leads to the production of pro-inflammatory cytokines, inflammation mediators and/or the related downstream cellular events resulting from the actions of the cytokines thus produced, for example, fever, fluid accumulation, swelling, abscess formation, and cell death. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. As used herein, "inflammation" also refers to any cellular process that leads to the activation of caspase-1 or caspase-5.

As used herein, the term "inflammation" refers to both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response.

As used herein, the term "inflammation" includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

As used herein, the term "specific defense system" is intended to refer to that component of the immune system that reacts to the presence of specific antigens. Inflammation is said to result from a response of the specific defense system if the inflammation is caused by, mediated by, or associated with a reaction of the specific defense system. Examples of inflammation resulting from a response of the specific defense system include the response to antigens such as rubella virus, autoimmune diseases such as lupus erythematosus, rheumatoid arthritis, Reynaud's syndrome, multiple sclerosis etc., delayed type hypersensitivity response mediated by T-cells, etc. Chronic inflammatory diseases and the rejection of transplanted tissue and organs are further examples of inflammatory reactions of the specific defense system.

As used herein, a reaction of the "non-specific defense system" is intended to refer to a reaction mediated by leukocytes incapable of immunological memory. Such cells include granulocytes and macrophages. As used herein, inflammation is said to result from a response of the nonspecific defense system, if the inflammation is caused by, mediated by, or associated with a reaction of the non-specific defense system. Examples of inflammation which result, at least in part, from a reaction of the non-specific defense system include inflammation associated with conditions such as: adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; acute purulent meningitis or other central nervous system inflammatory disorders; thermal injury; hemodialysis; leukophoresis; ulcerative colitis; Crohn's disease; necrotizing enterocolitis; granulocyte transfusion associated syndromes; and cytokine-induced toxicity. The term immune-mediated refers to a process that is either autoimmune or inflammatory in nature.

The term "inflammatory diseases" refers to diseases and conditions associated with inflammation. Exemplary inflammatory diseases include, but are not limited to, rheumatoid arthritis, inflammatory bowel disease, pelvic inflammatory disease, ulcerative colitis, psoriasis, systemic lupus erythematosus, multiple sclerosis, type 1 diabetes mellitus, psoriasis, vaculitis, allergic inflammation such as allergic asthma, atopic dermatitis, and contact hypersensitivity. Other examples of inflammatory diseases or disorders include, but are not limited to, rheumatoid arthritis, multiple sclerosis (MS), systemic lupus erythematosus, Graves' disease (overactive thyroid), Hashimoto's thyroiditis (underactive thyroid), Type 1 diabetes mellitus, celiac disease, Crohn's disease and ulcerative colitis, Guillain-Barre syndrome, primary biliary sclerosis/cirrhosis, sclerosing cholangitis, autoimmune hepatitis, Raynaud's phenomenon, scleroderma, Sjogren's syndrome, Goodpasture's syndrome, Wegener's granulomatosis, polymyalgia rheumatica, temporal arteritis/ giant cell arteritis, chronic fatigue syndrome CFS), psoriasis, autoimmune Addison's Disease, ankylosing spondylitis, Acute disseminated encephalomyelitis, antiphospholipid antibody syndrome, aplastic anemia, idiopathic thrombocytopenic purpura, Myasthenia gravis, opsoclonus myoclonus syndrome, optic neuritis, Ord's thyroiditis, pemphigus, pernicious anaemia, polyarthritis in dogs, Reiter's syndrome, Takayasu's arteritis, warm autoimmune hemolytic anemia, Wegener's granulomatosis, fibromyalgia (FM), autoinflammatory PAPA syndrome, Familial Mediaterranean Fever, familial cold autoinflammatory syndrome, Muckle-Wells syndrome, the neonatal onset multisystem inflammatory disease, inflammatory or allergic diseases (e.g., systemic anaphylaxis or hypersensitivity responses, drug allergies, insect sting allergies), inflammatory bowel diseases (e.g., colitis, ileitis and enteritis; vaginitis), psoriasis and inflammatory dermatoses (e.g., dermatitis, eczema, atopic dermatitis, allergic contact dermatitis, urticaria, vasculitis, spondyloarthropathies, scleroderma, respiratory allergic diseases (e.g., asthma, allergic rhinitis, hypersensitivity lung diseases), autoimmune diseases (e.g. arthritis (rheumatoid and psoriatic), osteoarthritis, multiple sclerosis, systemic lupus erythematosus, diabetes mellitus, glomerulonephritis, and the like), graft rejection (including allograft rejection and graft-v-host disease), and other diseases in which undesired inflammatory responses are to be inhibited (e.g., myositis, inflammatory CNS disorders such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Bechet's syndrome), chronic prostatitis, glomerulonephritis, inflammatory bowel diseases, pelvic inflammatory disease, reperfusion injury, silicosis, vasculitis, inflammatory myopathies, hypersensitivities, migraine, psoriasis, gout, and atherosclerosis.

Without wishing to be bound by theory, one mechanism by which administration of turmeric oil extract and/or curcumin derivatives may treat disease is through inhibition of the activity of AP-1, NF-κB and/or GSTP1-1. Inhibition of NF-κB results in a decrease in NF-κB activity, and includes direct inhibition and indirect inhibition. Direct inhibition is the direct effect of a turmeric oil extract and/or a curcumin derivative on NF-κB and its activity. For example, one type of direct inhibition of NF-κB is a block of NF-KB DNA interactions. Indirect inhibition, on the other hand, involves the effect of a turmeric oil extract and/or a curcumin derivative on other compounds involved in the regulation of NF-κB that leads to a decrease in NF-κB activity. For example, as phosphorylation of the NF-κB regulator IκB by IκB kinases (IKK) or Src family kinases (SFK) results in a dysregulation of NF-κB, and an accompanying increase in NF-κB activity, inhibition of IKK or SFK by turmeric oil extracts and/or curcumin derivatives provides an example of indirect inhibition.

Inhibition of AP-1 results in a decrease in AP-1 activity, and includes direct inhibition and indirect inhibition. Direct inhibition is the direct effect of a turmeric oil extract and/or a curcumin derivative on AP-1 (or its subunits) and its activity. Indirect inhibition, on the other hand, involves the effect of a turmeric oil extract and/or a curcumin derivative on other compounds involved in the regulation of AP-1 that leads to a decrease in AP-1 activity. For example, indirect inhibition of AP-1 activity may occur as a result of an affect on AP-1 activating proteins such as mitogen-activated protein kinases (MAPK) or c-Fos-regulating kinase (FRK).

Inhibition of GSTP1-1 results in a decrease GSTP1-1 activity, and includes direct inhibition and indirect inhibition. Direct inhibition is the direct effect of a turmeric oil extract and/or a curcumin derivative on GSTP1-1 (or its subunits) and its activity. Indirect inhibition, on the other hand, involves the effect of a turmeric oil extract and/or a curcumin derivative on other compounds involved in the regulation of GSTP1-1 that leads to a decrease in GSTP1-1 activity.

Also described herein is a method of treating a subject afflicted with cancer, a precancerous condition and/or metastasis, the method comprising administering a therapeutically effective amount of a turmeric oil extract, a curcumin derivative, a curcumin ether derivative, a salicylic acid conjugate, a composition described herein, or any combinations thereof to a subject in need thereof. By "reduced" in the context of cancer is meant reduction of at least 10% in the growth rate of a tumor or the size of a tumor or cancer cell burden.

As used herein, an anti-cancer treatment aims to reduce, prevent or eliminate cancer cells or the spread of cancer cells or the symptoms of cancer in the local, regional or systemic circulation. Anti-cancer treatment also means the direct treatment of tumours, for example by reducing or stabilizing their number or their size (curative effect), but also by preventing the in situ progression of tumour cells or their diffusion, or the establishment of tumours; this also includes the treatment of deleterious effects linked to the presence of such tumours, in particular the attenuation of symptoms observed in a patient or an improvement in quality of life.

As used herein, the term "cancer" refers to an uncontrolled growth of cells that may interfere with the normal functioning of the bodily organs and systems. Cancers that migrate from their original location and seed vital organs can eventually lead to the death of the subject through the functional deterioration of the affected organs. A metastasis is a cancer cell or group of cancer cells, distinct from the primary tumor location resulting from the dissemination of cancer cells from the primary tumor to other parts of the body. At the time of diagnosis of the primary tumor mass, the subject may be monitored for the presence of in transit metastases, e.g., cancer cells in the process of dissemination. As used herein, the term cancer, includes, but is not limited to the following types of cancer, breast cancer, biliary tract cancer, bladder cancer, brain cancer including glioblastomas and medulloblastomas; cervical cancer; choriocarcinoma; colon cancer; endometrial cancer; esophageal cancer, gastric cancer; hematological neoplasms including acute lymphocytic and myelogenous leukemia; T-cell acute lymphoblastic leukemia/lymphoma; hairy cell leukemia; chromic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma, Wilms tumor. Examples of cancer include but are not limited to, carcinoma, including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Other cancers will be known to the artisan. In some embodiments, cancer is pancreatic, breast or prostate cancer.

As used herein, the term "precancerous condition" has its ordinary meaning, i.e., an unregulated growth without metastasis, and includes various forms of hyperplasia and benign hypertrophy. Accordingly, a "precancerous condition" is a disease, syndrome, or finding that, if left untreated, can lead to cancer. It is a generalized state associated with a significantly increased risk of cancer. Premalignant lesion is a morphologically altered tissue in which cancer is more likely to occur than its apparently normal counterpart. Examples of pre-malignant conditions include, but are not limited to, oral leukoplakia, actinic keratosis (solar keratosis), Barrett's esophagus, atrophic gastritis, benign hyperplasia of the prostate, precancerous polyps of the colon or rectum, gastric epithelial dysplasia, adenomatous dysplasia, hereditary non-polyposis colon cancer syndrome (HNPCC), Barrett's esophagus, bladder dysplasia, precancerous cervical conditions, and cervical dysplasia.

Without wishing to be bound by theory, administration of a turmeric oil extract, a curcumin derivative, and/or a salicylic acid conjugate can inhibit the activity Glutathione S-transferase Pl-1 (GSTP1-1), NFκB and/or AP-1. Inhibition of GSTP1-1 may occur by affecting gene transcription and/or by direct effects on enzyme activity.

Administration of the turmeric oil extract, the curcumin derivative, and/or the salicylic acid conjugate is especially advantageous in cases where the cancer cells may develop or have developed resistance to one or more anti-cancer agents; and/or when the cancer cells overexpress GSTP1-1. Expression of GSTP1-1 may allow the cancer cell to pump out the anti-cancer agent, and by inhibiting the activity of GSTP1-1, the turmeric oil extract, the curcumin derivative, and/or the salicylic acid conjugate can preserve or prolong the cytostatic or cytotoxic effects of the anti-cancer agent. Compositions described herein are particularly useful for improving the effectiveness of anti-cancer agents by preventing GSTP1-1's inhibition of pro-apoptotic factors, particularly c-Jun N-terminal kinase (JNK).

Curcumin was shown recently to inhibit apoptosis in cancer cells in part through its ability to inhibit the expression of GSTP1-1 mRNA and protein, which was demonstrated to be the result of inhibition of the activation of NFκB. This observation that compounds such as curcumin can block activation of NFκB raises the possibility that synthetic drugs can be developed that are more potent than curcumin, and that these drugs will promote apoptosis in cancer cells. These drugs could sensitize cancer cells to conventional adjuvant chemotherapy by blocking the NFκB-dependent development of the anti-apoptotic prosurvival state, and inhibit the expression of GSTP1-1. In addition, curcumin inhibits the GSTP1-1 catalyzed conjugation of glutathione with electrophiles. Furthermore, curcumin inhibits the proliferation of a variety of tumor cells and has anti-metastatic activity, possibly owing to its ability to induce apoptosis by inhibiting NFκB.

Curcumin contains two alpha, beta-unsaturated carbonyl groups, one of which exists as the enol tautomer. Curcumin reacts with glutathione; this reaction is accelerated by GSTP1-1, indicating that curcumin is a substrate of GSTP1-1, albeit a poor substrate. Curcumin also inhibits GSTP1-1 in its conjugation of glutathione with other electrophiles, suggesting that curcumin is both a substrate and an inhibitor of GSTP1-1. This is consistent with the known inhibition of GSTP1-1 by the flavonoid quercetin, which, like curcumin, is also a polyphenol. Curcumin itself has low bioavailability and therefore is not a promising drug.

Derivatives of curcumin with good bioavailability can provide new anti-cancer drugs that, for example, can inhibit the catalytic activity of GSTP1-1, thereby sensitizing cancer cells to conventional chemotherapy by drugs that normally are metabolized through GSTP1-1 catalyzed conjugation with glutathione; and/or, through inhibition of GSTP1-1 and/or NFκB the curcumin derivatives, contribute to improved chemotherapeutic drug sensitivity of cancer cells by promoting the pro-apoptotic state. While not wishing to be bound by theory, these derivatives thus may have a dual mechanism of action—both the inhibition of the catalytic activity of GSTP1-1 and the down-regulation of GSTP1-1 transcription through inhibition of NFκB. GSTP1-1 inhibitors may limit the ability of GSTP1-1 to inactivate other cancer drugs and can prove to be synergistic when combined with other anticancer agents.

As used herein, a "subject" means a human or animal. Examples of subjects include primates (e.g., humans, and monkeys). Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female. A subject can be one who has not been previously diagnosed with inflammation, inflammatory disease or condition, and/or cancer.

Preferably, the subject is a mammal. The mammal can be a human, non-human primate, mouse, rat, dog, cat, horse, or cow, but are not limited to these examples. Mammals other than humans can be advantageously used as subjects that represent animal models of inflammatory disease or disorder, or as animal models of cancer. In addition, the methods and compositions described herein can be used to treat domesticated animals and/or pets.

A subject can be one who has been previously diagnosed with inflammation, inflammatory disease or condition, and/or cancer. Without wishing to be bound by a theory, a subject can be diagnosed as having an inflammatory disease by having increased levels of at least one inflammatory disease marker compared to the level of that marker in a subject not having the inflammatory disease. Pro-inflammatory cytokines and inflammation mediators include, but are not limited to, IL-1-alpha, IL-1-beta, IL-6, IL-8, IL-11, IL-12, IL-17, IL-18, TNF-alpha, leukocyte inhibitory factor (LIF), IFN-gamma, Oncostatin M (OSM), ciliary neurotrophic factor (CNTF), TGF-beta, granulocyte-macrophage colony stimulating factor (GM-CSF), and chemokines that chemoattract inflammatory cells. A number of assays for in vivo state of inflammation are known in the art. See for example U.S. Pat. Nos. 5,108,899 and 5,550,139, contents of both of which are herein incorporated by reference.

A method described herein can further comprise selecting a subject who has inflammation, inflammatory disease or condition, and/or cancer. The method can also comprise the step of diagnosing a subject for inflammation, inflammatory disease or condition, and/or cancer before onset of administration or treatment regime.

The phrase "therapeutically-effective amount" as used herein means that amount of a compound, material, or composition comprising a conjugate which is effective for producing some desired therapeutic effect in at least a sub-population of cells in an animal at a reasonable benefit/risk ratio applicable to any medical treatment.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject.

A conjugate described herein can be administered by any appropriate route known in the art including, but not limited to, oral or parenteral routes, including intravenous, intramuscular, subcutaneous, transdermal, airway (aerosol), pulmonary, nasal, rectal, vaginal, and topical (including on the skin, and body cavities, such as buccal, vaginal, rectal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments of the aspects described herein, the compositions are administered by intravenous infusion or injection. In some embodiments, administration is oral.

Pharmaceutical Compositions

For administration to a subject, a compound and/or composition described herein can be provided in pharmaceutically acceptable compositions. Accordingly, in one aspect, the invention provides a pharmaceutical composition comprising one or more of a compound and/or composition described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material. A pharmaceutically acceptable carrier will not promote the raising of an immune response to an agent with which it is admixed, unless so desired. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The amount of a compound or composition described herein that can be combined with a carrier material to produce a single dosage form will generally be that amount of the compound that produces a therapeutic effect. Generally out of one hundred percent, this amount will range from about 0.001% to 99% of the compound, preferably from about 0.01% to about 70%, most preferably from 5% to about 30%.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the $IC_{50}$ (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The dosage may be determined by a physician and adjusted, as necessary, to suit observed effects of the treatment. Generally, the compositions are administered so that a compound or composition described herein is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the conjugates described herein. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The compounds or the compositions described herein can be administrated to a subject in combination with one or more pharmaceutically active agents. Exemplary pharmaceutically active compound include, but are not limited to, those found in *Harrison's Principles of Internal Medicine*, 13th Edition, Eds. T. R. Harrison et al. McGraw-Hill N.Y., NY; Physicians Desk Reference, 50th Edition, 1997, Oradell N.J., Medical Economics Co.; Pharmacological Basis of Therapeutics, 8th

Edition, Goodman and Gilman, 1990; United States Pharmacopeia, The National Formulary, USP XII NF XVII, 1990; current edition of Goodman and Oilman's *The Pharmacological Basis of Therapeutics*; and current edition of The Merck Index, the complete content of all of which are herein incorporated in its entirety.

The compound or the composition and the pharmaceutically active agent can be administrated to the subject in the same pharmaceutical composition or in different pharmaceutical compositions (at the same time or at different times). When administrated at different times, they can be administered within 5 minutes, 10 minutes, 20 minutes, 60 minutes, 2 hours, 3 hours, 4, hours, 8 hours, 12 hours, 24 hours of administration of the other When administered in different pharmaceutical compositions, routes of administration can be different.

Anti-Inflammatory Agents

As used herein, the term "anti-inflammatory compound" or "anti-inflammatory agent" is used to describe any compound (including its analogs, derivatives, prodrugs and pharmaceutically salts) which may be used to treat inflammation or inflammation related disease or disorder. Anti-inflammatory agents include, but are not limited to, the known steroidal anti-inflammatory and non-steroidal antiinflammatory drugs (NSAIDs). Exemplary steroidal anti-inflammatory agents include but are not limited to 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, derivatives thereof and mixtures thereof. Exemplary nonsteroidal anti-inflammatory agents include but are not limited to COX inhibitors (COX-1 or COX nonspecific inhibitors) and selective COX-2 inhibitors. Exemplary COX inhibitors include but are not limited to salicylic acid derivatives such as aspirin, sodium salicylate, choline magnesium trisalicylate, salicylate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam); alkanones such as nabumetone; derivatives thereof and mixtures thereof. Exemplary COX-2 inhibitors include but are not limited to diarylsubstituted furanones such as refecoxib; diaryl-substituted pyrazoles such as celecoxib; indole acetic acids such as etodolac and sulfonanilides such as nimesulide; derivatives thereof and mixtures thereof.

Anti-Cancer Agents

As used herein, the term "anti-cancer compound" or "anti-cancer agent" is used to describe any compound (including its analogs, derivatives, prodrugs and pharmaceutically salts) which may be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety. Some exemplary paclitaxel-carbohydrate conjugates include, but are not limited to, 2'-(GABA-succinoyl)paclitaxel, 2'-(glucose-GABA-succinoyl)paclitaxel, 2'-(glucose-succinoyl)paclitaxel, 2'-(glucose-glutamyl)paclitaxel, 2'-(glucosamide-GABA-succinoyl)paclitaxel, 2'-(glucoseamide-succinoyl)paclitaxel, 2'-(glucoseamide-glutamyl)paclitaxel, 7-(GABA-succinoyl)paclitaxel, 7-(glucose-GABA-succinoyl)paclitaxel, 7-(glucose-succinoyl)paclitaxel, 7-(glucose-glutamyl)paclitaxel, 7-(glucosamide-GABA-succinoyl)paclitaxel, 7-(glucoseamide-succinoyl)paclitaxel, and 7-(glucoseamide-glutamyl)paclitaxel.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities of ingredients or reaction conditions used herein should be understood as modified in all instances by the term "about." The term "about" when used in connection with percentages may mean±1%. Furthermore, the term "about" can mean within ±1% of a value.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description.

Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) above or below a reference level. The term refers to statistical evidence that there is a difference. It is defined as the probability of making a decision to reject the null hypothesis when the null hypothesis is actually true. The decision is often made using the p-value.

As used herein, the term "synergistic" means a combination of components wherein the activity of the combination is greater than the additive of the individual activities of each component of the combination As used herein, the term "anti-cancer activity" or "anti-cancer properties" refers to the inhibition (in part or in whole) or prevention of unregulated cell growth and/or the inhibition (in part or in whole) or prevention of a cancer as defined herein. Anticancer activity includes, e.g., the ability to reduce, prevent, or repair genetic damage, modulate undesired cell proliferation, modulate misregulated cell death, or modulate mechanisms of metastasis (e.g., ability to migrate).

As used herein, the term "anti-inflammatory activity" refers to prevention or reduction of one or more indicia of inflammation.

As used herein, the term "analgesic" refers to a compound capable of producing analgesia, i.e., reducing or inhibiting pain by altering perception of nociceptive stimuli without producing anesthesia or loss of consciousness.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, one or more symptoms of a disease or disorder are alleviated by at least 5%, at least 10%, at least 20%, at least 30%, at least 40%, or at least 50%.

As used herein, the term "oligosaccharide" refers without limitation to several (e.g., two to ten) covalently linked monosaccharide units. Oligosaccharides include, but are not limited to, disaccharides (i.e., two monosaccharide units) such as sucrose, lactose, maltose, isomaltose, cellobiose and the like.

As used herein, the term "polysaccharide" refers without limitation to many (e.g., eleven or more) covalently linked monosaccharide units. Polysaccharides can have molecular masses ranging well into millions of daltons. The polysaccharide can be homopolysaccharides or heteropolysaccharides. Whereas the homopolysaccharides contain only one kind of unit, the heteropolysaccharides consist of monomer units of different kinds. Exemplary polysaccharides include, but are not limited to, cellulose, chitin, starch, glycogen, glycosaminoglycans (e.g., hyaluronic acid, chondroitin-4-sulfate, chondroitin-6-sulfate, dermatan sulfate, keratin sulfate, heparin and the like) and the like. The di-, tri-, oligo- and poly-saccharides can comprise 1->4, 1->6 or a mixture of 1->4 and 1->6 linkages.

As used herein, the term "fish oil" indicates oil and fat extracted from animals living in water (namely, fish oil in a broad sense) and fish oil extracted from fish (fish oil in a narrow sense), sea animals oil and cod-liver oil are included. All type of said fish oil (fish oil in broad sense) contains EPA, DHA and other types of highly unsaturated fatty acid and/or their esters. And the term "fish oil extract" indicates fatty acid having 2 or more unsaturated bonds obtained by refining and separating of said fish oil in broad sense, and as the concrete example, EPA or DHA can be mentioned, however the invention is, not limited to them. In the present invention, the following can be used as the fish oil: crude fish oil; lower refined fish oil; highly refined fish oil; and mixtures thereof.

In general, fish oil extracted from sardine, mackerel, cod-fish and tuna (fish oil in a narrow sense), lower and highly refined oil of it, highly unsaturated fatty acid obtained from said fish oil and its ester are preferably used. Further, in the present invention, the fish oil or fish oil extract which comprises at least 10% by weight of DHA and/or EPA is desirable.

The term "alkyl" refers to saturated non-aromatic hydrocarbon chains that may be a straight chain or branched chain, containing the indicated number of carbon atoms (these include without limitation methyl, ethyl, propyl, iso-propyl, butyl, 2-methyl-ethyl, t-butyl, allyl, or propargyl), which may be optionally inserted with N, O, or S. For example, $C_1$-$C_6$ indicates that the group may have from 1 to 6 carbon atoms in it.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "cyclyl" or "cycloalkyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examplary heterocyclyl groups include, but are not limited to piperazinyl, pyrrolidinyl, dioxanyl, morpholinyl, tetrahydrofuranyl, and the like.

The term "aryl" refers to monocyclic, bicyclic, or tricyclic aromatic ring system wherein 0, 1, 2, 3, or 4 atoms of each ring may be substituted by a substituent. Examplary aryl groups include, but are not limited to, phenyl, naphthyl, anthracenyl, azulenyl, fluorenyl, indanyl, indenyl, naphthyl, phenyl, tetrahydronaphthyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "acyl" refers to an alkylcarbonyl or arylcarbonyl substituent, wherein the alkyl or aryl portion may be optionally substituted.

The term "optionally substituted" means that the specified group or moiety, such as an alkyl group, alkenyl group, and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halogen, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnej ad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", *Arfv. Drug Delivery Rev.* 8(1): 1-38 (1992); Fleisher et al. "Improved oral drug delivery: solubility limitations overcome by the use of prodrugs", *Arfv. Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs, [Symp.]* Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The present invention can be defined in any of the following numbered paragraphs:

1. A turmeric oil extract obtained by high vacuum distillation of turmeric oil and collecting a distillate at 70-100° C. or at 100-130° C.
2. The turmeric oil extract of paragraph 1, wherein the extract is produced by a process comprising the steps of: (i) extracting a turmeric powder with hexane; (ii) distilling the extract of (i) to obtain a distillate at 115-135° C. under high vacuum; (iii) distilling the distillate of (ii) to obtain a distillate at 95-112° C. under high vacuum; (iv) distilling the distillate of (iii) to obtain a distillate at 100-110° C. under high vacuum; and (v) distilling the distillate of (iv) to obtain the extract as a distillate at 120-123° C. under high vacuum.
3. The turmeric oil extract of paragraph 1, wherein the extract is produced by a process comprising the steps of: (i) extracting a turmeric powder with hexane; (ii) distilling the extract of (i) to obtain a distillate at 115-135° C. under high vacuum; (iii) distilling the distillate of (ii) to obtain a distillate at 95-112° C. under high vacuum; (iv) distilling the distillate of (iii) to obtain a distillate at 100-110° C. under high vacuum; (v) distilling the distillate of (iv) to obtain a distillate at 100-120° C. and at 124° C. under high vacuum; (vi) combining the distillates obtained in (v) and obtaining the extract by eluting the combined distillates from a column using one volume of hexane, one volume 5% of ethyl acetate/hexane, and one volume 1% ethyl acetate/Hexane.
4. The turmeric oil extract of any of paragraphs 1-3, wherein the high vacuum is less than about 250 torr.
5. The turmeric oil extract of any of paragraphs 1-4, wherein at least one compound in the extract comprises at least 50% of the extract.
6. The turmeric oil extract of any of paragraphs 1-5, wherein the extract comprises from about 70 to about 75% carbon and from about 5 to about 10% hydrogen.
7. The turmeric oil extract of any of paragraphs 1-6, wherein the extract has NMR spectra shown in FIG. 2A, FIG. 2B, FIG. 3A, FIG. 3B, or FIG. 3C.
8. The turmeric oil extract of any of paragraphs 1-7, wherein the extract is anti-inflammatory, anti-cancer and/or analgesic.
9. The turmeric oil extract of any of paragraphs 1-8, wherein the extract has a synergistic anti-inflammatory activity and/or analgesic activity with an anti-inflammatory agent, or the extract has a synergistic anti-cancer activity with an anti-cancer agent.

10. The turmeric oil extract of any of paragraphs 1-9, wherein the extract enhances anti-inflammatory activity of an anti-inflammatory agent or the extract enhances anti-cancer activity of an anti-cancer agent.

11. A curcumin derivative having the structure of formula (I):

Formula (I)

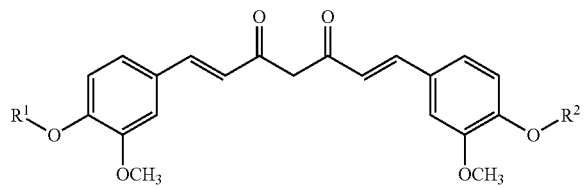

wherein:
R$^1$ and R$^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)R$^3$, —C(O)OR$^3$, or —C(O)NR$^3$R$^3$, provided that at least one of R$^1$ and R$^2$ is not H;
R$^3$ is independently for each occurrence H, optionally substituted alkyl, optionally substituted alkenyl, optionally substituted alkynyl, optionally substituted cyclyl, optionally substituted heterocyclyl, optionally substituted aryl, optionally substituted heteroaryl; and analogs, derivatives, isomers, prodrugs, and pharmaceutically acceptable salts thereof.

12. The curcumin derivative of paragraph 11, wherein R$^1$ and R$^2$ are the same.

13. The curcumin derivative of paragraph 11, wherein one of R$^1$ and R$^2$ is H.

14. The curcumin derivative of any of paragraphs 11-13, wherein at least one of R$^1$ and R$^2$ is selected from the group consisting of acetyl, myristoleoyl, palmitoleoyl, sapienoyl, oleoyl, linoleoyl, α-linoleoyl, α-linolenoyl, γ-linolenoyl, arcchidionoyl, eicosapentaenoyl, erucoyl, docosahexaenoyl, lauroyl, myrsitoyl, palmitoyl, stearoyl, arachidoyl, behenoyl, lignoceroyl, certoyl and any combinations thereof.

15. The curcumin derivative of any of paragraphs 11-14, wherein at least one of R$^1$ and R$^2$ is —C(O)R$^3$ and R$^3$ is an optionally substituted aryl.

16. The curcumin derivative of paragraph 15, wherein the aryl is substituted at the 2-, 3-, 4-, or 5-position or any combinations of these positions.

17. The curcumin derivative of any of paragraphs 15-16, wherein the optionally substituted aryl is an optionally substituted phenyl 18. The curcumin derivative of any of paragraphs 11-17, wherein at least one of R$^1$ and R$^2$ is

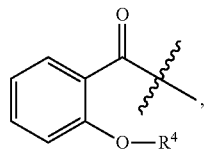

wherein R$^4$ is H, optionally substituted alkyl, optionally substituted alkenyl, optionally substituted alkynyl, or optionally substituted acyl.

19. The curcumin derivative of paragraph 18, wherein R$^4$ is H or C(O)CH$_3$.

20. The curcumin derivative of any of paragraphs 11-19, wherein at least one of R$^1$ and R$^2$ is -linker-R$^5$, wherein R$^5$ is H, a carbohydrate, a peptide, and analogs and derivatives thereof.

21. The curcumin derivative of paragraph 20, wherein the linker is —C(O)(CH$_2$)$_m$C(O)O—, wherein m is an integer from 1 to 10.

22. The curcumin derivative of paragraph 21, wherein m is 2 or 3

23. The curcumin derivative of any of paragraphs 20-22, wherein R$^5$ is H, a carbohydrate or a peptide.

24. The curcumin derivative of paragraph 11, wherein R$^1$ and R$^2$ both are not —C(O)CH$_3$.

25. The curcumin derivative of paragraph 11, wherein the curcumin derivative is di(acetylsalicyloyl)-curcumin monoacetylsalicyloyl-curcumin, diacetyl-curcumin, monoacetyl-curcumin, diaglutaroyl-curcumin, monoglutaroyl-curcumin, di-gluocose-glutaroyl-curcumin, mono-gluocose-glutaroyl-curcumin, monolinoleol-curcumnin, di-linoleoyl-curcumin and peptide-curcumin conjugates.

26. The curcumin derivative of any of paragraph 11-25, wherein the curcumin derivative is anti-inflammatory, anti-cancer, and/or analgesic.

27. The curcumin derivative of any of paragraph 11-26, wherein the curcumin derivative has synergistic anti-inflammatory activity and/or analgesic activity with an anti-inflammatory agent or the curcumin derivative has synergistic anti-cancer activity with an anti-cancer agent.

28. The curcumin derivative of any of paragraph 11-27, wherein the curcumin derivative enhances anti-inflammatory activity of an anti-inflammatory agent or the curcumin derivative enhances anti-cancer activity of an anti-cancer agent.

29. A composition comprising turmeric oil or a turmeric oil extract and a compound selected from the group consisting of an anti-cancer compound, an anti-inflammatory agent, a curcumin conjugate of any of paragraphs 11-28, fish oil, fish oil extract, a salicylic acid conjugate, a curcumin ether derivative, and any combinations thereof, wherein the salicylic acid is of formula (II):

Formula (II)

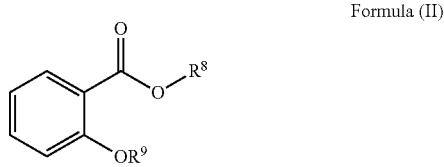

wherein R$^8$ is a carbohydrate; R$^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof,
and wherein the curcumin ether derivative is of formula (III):

Formula (III)

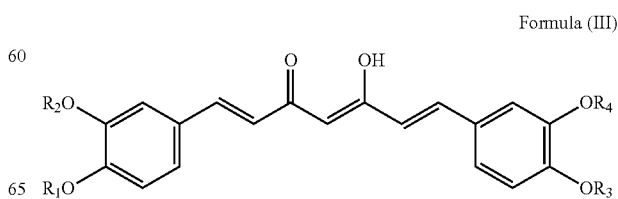

wherein $R_2$ and $R_4$ are both $CH_3$; and $R_1$ and $R_3$ are both alkyl or one of $R_1$ and $R_3$ is H and the other is alkyl.

30. The composition of paragraph 29, wherein the composition comprises at least two of: (a) an anti-cancer compound; (b) a curcumin derivative; (c) fish oil or fish oil extract; (e) a salicylic acid conjugate; and (f) a curcumin ether derivative.

31. The composition of paragraph 30, wherein the composition comprises salicylic conjugate and a curcumin derivative.

32. The composition of any of paragraphs 29-31, wherein the turmeric oil extract is an extract of any of paragraphs 1-10.

33. The composition of any of paragraphs 29-32, wherein $R^8$ is selected from the group consisting of glucose, glyceraldehydes, erythrose, threose, ribulose, xylulose, ribose, arabinose, deoxyribose, xylose, lyxose, psicose, fructose, sorbose, tagatose, allose, altrose, mannose, gulose, idose, galactose, talose, fucose, fuculose, rhamnose, sedoheptulose, octose, nonose (Neuraminic acid), and the like.

34. The composition of any of paragraphs 29-33, wherein $R^9$ is H or $C(O)CH_3$.

35. The composition of any of paragraphs 29-34, wherein the salicylic acid conjugate is of formula (IIb):

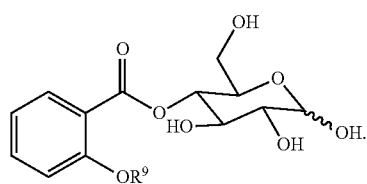

Formula (IIb)

36. The composition of any of paragraphs 29-35, wherein the anti-cancer agent is selected from the group consisting of paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; 2'-(GABA-succinoyl)paclitaxel, 2'-(glucose-GABA-succinoyl)paclitaxel, 2'-(glucose-succinoyl)paclitaxel, 2'-(glucose-glutamyl)paclitaxel, 2'-(glucosamide-GABA-succinoyl)paclitaxel, 2'-(glucoseamide-succinoyl)paclitaxel, 2'-(glucoseamide-glutamyl)paclitaxel, 7-(GABA-succinoyl)paclitaxel, 7-(glucose-GABA-succinoyl)paclitaxel, 7-(glucose-succinoyl)paclitaxel, 7-(glucose-glutamyl)paclitaxel, 7-(glucosamide-GABA-succinoyl)paclitaxel, 7-(glucoseamide-succinoyl)paclitaxel, and 7-(glucoseamide-glutamyl)paclitaxel; and any mixtures thereof.

37. The composition of any of paragraphs 29-36, wherein the anti-inflammatory agent is selected from the group consisting of 21-acetoxypregnenolone, alclometasone, algestone, amcinonide, beclometasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aspirin, sodium salicylate, choline magnesium trisalicylate, salicylate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, oxicams (piroxicam, meloxicam); alkanones such as nabumetone, refecoxib, celecoxib, etodolac, sulfonanilides, and derivatives thereof and mixtures thereof.

38. The composition of any of paragraphs 29-37, wherein the ratio of the turmeric oil or the turmeric oil extract and the compound is from about 99:1 to about 1:99.

39. The composition of any of paragraphs 29-38, wherein the composition comprises at least 50% turmeric oil and/or turmeric oil extract.

40. The composition of any of paragraphs 29-39, wherein the composition comprises turmeric oil extract and aspirin; turmeric oil extract and a curcumin derivative, turmeric oil extract and a salicylic acid conjugate; turmeric oil extract and di(acetylsalicyloyl)-curcumin; turmeric oil extract and monoacetylsalicyloyl-curcumin; turmeric oil extract and diacetyl-curcumin; turmeric oil extract and monoacetyl-curcumin; turmeric oil extract and diaglutaroyl-curcumin; turmeric oil extract and monoglutaroyl-curcumin; turmeric oil extract and di-gluocose-glutaroyl-curcumin; turmeric oil extract and mono-gluocose-glutaroyl-curcumin; turmeric oil extract and monolinoleol-curcumnin; turmeric oil extract and di-linoleoyl-curcumin; turmeric oil extract and an anticancer agent; turmeric oil extract and an anti-inflammatory agent; turmeric oil extract and fish oil; turmeric oil extract and fish oil extract; turmeric oil extract, an anti-cancer agent and an anti-inflammatory agent; turmeric oil extract, an anti-cancer agent and a curcumin derivative; turmeric oil extract, an anti-cancer agent and a salicylic acid conjugate; turmeric oil extract, an anti-inflammatory agent and a curcumin derivative; turmeric oil extract, an anti-inflammatory agent and a salicylic acid conjugate; or turmeric oil extract, a curcumin derivative and a salicylic acid conjugate.

41. A composition comprising a curcumin derivative of any of paragraphs 11-29 and a compound selected from the group consisting of an anti-cancer compound, an anti-inflammatory agent, fish oil, fish oil extract, a salicylic acid conjugate, a curcumin ether derivative, and any combinations thereo, wherein the salicylic acid conjugate is of formula (II):

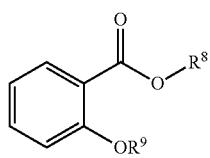

Formula (II)

wherein $R^8$ is a carbohydrate; $R^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof, and wherein the curcumin ether derivative is of formula (III):

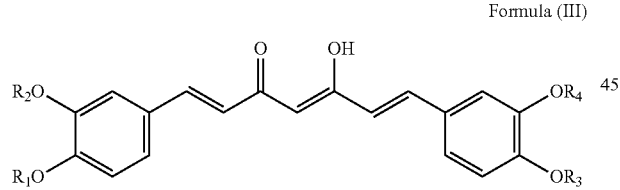

Formula (III)

wherein $R_2$ and $R_4$ are both $CH_3$; and $R_1$ and $R_3$ are both alkyl or one of $R_1$ and $R_3$ is H and the other is alkyl.

42. The composition of paragraph 41, wherein the composition comprises at least two of: (a) an anti-cancer compound; (b) fish oil or fish oil extract; (c) a salicylic acid conjugate; and (e) a curcumin ether derivative.

43. The composition of any of paragraphs 41-42, wherein $R^8$ is selected from the group consisting of glucose, glyceraldehydes, erythrose, threose, ribulose, xylulose, ribose, arabinose, deoxyribose, xylose, lyxose, psicose, fructose, sorbose, tagatose, allose, altrose, mannose, gulose, idose, galactose, talose, fucose, fuculose, rhamnose, sedoheptulose, octose, nonose (Neuraminic acid), and the like.

44. The composition of any of paragraphs 41-43, wherein $R^9$ is H or $C(O)CH_3$.

45. The composition of any of paragraphs 41-44, wherein the salicylic acid conjugate is of formula (IIb):

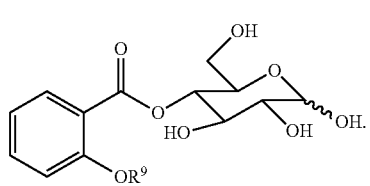

Formula (IIb)

46. The composition of any of paragraphs 41-45, wherein the anti-cancer agent is selected from the group consisting of paclitaxel (taxol); docetaxal; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof.

47. The composition of any of paragraphs 41-46, wherein the anti-inflammatory agent is selected from the group consisting of 21-acetoxypregnenolone, alclometasone, algestone, amcinonide, beclomethasone, betamethasone, budesonide, chloroprednisone, clobetasol, clobetansone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furcate, paramethosone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, aspirin, sodium salicylate, choline magnesium trisalicylate, salicylate, diflunisal, sulfasalazine, olsalazine, acetaminophen, indomethacin, sulindac, tolmetin, dicofenac, ketorolac, ibuprofen, naproxen, flurbiprofen, ketoprofen, fenoprofen, oxaprozin, mefenamic acid, meloxicam, oxicams (piroxicam, meloxicam); alkanones such as nabumetone, refecoxib, celecoxib, etodolac, sulfonanilides, and derivatives thereof and mixtures thereof.

48. The composition of any of paragraphs 41-47, wherein the ratio of curcumin derivative and the compound is from about 99:1 to about 1:99.

49. The composition of any of paragraphs 41-48, wherein the composition comprises at least 50% the curcumin derivative 50. The composition of any of paragraphs 41-49, wherein the composition comprises a curcumin derivative and aspirin; a curcumin derivative and a salicylic acid conjugate; a curcumin derivative and curcumin; aspirin and di(acetylsalicyloyl)-curcumin; aspirin and monoacetylsalicyloyl-curcumin; aspirin and diacetyl-curcumin; aspirin and monoacetyl-curcumin; aspirin and diaglutaroyl-curcumin; aspirin and monoglutaroyl-curcumin; aspirin and di-gluocose-glutaroyl-curcumin; aspirin and mono-gluocose-glutaroyl-curcumin; aspirin and monolinoleol-curcumnin; aspirin and di-linoleoyl-curcumin; a salicylic acid conjugate and di(acetylsalicyloyl)-curcumin; a salicylic acid conjugate and monoacetylsalicyloyl-curcumin; a salicylic acid conjugate and diacetyl-curcumin; a salicylic acid conjugate and monoacetyl-curcumin; salicylic acid conjugate and diaglutaroyl-curcumin; salicylic acid conjugate and monoglutaroyl-curcumin; salicylic acid conjugate and di-gluocose-glutaroyl-curcumin; a salicylic acid conjugate and mono-gluocose-glutaroyl-curcumin; salicylic acid conjugate and monolinoleol-curcumnin; or salicylic acid conjugate and di-linoleoyl-curcumin.

51. A pharmaceutical composition comprising a turmeric oil extract of any of paragraphs 1-10, a curcumin derivative of any of paragraphs 11-28, or a composition of any of paragraphs 29-50, and a pharmaceutically acceptable carrier or excipient.

52. A method of treating inflammation or an inflammatory disease or condition in a subject, the method comprising: administering a therapeutically effective amount of a turmeric oil extract of any of paragraphs 1-10, a curcumin derivative of any of paragraphs 11-29, a composition of any paragraphs 29-50, a pharmaceutical composition of paragraph 51, a salicylic acid conjugate, a curcumin ether derivative to a subject in need thereof, wherein the salicylic acid conjugate is of formula (II):

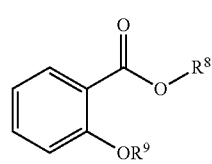

Formula (II)

wherein $R^8$ is a carbohydrate; $R^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof, and wherein the curcumin ether derivative is of formula (III):

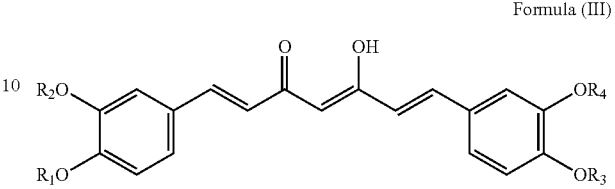

Formula (III)

wherein $R_2$ and $R_4$ are both $CH_3$; and $R_1$ and $R_3$ are both alkyl or one of $R_1$ and $R_3$ is H and the other is alkyl.

53. The method of paragraph 52, wherein the inflammatory disease or condition is an inflammatory or allergic disease, an autoimmune disease, a graft rejection, or another disease in which undesired inflammatory responses needs to be inhibited.

54. The method of any of paragraphs 52-53, further comprising a step of diagnosing a subject as having an inflammatory disease before onset of said administration.

55. The method of paragraph 52, wherein the subject has been previously diagnosed with inflammation, inflammatory disease or condition.

56. The method of paragraph 55, the method further comprising a step of selecting a subject who has inflammation, inflammatory disease or condition before onset of said administration.

57. The method of any of paragraphs 52, wherein the subject is undergoing treatment for inflammation or inflammatory disease or condition before onset of said administration.

58. The method of any of paragraphs 52-57, wherein the subject is a mammal.

59. The method of any of paragraphs 52-58, wherein the subject is human.

60. The method of any of paragraphs 52-59, wherein the therapeutically effective amount is 1 µg/kg to 150 mg/kg of body weight of the subject.

61. The method of any of paragraphs 52-60, wherein said administration is daily, every third day, every fourth day, every fifth day, once-a-week, once-two-weeks, or once-a-month.

62. A method of treating cancer or metastasis in a subject, the method comprising: administering a therapeutically effective amount of a turmeric oil extract of any of paragraphs 1-10, a curcumin derivative of any of paragraphs 11-29, a composition of any paragraphs 29-50, a pharmaceutical composition of paragraph 51, a salicylic acid conjugate, or a curcumin ether derivative to a subject in need thereof, wherein the salicylic acid conjugate is of formula (II):

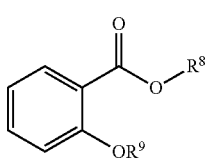

Formula (II)

wherein $R^8$ is a carbohydrate; $R^9$ is H, optionally substituted alkyl, optionally substituted alkenyl, optionally substituted alkynyl, or optionally substituted acyl; and analogs, derivatives, isomers, prodrugs, and pharmaceutically acceptable salts thereof,
and wherein the curcumin ether derivative is of formula (III):

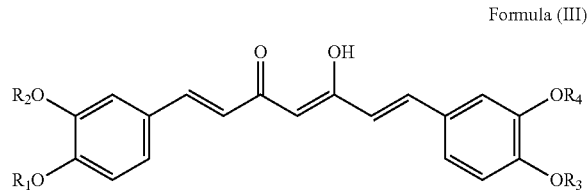

Formula (III)

wherein $R_2$ and $R_4$ are both $CH_3$; and $R_1$ and $R_3$ are both alkyl or one of $R_1$ and $R_3$ is H and the other is alkyl.

63. The method of paragraph 62, wherein the cancer is selected from the group consisting of adenocarcinoma, lymphoma, blastoma, melanoma, sarcoma, leukemia, squamous cell cancer, small-cell lung cancer, non-small cell lung cancer, gastrointestinal cancer, Hodgkin's and nonHodgkin's lymphoma, pancreatic cancer, glioblastoma, cervical cancer, ovarian cancer, liver cancer, bladder cancer, breast cancer, colon cancer, colorectal cancer, endometrial carcinoma, salivary gland carcinoma, kidney cancer, basal cell carcinoma, melanoma, prostate cancer, vulval cancer, thyroid cancer, testicular cancer, esophageal cancer, head cancer, and neck cancer.

64. The method of any of paragraphs 62-63, further comprising a step of diagnosing a subject as having cancer before onset of said administration.

65. The method of paragraph 62, wherein the subject has been previously diagnosed with cancer.

66. The method of paragraph 65, the method further comprising a step of selecting a subject who has cancer before onset of said administration.

67. The method of any of paragraphs 62, wherein the subject is undergoing treatment for cancer before onset of said administration.

68. The method of any of paragraphs 62-67, wherein the subject is a mammal.

69. The method of any of paragraphs 62-68, wherein the subject is human.

70. The method of any of paragraphs 62-69, wherein the therapeutically effective amount is 1 µg/kg to 150 mg/kg of body weight of the subject.

71. The method of any of paragraphs 62-70, wherein said administration is daily, every third day, every fourth day, every fifth day, once-a-week, once-two-weeks, or once-a-month.

To the extent not already indicated, it will be understood by those of ordinary skill in the art that any one of the various embodiments herein described and illustrated can be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1

Extraction and Purification of Turmeric Oil

Turmeric Oil Extraction:
Turmeric powder obtained from fresh turmeric roots (95 grams) was taken in a Whatman filter paper pouch, stirred with 1.2 L of hexane 24 hours and the solvent was concentrated to get a red oil, 5.2 grams. The residue in pouch was stirred over night with 500 mL of hexane and concentrated to get 0.5 g. The combined yield, 5.7 grams.

Turmeric Oil Purification by Successive High Vacuum Distillations:
First Distillation of 5.7 g of crude extract under high vacuum (<1 torr) gave a fraction, 3.54 g at 115 to 135° C., and an un-distilled portion. Second distillation of 3.54 g of distilled product under high vacuum (<1 torr) gave 3.10 g of oil. Third distillation gave 2.64 grams at 100-111° C. (<1.00 torr). Fourth distillation gave three fractions: (1) 0.57 g of material at 100-120° C. (<1.00 torr) (also referred to as NJ-78-11 herein); (2) 1.20 g of material at 120-123° C. (<1.00 torr) (also referred to as NJ-78-12 herein); and (3) 0.26 g at 124° C. (<1.00 torr) (also referred to as NJ-78-13 herein). In some embodiments, a turmeric oil extract described herein corresponds to the NJ-78-12 fraction.

Column Chromatography Purification of Distilled Turmeric Oil:
In some experiment, fractions NJ-78-11 and NJ-78-13 from different distillations were combined together and purified by column chromatography. In one experiment, ~8.0 grams of combined NJ-78-12 and NJ-78-13 mixture were purified on a silica gel (150 grams) column and fractions shown in Table 1 were obtained. Based on GC-MS and NMR, NJ-78-12 fraction, consisted of ar-turmerone (53.19%), α-turmerone (38.30%), β-turmerone (8.72%). NJ-78-12: HPLC: (RT, min) 2.39, 2.86, 3.62, 4.26; NMR: $CDCl_3$ (δ) 0.93 m, 3H, 1.26-1.32 m, 2.5H, 1.89 s, 3H, 1.96 s, 3H, 2.03-2.22 m, 8H, 2.24-2.50 m, 2H, 3.3 m, 0.02H, 4.75 bs, bs, 5.6-5.75 m, 5.80-5.82 d, 6.04 s, 6.08 s, 6.2 d, 7.12 s. GC-MS, RT: 9.79 (216, 132, 119, 105, 91) 10.20 (216, 201, 132, 119, 91, 83), 10.45 (218, 120, 105, 91, 83), 10.78 (218, 135, 123, 107, 91, 83)

Fractions MT-133-1 and MT-133-3 showed one single compound on TLC. The MT-133-1 fractions showed a single compound with an $R_f$ of 0.67 by TLC (ethyl acetate/hexane 15/85) and the fraction MT-133-3 showed a single compound with an $R_f$ of 0.42 by TLC. Accordingly, in some embodiments, a turmeric oil extract of the invention corresponds to fraction MT-133-1 and/or MT-133-3.

Based on NMR and GC-MS, MT-133-3 consists of α-turmerone (77.78%), β-turmerone (20.37%) and ar-turmerone (1.85%); TLC (ethyl acetate/hexane; 15/85) Rf=0.42; HPLC (RT, min) 3.41; Elemental analysis C, 73.86%; H 8.79%; NMR: $CDCl_3$ (δ) 0.91, t, J=6.16 Hz) 8H, 1.73 s, 1.91, s, 2.21-2.29, 2.55, 4.78 d (J=6.4 Hz), 5.46, s, 5.6-5.8, m, 5.82, d, J=9.7 Hz), 6.07, d, J=1.1 Hz), 6.17-6.20, m, 7.29, s. GC-MS, RT (m/z): 10.20 (218, 119, 105, 83), 10.43 (218, 120, 105, 91, 83)

TABLE 1

Purification of distilled turmeric oil

| Eluting solvent | Volume | Fractions | Quantity |
|---|---|---|---|
| Hexane | 1 L | MT-133-1 | 0.14 g |
|  |  | MT-133-2 | 0.04 g |
| 0.5% Ethyl acetate, Hexane | 1 L | — | — |
| 1% Ethyl acetate, Hexane | 1 L | MT-133-3 | 2.44 g |
|  |  | MT-133-4 | 1.86 g |
| 2% Ethyl acetate, Hexane | 2 L | MT-133-5 | 0.82 g |
|  |  | MT-133-6 | 0.22 g |
|  |  | MT-133-7 | 0.04 g |
| 5% Ethyl acetate, Hexane | 1 L | MT-133-8 | 0.10 g |
|  |  | MT-133-9 | 0.06 g |
| Methanol | 250 ml | MT-133-10 | 1.32 g |
| Total obtained from column |  |  | 7.04 g |

Example 2

Curcumin Derivatives

Curcumin Acetate:

A mixture of curcumin (1.0 g), acetic anhydride (20 ml) and pyridine (2 ml) were heated at 70° C. with stirring for 40 minutes and 80° C. for 1 hour and at 60° C. over night under dry conditions. The mixture was cooled to room temperature, added to 50 mL of ice coldwater. The mixture was extracted with chloroform (3×40 mL). The organic layer was stirred with 5% sodium bicarbonate solution for 0.5 hour. The organic layer was separated and washed with 1N HCl (2×50 mL), brine (2×40 mL), dried (anhydrous $Na_2SO_4$), concentrated under reduced pressure to get yellow solid, 1.1 g. TLC indicated no curcumin present. Column purification: The product (0.35 g) was purified on 25 grams of silica gel column eluting with 10% ethyl acetate and hexane. Yield, 0.34 g; NMR consistent with structure.

Glutaric Ester of Curcumin:

Curcumin (1.00 g) was dissolved in tetrahydrofuran (50 ml) in a 250 mL round bottom flask under a flow of nitrogen gas. Dimethyl amino pyridine (56 mg) and triethyl amine (1.33 ml) were added. The color changed from yellow to light red. Glutaric anhydride (50 ml) was dissolved in 5 mL of tetrahydrofuran and added in drops using a pressure equalizing addition funnel. The mixture was refluxed and stirred over night. The mixture was cooled and concentrated. 50 mL of ethyl acetate was added, cooled with ice, 20 mL of 0.5 N HCl was added. The organic layer was separated and washed with brine. The brine was combined with the HCl wash, and the combined solution was extracted with 25 mL of ethyl acetate. The combined ethyl acetate layers were dried over anhydrous sodium sulfate, filtered, concentrated under vacuum to get 1.30 g. TLC indicated no curcumin, NMR consistent with structure.

Curcumin-Acetylsalicylate:

Acetyl salicylic acid (1.0 g) was mixed with thionyl chloride (1.0 mL) and mixture was heated in a 50 mL round bottom flask under nitrogen at 80° C. for 1 hour. The excess thionyl chloride was removed by distillation, dried in high vacuum to get acetyl salicyloyl chloride as a viscous liquid, ~1.1 g. Used for next step with out further purification. Curcumin (0.50 g) was taken in 10 mL of DMF in a 50 mL round bottom flask under nitrogen and pyridine was added. Acetyl salicyloyl chloride (~1.1 g) was taken in 5 mL of DMF and was added drop wise from a pressure equalizing separating funnel. The solution turned darker in color. The mixture was heated at 90° C. for 1 hour and then at room temperature overnight. To the reaction mixture 100 mL of water was added. A solid formed which was filtered, the solid was stirred with 30 mL of $NaHCO_3$ solution. The solid was filtered, washed with water, dried under high vacuum to yield 1.10 g of the product, curcumin acetyl salicylate or curcumin-aspirin, NMR was consistent with the structure.

Curcumin-Glutarate:

In a 500 mL round bottom flask curcumin (3.00 g), DMAP (168 mg) and triethyl amine (4 ml) were taken in 150 mL of THF. Glutaric anhydride (2.35 ml) in 15 mL of THF was added drop-wise under anhydrous conditions. The mixture was refluxed for 20 hours at 80° C. The solution was evaporated in a rotovop. The thick residue was taken in 150 mL of ethyl acetate, washed with 50 mL of 0.5 N HCl. The HCl wash was extracted with 50 mL of ethyl acetate. The combined ethyl acetate extracts were dried over anhydrous sodium sulfate and was concentrated under vacuum to get 4.80 g. This was co-evaporated with ether several times to get a solid, 2.5 g. NMR was consistent with the structure.

Curcumin Diacetone Glucose-Glutarate:

A mixture of curcuminglutarate (0.50 g), diacetoneglucose (0.60 g), dicyclohexylcarbodiimide (50 mg), and ethyl acetate (50 mL) was stirred 19 hours at 25° C. The solution was filtered, washed with 0.5 N HCl (30 mL), 5% $NaHCO_3$ solution (30 mL), brine (30 mL), dried (anhydrous $Na_2SO_4$), concentrated under vacuum 1.10 g.

Curcumin Glucose Glutarate:

A mixture of Curcumin Diacetone-glucose glutarate (0.44 g) and acetic anhydride, 70% (25 ml) was refluxed for 2 hours, concentrated, dissolved in 50% methanol, water, filtered concentrated, 0.16 g. The solid was treated with 25 mL, 70% acetic acid, heated at 70° C. to 80° C. for 20 hours, concentrated and dried in high vacuum, 0.20 g.

Glyceryl Lipid Conjugates of Curcumin:

Curcumin may be conjugated to glyceryl lipids through a linking group such as succinoyl or glutaryl group. Such conjugates would be expected to facilitate the uptake of the drug through the lipid bilayer of cell membranes. The mono or di-lipid conjugates can be obtained by controlling the molar ratios of curcumin, the linking compounds and the glyceryl lipids. The glyceryl lipids may include glycerol with one or two fatty acids attached with ester bonds or fatty alkyl groups with ether linkage. Different fatty acids may be used for the glyceryl lipids. This can include saturated as well as mono and poly unsaturated fatty acids. The unsaturated fatty acids can include omega three fatty acids. The following scheme illustrates the synthesis method.

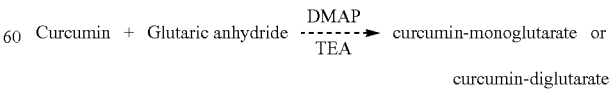

DMAP: Dimehtylamino pyridine; TEA: Triethylamine

Curcumin mono or diglutarate can be obtained by controlling the anhydride ratio (one or two equivalents respectively).

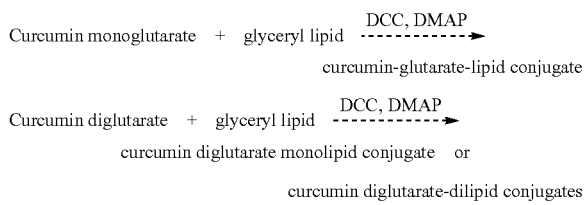

The mono- and di-lipid conjugate ratio can be controlled by using one or two equivalents of the glyceryl lipids respectively.

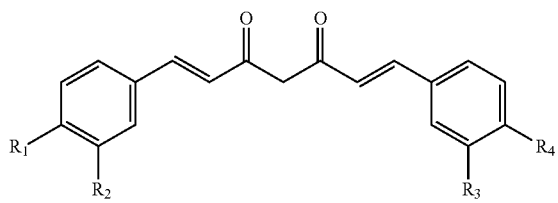

1. $R_1, R_4 = OH; R_2, R_3 = OCH_3$ or H curcumins
2. $R_1 = H, R_4 = OCO(CH_2)_3COOH$ monoglutaroyl curcumin
3. $R_1 = R_4 = OCO(CH_2)_3COOH$ diglutaroyl curcumin
4. $R_1 = H, R_4 = OCO(CH_2)_3COO-R_5$  $R_5 =$ glyceryl lipid
   $-O-CH_2-CH(OR_6)-CH_2(OR_6)$
5. $R_1 = OCO(CH_2)_3COOH, R_4 = OCO(CH_2)_3COO-R_5$
$R_6 =$ fatty acid chain or long alkyl chain Curcumin-Diglutarate-Distearin Monoester Conjugate:

A mixture of curcumin diglutarate (115 mg, 0.18 mmoles), distearin (113 mg, 0.18 mmoles), dicyclohexylcarbodiimide (54 mg, 0.18 mmoles), dimethylaminopyridine (14 mg), ethylacetate (10 mL) and dichloromethane (15 mL) was taken in a 50 mL round bottom flask, the solvents were anhydrous (dried over molecular sieves), and the mixture was stirred overnight. The yellow solution was concentrated and was purified on a silica gel column eluting with ethyl acetate-hexane (0 to 100% ethyl acetate). Yield, 119 mg. NMR confirmed the structure.

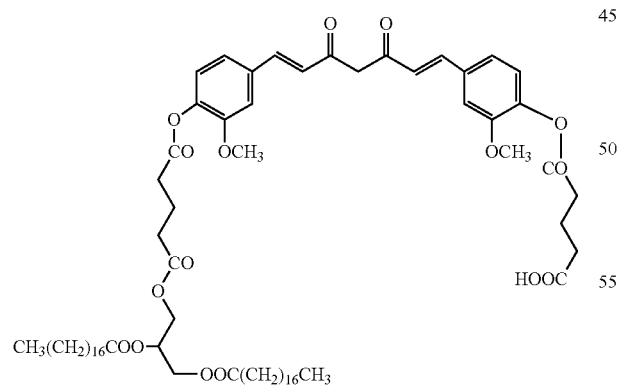

Example 3

Aspirin-Glucose Conjugate

Aspirin, is a widely used and relatively safe non-steroidal anti-inflammatory drug (NSAID), and it has been used for over hundred years. The main uses of aspirin can be summarized as an analgesic, antipyretic, anti-rheumatic agent and anti-inflammatory agent, may be used to prevent stroke, to prevent heart attack and to prevent cancer, may be used to treat AIDS and to treat problems associated with diabetes (Fowler). Aspirin is a non-selective cyclooxygenase inhibitor. Cyclooxygenase derived prostaglandins are involved in inflammatory activity. Prostaglasndins also are involved in gastrointestinal protection and vascular homeostasis. Aspirin acetylates Ser530 hydroxyl group in the COX binding site of COX-1 and COX-2. Aspirin is a much stronger inhibitor of COX-1 than of COX-2. See for example, Mead, E. A., Smith, W. L. & DeWitt, d. L., *J. Biol Chem.*, 1993, 268, 6610-6614 and Yeomans, N. D., *J Gastroenterol Hepatol.* 2010 Nov. 10. doi: 10.1111/j.1440-1746.2010.06569.x. [Epub ahead of print], content of both of which is herein incorporated by reference in its entirety. Aspirin is not very water soluble, only 0.33 g in 100 mL. Some of the undesirable side effects of aspirin results from undissolved particles in the gastrointestinal mucosa casing ulcers and bleeding. The solubility can be increased considerably by conjugating aspirin to glucose molecule through a systematic approach on a specified carbon of glucose.

Synthesis of Glucose-Aspirin:

A glucose-aspirin conjugate was synthesized as shown below.

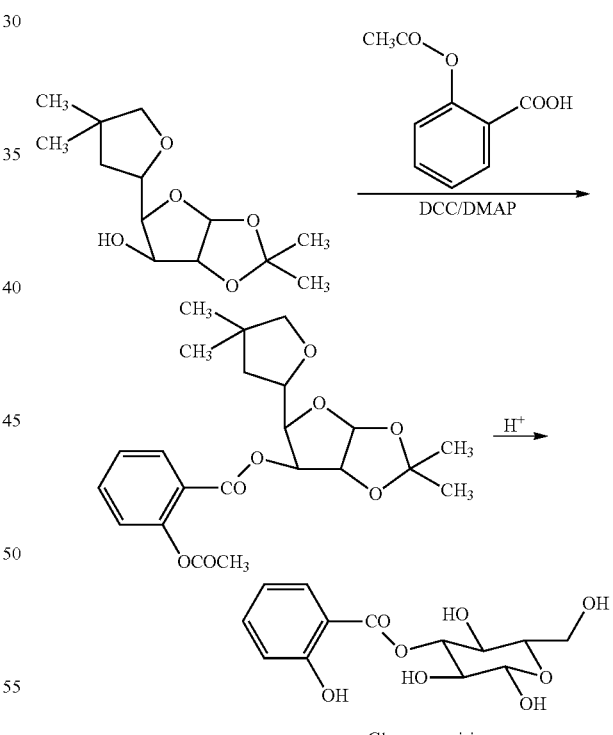

Glucose aspirin

DCC: Dicyclohexyl carbodiimide
DMAP: Dimethylaminopyridine

Hydroxyl protected glucose, 1,2:5,6-diisopropylglucose, was treated with aspirin in presence of dicyclohexylcarbodiimide (DCC) to form the acetyl salicylic acid ester on the fourth carbon of glucose. This ester was treated with acetic acid to remove the acetonide protecting groups to obtain glucose acetyl salysilate (glucose aspirin).

Synthesis of 1,2:5,6-di-O-isopropylidende-3-(2'-acetyloxybenzoyl)-D-glucose

Acetylsalicylic acid (12 g, 0.07 moles) was dissolved in 300 mL of ethyl acetate in a 1 liter round bottom flask fitted with anhydrous calcium chloride guard tube. Dicyclohexylcarbodiimide (8.24 g, 0.04 moles) was added to it resulting in the formation of a white precipitate. Diacetone-D-glucose (10 g, 0.04 moles) was added along with dimethylaminopyridine (4.88 g, 0.04 moles). The mixture was stirred for 3 hours at room temperature. The solid byproduct, dicyclohexyl urea, was removed by filtration. The filtrate was washed with 10% potassium carbonate (2×300 mL), 10% hydrochloric acid (2×300 mL) and with brine (300 mL). The ethylacetate solution was dried over anhydrous sodium sulfate and concentrated to get 17.8 g. The crude product, diacetone glucose salicylate (compound 3, scheme 1), was purified over silica gel column to get 8.98 g of product. NMR (CDCl$_3$, δ): 8.0 (dd, 1H), 7.6 (m, 1H), 7.33 (m, 1H), 7.13 (dd 1H), 5.9 (m, 1H), 5.4 (d, 1H), 4.61 (d, 1H), 4.20-4.37 (m, 2H), 4.03-4.15 (m, 2H), 2.37 (s, 3H), 1.28, 1.32, 1.41, 1.62 (our singlets, 12H).

Synthesis of 3-(2'-Acetyloxybenzoyl)-D-glucose (Glucose-3-aspirin)

A mixture of diacetone glucose salicylate (7.6 g) and 70% acetic acid (150 mL) was taken in a 500 mL round bottom flask. The mixture was refluxed for 2 hours under argon. The mixture formed a clean solution and it was concentrated under reduced pressure and dried under high vacuum. Column purification (silica gel, methylene chloride/methanol) yielded the product, glucose-3-aspirin (compound 5) as a white solid, 1.3 g. NMR (CDCl$_3$, δ): 10.6 (s, 1H), 7.9-8.1 9 m, 1H), 7.5 (m, 1H), 6.8-7.2 (m, 2H), 5.3 (m, 2H), 4.2-4.6 (m, 2H), 3.6-3.8 (m, 2H), 3.0-3.2 (m, 1H), 3.43 (bs, 3H), 1.65 (bs, 3H).

Elemental analysis: $C_{15}H_{18}O_9$, Calculated: C, 52.63; H, 5.30 Found: C, 52.51; H, 5.42. Mass: M+1, m/z 343.0999 (M+H calculated formula: $C_{15}H_{19}O_9$. Solubility of glucose-3-aspirin in water: 2.32 g/100 mL, Aspirin solubility: 0.33 g/100 mL (1 g in 300 mL water at 25° C.) (Merck Index, pp. 134, vol. 11, 1989). Thus, the aspirin-glucose conjugate was 700 times more soluble than aspirin.

Example 4

In Vitro Enzyme Hydrolysis of Glucose Aspirin Conjugate

A 25% solution of human serum in 0.01M phosphate buffer was taken and the test compound (glucose aspirin or aspirin) were added to get a concentration of 0.2 mg/mL. The hydrolysis for the rate of release of salicylic acid and the rate of decomposition of the test compound were measured by HPLC. As shown in Tables 2 and 3, glucose aspirin hydrolysed at a much slower rate than aspirin in human serum.

TABLE 2

In vitro enzyme hydrolysis of salicylic acid vs glucose-aspirin conjugate

| Time (min) | Salicyclic acid | | Glucose-aspirin | |
|---|---|---|---|---|
| | Concentration (M) | Rate (M/min) | Concentration (M) | Rate (M/min) |
| 0 | 0 | 0.00E+00 | 1.98E−04 | 0.00E+00 |
| 30 | 0.00E+00 | 0.00E+00 | 2.03E−04 | 1.91E−07 |
| 60 | 2.70E−06 | 4.50E−0.8 | 1.84E−04 | −2.24E−07 |
| 90 | 2.75E−06 | 3.06E−0.8 | 1.65E−04 | −3.62E−07 |
| 120 | 1.09E−05 | 9.11E−07 | 1.62E−04 | −2.96E−07 |
| 180 | 3.54E−05 | 1.97E−07 | 1.19E−04 | −4.38E−07 |
| Average rate: | | 9.08E−08 | | −3.30E−07 |
| Std. dev. | | 7.51E−08 | | 2.46E−07 |

TABLE 3

In vitro enzyme hydrolysis of salicylic acid vs acetylsalicyclic acid

| Time (min) | Salicyclic acid | | Acetylsalicyclic acid | |
|---|---|---|---|---|
| | Concentration (M) | Rate (M/min) | Concentration (M) | Rate (M/min) |
| 0 | 0 | 0.00E+00 | 4.57E−04 | 0.00E+00 |
| 30 | 1.95E−05 | 6.49E−07 | 4.15E−04 | −1.40E−06 |
| 60 | 3.39E−05 | 5.65E−07 | 3.99E−04 | −9.81E−07 |
| 90 | 4.98E−05 | 5.53E−07 | 2.48E−04 | −2.32E−06 |
| 120 | 7.49E−05 | 6.24E−07 | 2.70E−04 | −1.56E−06 |
| 180 | 1.07E−04 | 5.94E−07 | 1.74E−04 | −1.58E−06 |
| Average rate: | | 5.97E−07 | | −1.57E−06 |
| Std. dev. | | 3.17E−08 | | 4.85E−07 |

Example 5

Animal Studies with Glucose Aspirin Conjugates

Materials and Methods:

Animals were kept under 13 hour day night cycle. Animals were given standard diet and water was provided ad, libitum. All animals were acclimatized for at least one week before the experimental session. Animals were divided in to five groups. Each group consisted of 8 animals. Group 1 would get standard drug, aspirin at 100 mg/kg and group 2 was given aspirin 200 mg/kg i.p. Glucosyl acetyl salicylate was used in two dose levels. Group 3 was given the glucosyl acetyl salicylate at 100 mg/kg and group 4 was given this drug at 200 mg/kg i.p.

Carrageenan Induced Rat Paw Edema:

Pedal inflammation in albino rats of either sex was produced according to the method of Winter et al., (Proc Soc Exp Biol Med 1963; 111: 544-7). An injection was made with 0.1 ml of 1% carrageenan (SIGMA) suspension into the right hind foot of each rat in the plantar region. Groups 3 and 4 rats were treated intraperitoneally (i.p.) with glucosylacetyl salicylate 30 minutes before carrageenan injection. Control group 5 was given 0.5 ml saline and groups 1 and 2 received aspirin. Increase in linear paw circumference was measured by tying a piece of cotton thread round the rat's paw, and noting the point of intersection of two ends on a meter scale. This was taken as an index of increase in paw volume, which is a measure of oedema (Bamgbose S O A, Noamesi B K. Planta Med 1981; 42: 392-6). Measurements were taken immediately before and at 1, 2 and 3 hours after carrageenan injection. The inhibitory activity was calculated according to the following formula (Awe S O, Olajide O A, Adeboye J O, Makinde J M. Indian J Pharmacol 1998; 30: 38-42):

$$\text{Percent inhibition} = \frac{(Ct-Co)\text{ control} - (Ct-Co)\text{ treated}}{(Ct-Co)\text{ control}} \times 100$$

Ct-Linear paw circumference 3 hours after carrageenan injection and Co-Linear paw circumference before carrageenan injection.

Tail flick test: Analgesic activity was measured by the tail flick method, using the analgesiometer (Techno, Lucknow, India) as described by D'Armour and Smith (D'Armour F E, Smith D L. A method for determining loss of pain sensation. J Pharmacol Exp Ther 1941; 72: 74-9). Rats were screened for tail flip reaction with a cut-off time of 5 seconds. For each animal, the tail flick latency was obtained thrice before drug administration and mean was used as pre-drug latency. The tail flick latencies were measured at 0, 0.5, 1, 1.5, 2 and 3 h after administration chemicals. For animals that did not respond within the cut-off time of 10 seconds, the value of the cut-off time was considered as latency period for that animal (Ramabadran K, Bansinath M. A critical analysis of the experimental evaluation of nociceptive reactions in animals. Pharmaceutical Res 1986; 3: 263-70). Results was expressed as % maximum possible effect (MPE) (Bishnoi M, Patil C S, Kumar A, Kulkarni S K. Analgesic activity of acetyl-11-keto-beta-boswellic acid, a 5-lipoxygenase-enzyme inhibitor. Indian J Pharmacol 2005; 37: 255-56):

$$\% \, MPE = \frac{(\text{post treatment latency} - \text{pretreatment latency})}{\text{Pretreatment latency}} \times 100$$

Statistical analysis: Data was analyzed using analysis of variance (ANOVA), t-test, Mann-Whitney and Chi-square tests. $P<0.05$ was considered as statistically significant.

Figure 5:
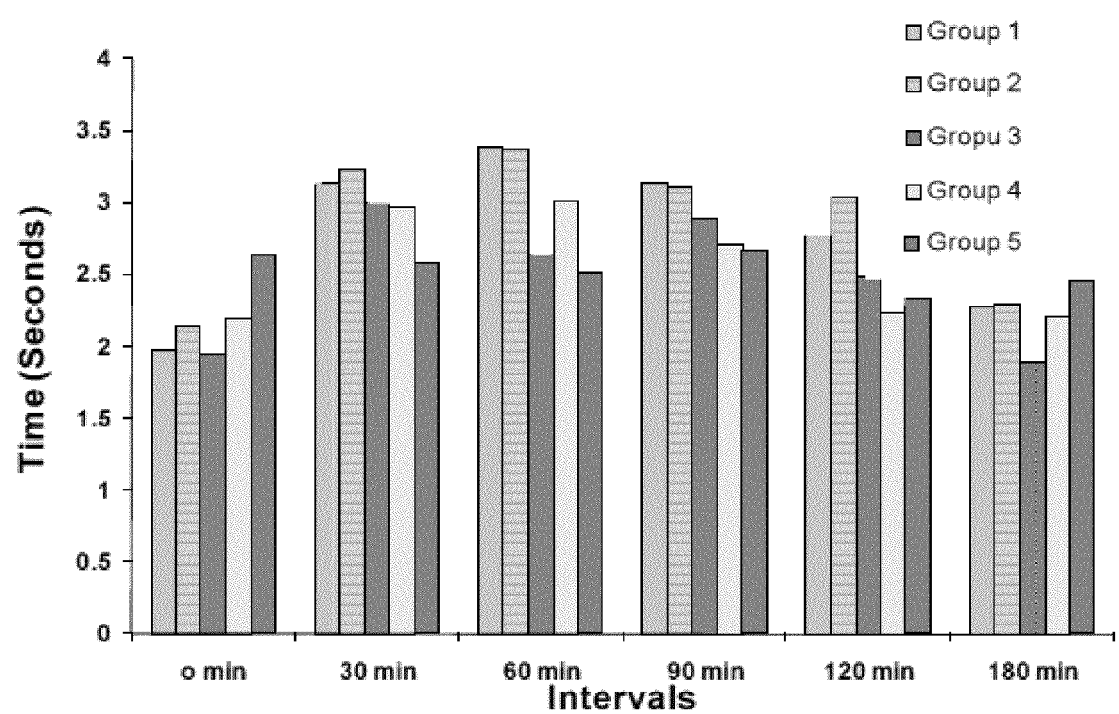
FIG. 5 is a bar graph showing tail flick latency (seconds) in aspirin and glucose-aspirin conjugated treated animals (n=8 in each group). Group 1=aspirin 100 mg/kg; Group 2=aspirin 200 mg/kg; Group 3=glucose-aspirin conjugate 100 mg/kg; Group 4=glucose-aspirin conjugate 200 mg/kg; and Group 5=control.

FIG. 5 shows the effect of drugs on tail flick latency in all groups. There was significant increase in the tail flick latency with the standard drug aspirin 100 mg/kg (Group1) and aspirin 200 mg/kg (Group 2) at all times intervals except 180 minutes as compared to control group (p<0.05). The increase was there till 120 minutes. There was no statistical significant change in the tail flick latency in the control group (Group 5). In test group there was significant increase in tail flick latency with both dose levels i.e. 100 mg/kg (Group 3) and 200 mg/kg (Group 4). The increase was there till 120 minutes in group 3 and 90 minutes in group 4. % MPE was more with 100 mg/kg as compared to 200 mg/kg.

Figure 6:
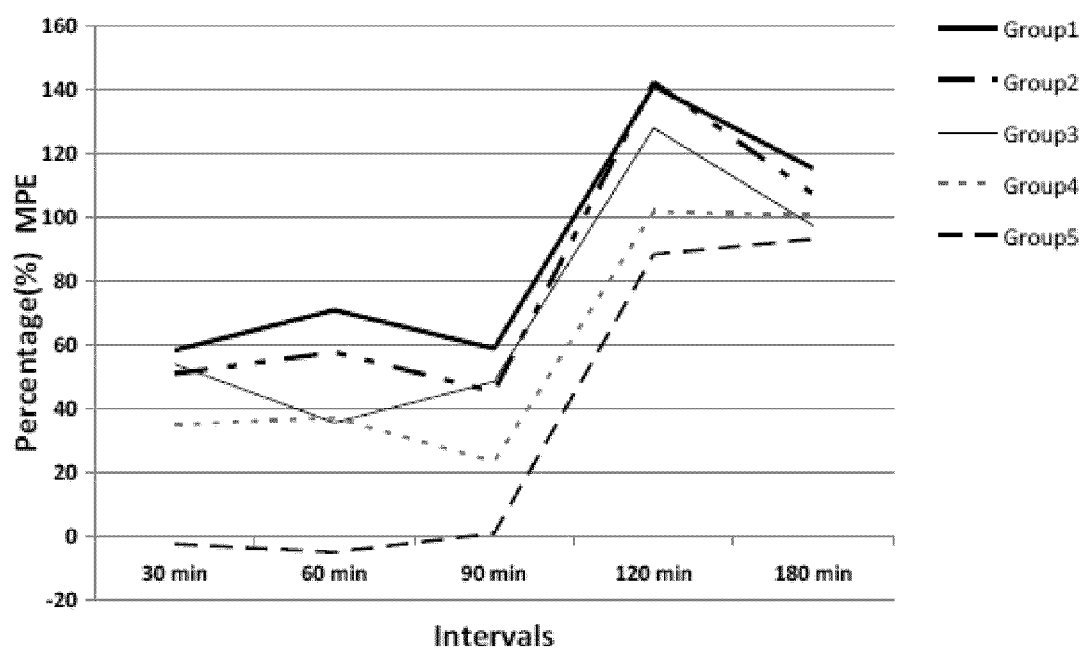
FIG. 6 is a line graph showing percentage of maximal possible effect (% MPE) in various groups (n=8 in each group). Groups are same as in FIG. 5.
Figure 7:
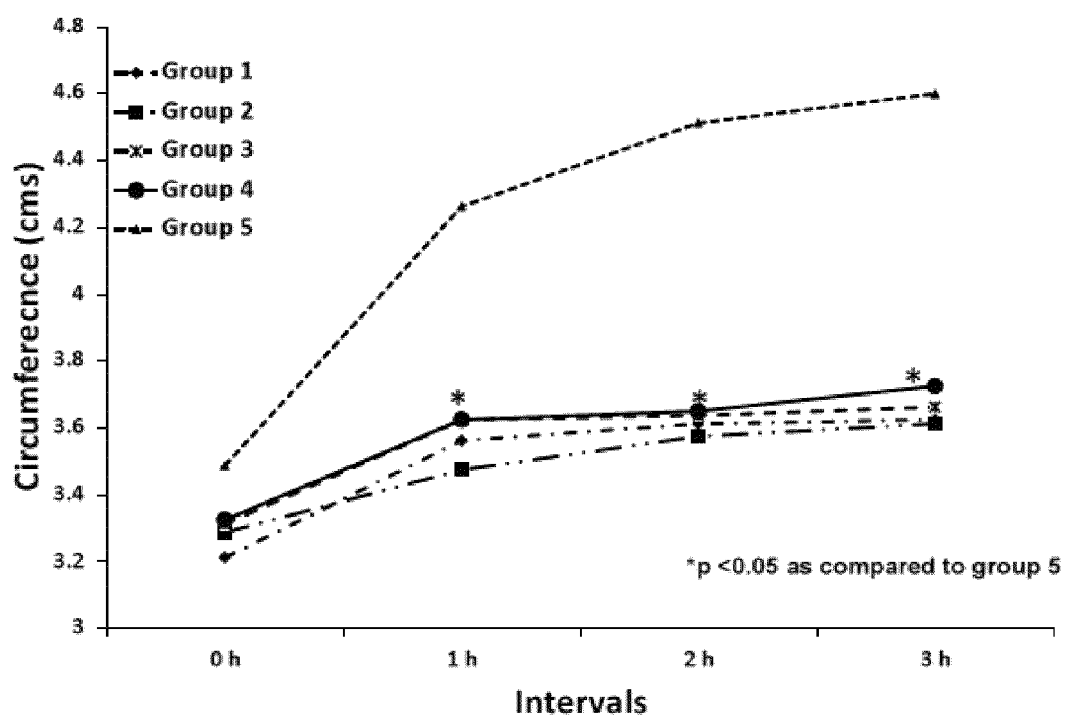
FIG. 7 is a line graph showing paw edema circumference (cm) in various groups. Groups are same as in FIG. 5.
Figure 8:
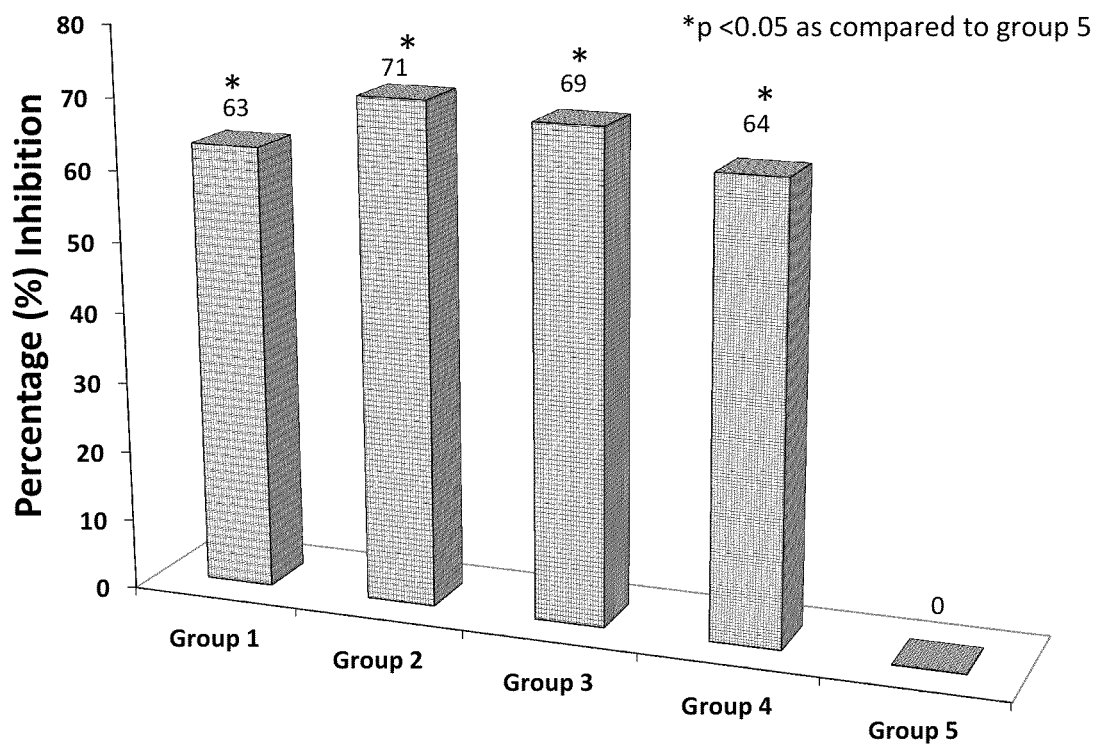
FIG. 8 is a bar graph showing percentage inhibition of paw edema in various groups (n=8 in each group). Groups are same as in FIG. 5.

Aspirin 100 mg/kg and 200 mg/kg significantly increased latency time as compared to control group (p<0.05) at 60 minutes. The latency time was significantly more at 60 minutes with both doses of aspirin as compared to 100 mg/kg dose of test compound (FIG. 5). Percentage (%) MPE was more with 100 mg/kg as compared to 200 mg/kg (FIG. 6). Percentage MPE was at peak at 120 minutes in all the groups. There was no statistically significant difference in the latency time with test compound as compared to control group.

These results demonstrate that Test compound in doses of 100 and 200 mg/kg significantly suppressed carrageenan-induced paw edema in rats and demonstrated significant analgesic activity in tail flick models.

Example 6

Animal Studies with Turmeric Oil Extracts

Anti-Inflammation and Analgesic Studies:

Albino rats obtained from central animal house of institute were used in the study. The animals were kept under 12 hour day night cycle. Animals were given standard diet and water was provided ad libitum. All animals were acclimatized for at least one week before the experimental session. Animals were divided into twelve groups in the carrageenan induced paw edema and tail flick method. Each group consisted of 4 animal each. The groups received various chemicals as given in Table 4.

TABLE 4

Chemicals and dosage given to the various animal groups

| Group # | Chemical Given[a] | Dos/volume |
|---|---|---|
| 0 | DMSO | 0.3 ml |
| 1 | NJ1 | 50 mg/kg |
| 2 | NJ1 | 100 mg/kg |
| 3 | NJ1 | 200 mg/kg |
| 4 | NJ2 | 50 mg/kg |
| 5 | NJ2 | 100 mg/kg |
| 6 | NJ2 | 200 mg/kg |
| 7 | NJ3 | 50 mg/kg |
| 8 | NJ3 | 100 mg/kg |
| 9 | NJ3 | 200 mg/kg |
| 10 | Aspirin | 100 mg/kg |
| 11 | Aspirin | 200 mg/kg |
| 12 | Normal Saline | 0.3 ml |

[a]NJ1 = turmeric oil distillate 115° C.-120° C./high vacuum (~100 torr), NJ2 = Omega-3, DHA/EPA – fish oil, and NJ3 = NJ1 + NJ2 (1:1)

Figure 9:
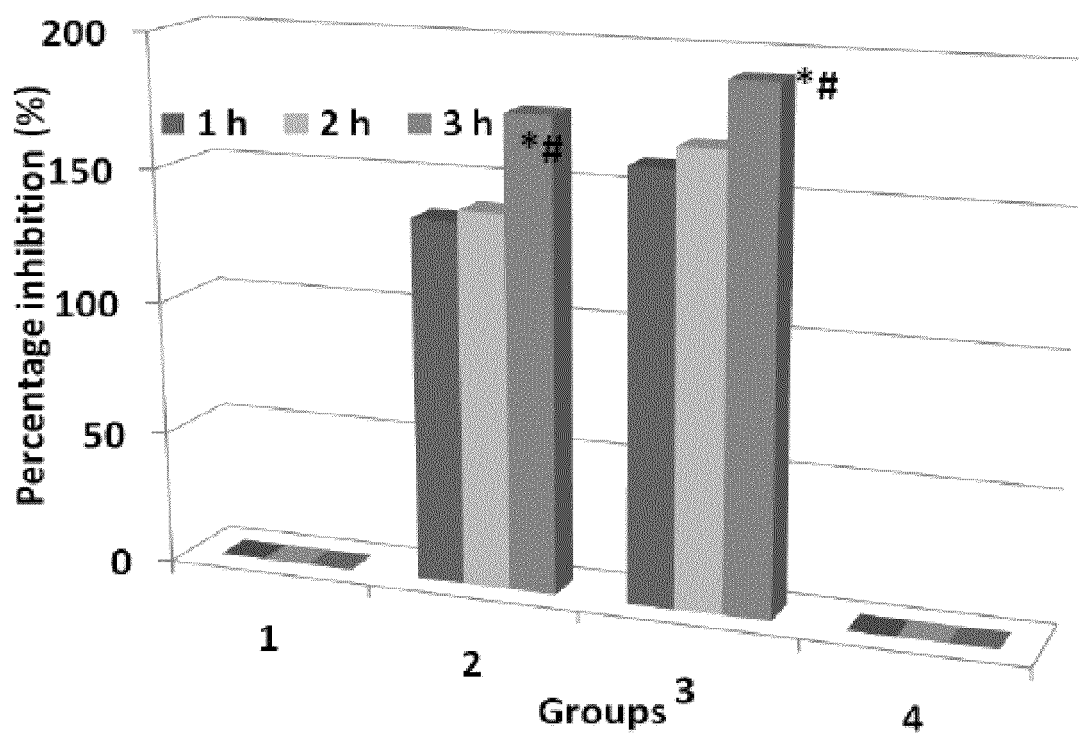
FIG. 9 is a bar graph showing percentage inhibition of paw edema with controls. Group 1=DMSO; Group 2=aspirin 100 mg/kg; Group 3=aspirin 200 mg/kg; Group 4=normal saline. *P<0.05 as compared to Group 1; #P<0.05 as compared to Group 4 is a bar graph showing percentage inhibition of paw edema with controls.
Figure 10:
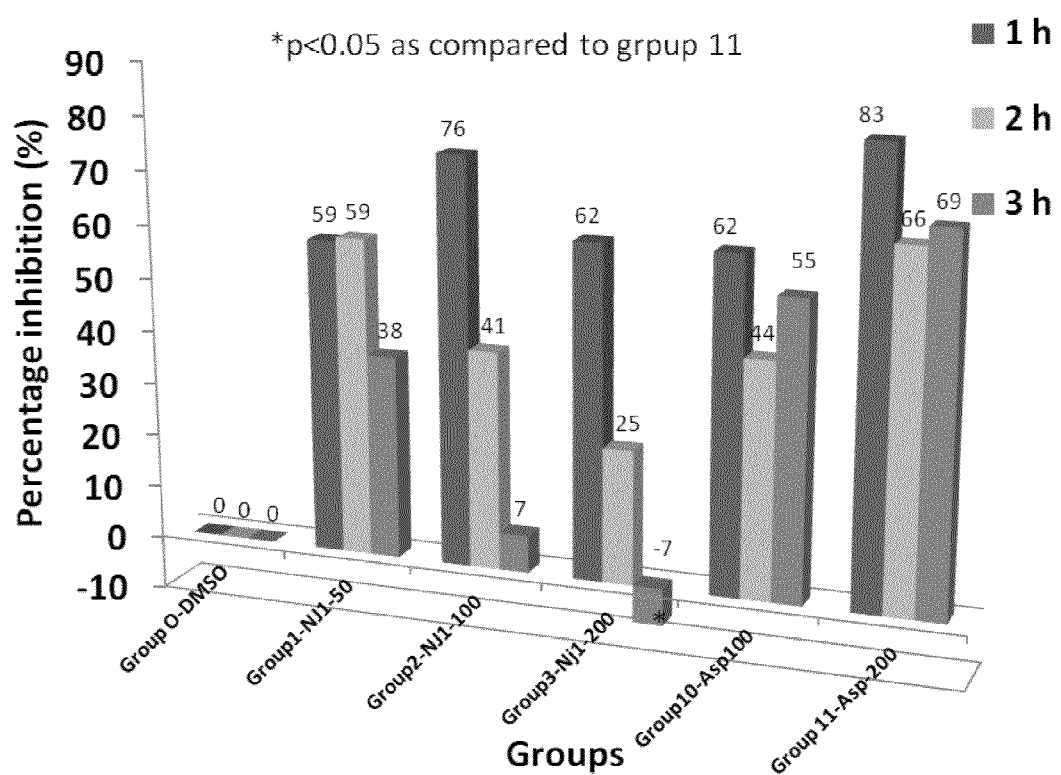
FIG. 10 is a bar graph showing percentage inhibition of paw edema with NJ1 (turmeric oil distillate 115° C.-120°/high vacuum (~100 torr). Groups are as shown in Table 4.
Figure 11:
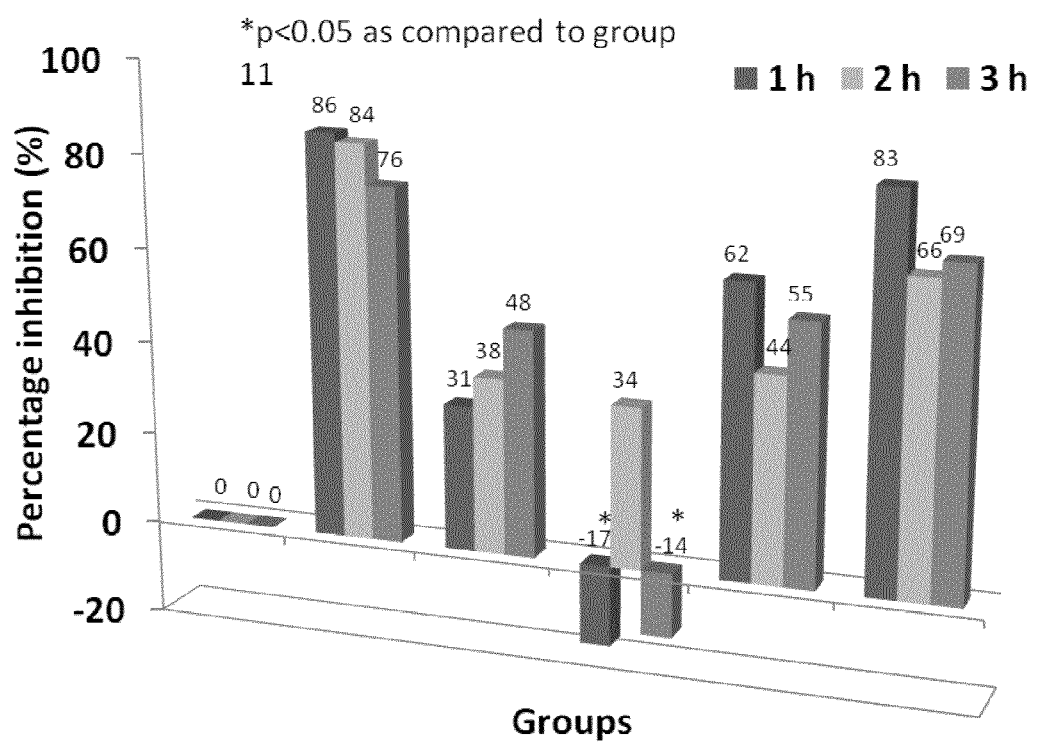
FIG. 11 is a bar graph showing percentage inhibition of paw edema with NJ2 (omega-3 DHA/EPA—fish oil). Groups are as shown in Table 4.
Figure 12:
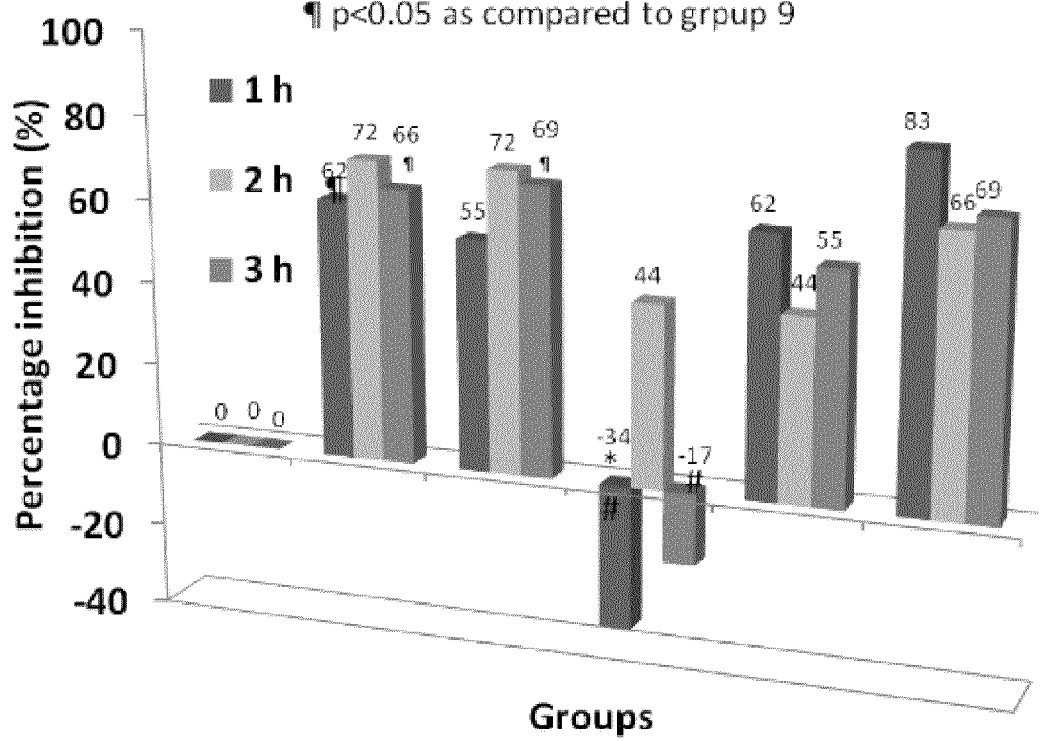
FIG. 12 is a bar graph showing percentage inhibition of paw edema with NJ3 (1:1 mix of turmeric oil distillate 115° C.-120° C./high vacuum (~100 torr)+omega-3 DHA/EPA—fish oil). Groups are as shown in Table 4.

Carrageen Induced Paw Edema:

There was significant increase in paw measurements (mm) after carrageen injection in all the groups (Table 5). The increase was maximum in group 0 and 12 (control groups) verifying the effectiveness of the method. In % inhibition of paw edema, all drugs in various groups inhibited the edema. The standard used (aspirin) significantly inhibited the development of the edema as compared to control groups confirming the validity of the method (FIG. 9). The formulation NJ1 (50 mg/kg) significantly inhibited edema at 1 hour as compared to control groups (FIG. 10). This formulation also inhibited edema at 2 and 3 hours as compared to group 1 (DMSO), but the inhibition was not significant as compared to aspirin (group 5 and 6). Group 3 (NJ1 100 mg/kg) significantly inhibited edema as compared to DMSO (group 1) at 1 hour only (FIG. 11). Group 3 (2 and 3 hour) and group 4 (all times) inhibited edema less than the standard drug aspirin (FIG. 12). NJ2 and NJ3 did not significantly inhibit edema as compared to control and aspirin. In fact the percentage inhibition was significantly less with NJ2 (100 and 200 mg/kg-group 3 and 4) and NJ3 (200 mg/kg-group 4). The % inhibition of paw edema at 3 hours was maximum for NJ 1 (50 mg/kg) followed by aspirin 200 mg/kg and aspirin 100 mg/kg.

TABLE 5

Paw circumference (mm) in various groups

| Groups | 0 h | 1 h | 2 h | 3 h |
|---|---|---|---|---|
| 0 | 2.75 ± 0.3 | 3.475 ± 0.19* | 3.55 ± 0.42* | 3.475 ± 0.33* |
| 1 | 2.775 ± 0.13 | 3.075 ± 0.10* | 3.1 ± 0.43 | 3.225 ± 0.21* |

TABLE 5-continued

Paw circumference (mm) in various groups

| Groups | 0 h | 1 h | 2 h | 3 h |
|---|---|---|---|---|
| 2 | 2.65 ± 0.24 | 2.825 ± 0.26* | 3.125 ± 0.26* | 3.325 ± 0.24* |
| 3 | 2.75 ± 0.10 | 3.025 ± 0.13* | 3.35 ± 0.19* | 3.525 ± 0.10* |
| 4 | 3.25 ± 0.21 | 3.35 ± 0.30 | 3.375 ± 0.19* | 3.425 ± 0.29 |
| 5 | 3.4 ± 0.12 | 3.9 ± 0.73* | 3.9 ± 0.26* | 3.775 ± 0.22* |
| 6 | 2.725 ± 0.30 | 3.575 ± 0.17* | 3.25 ± 0.26 | 3.55 ± 0.37* |
| 7 | 3.275 ± 0.19 | 3.55 ± 0.10* | 3.5 ± 0.35* | 3.525 ± 0.38 |
| 8 | 3.025 ± 0.13 | 3.35 ± 0.19* | 3.25 ± 0.37 | 3.25 ± 0.38* |
| 9 | 2.675 ± 0.22 | 3.65 ± 0.12* | 3.125 ± 0.51* | 3.525 ± 0.23* |
| 10 | 3.125 ± 0.13 | 3.475 ± 0.15 | 3.6 ± 0.14* | 3.475 ± 0.10* |
| 11 | 3.3 ± 0.18 | 3.425 ± 0.21 | 3.575 ± 0.13* | 3.55 ± 0.10* |
| 12 | 3.525 ± 0.53 | 4.15 ± 0.24* | 4.4 ± 0.22* | 4.55 ± 0.24* |

*$p < 0.05$ as compared to 0 hour

Figure 13:
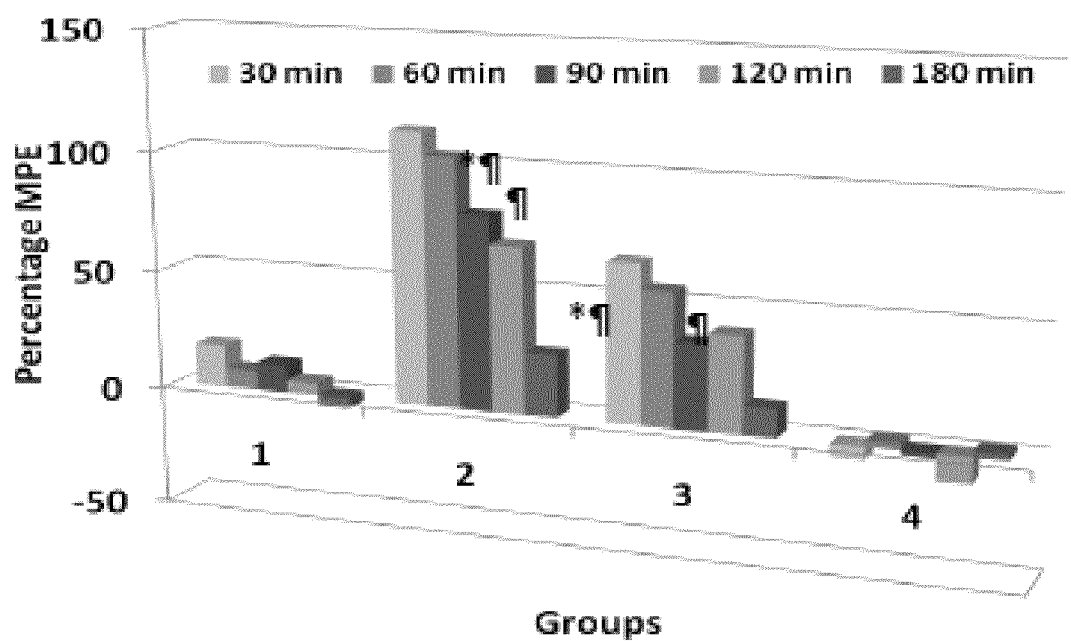
FIG. 13 is a bar graph showing percentage MPE in tail flick test with controls. Group 1=DMSO; Group 2=aspirin 100 mg/kg; Group 3=aspirin 200 mg/kg; and Group 4=normal saline. *P<0.05 as compared to Group 1; #P<0.05 as compared to Group 4.
Figure 14:
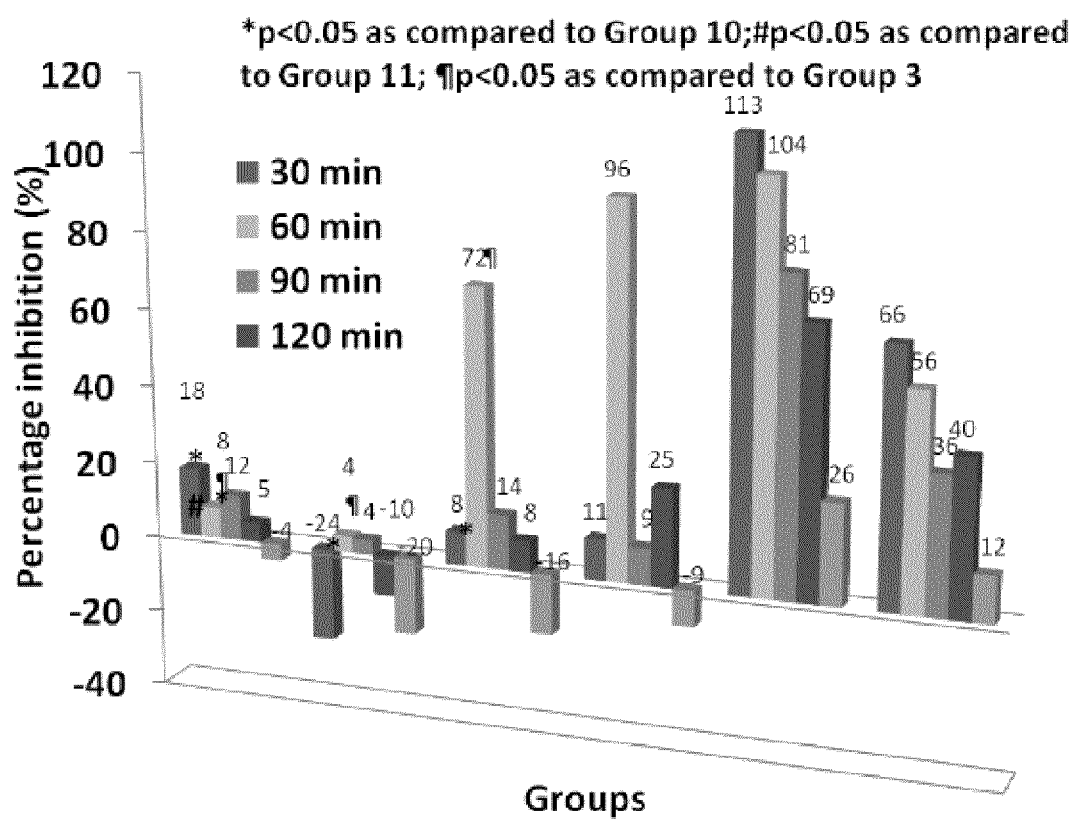
FIG. 14 is a bar graph showing percentage MPE in tail flick test with NJ1 (turmeric oil distillate 115° C.-120°/high vacuum (~100 torr). Groups are as shown in Table 4.
Figure 15:
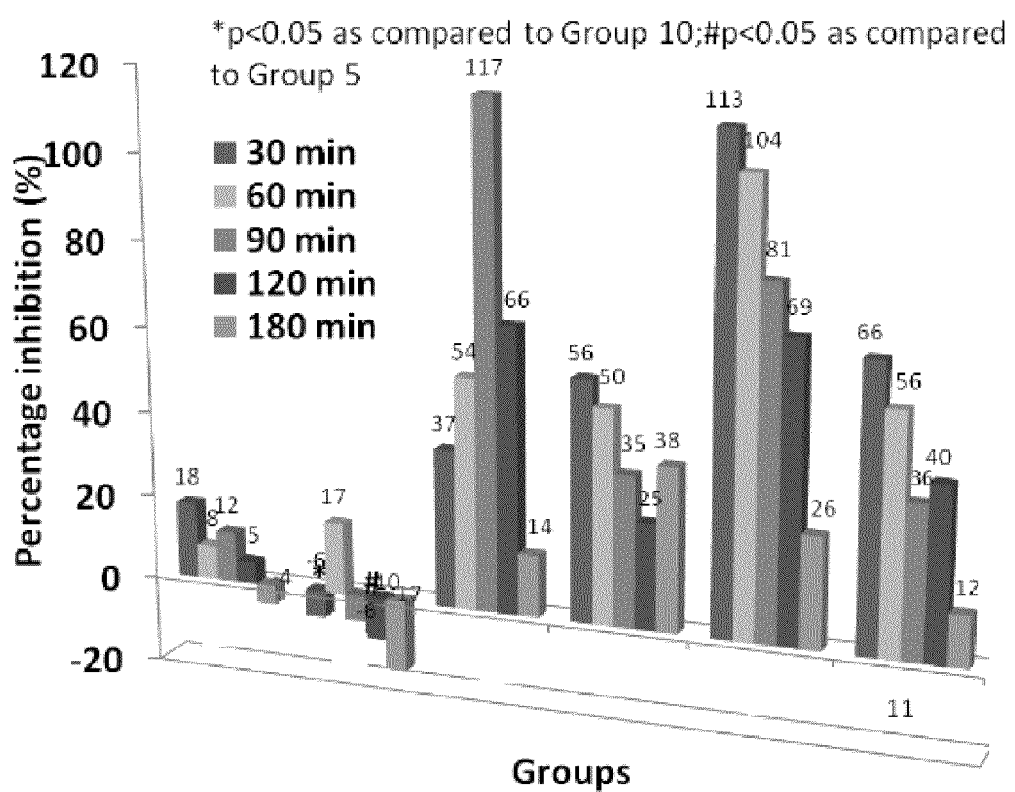
FIG. 15 is a bar graph showing percentage MPE in tail flick test with NJ2 (omega-3 DHA/EPA—fish oil). Groups are as shown in Table 4.
Figure 16:
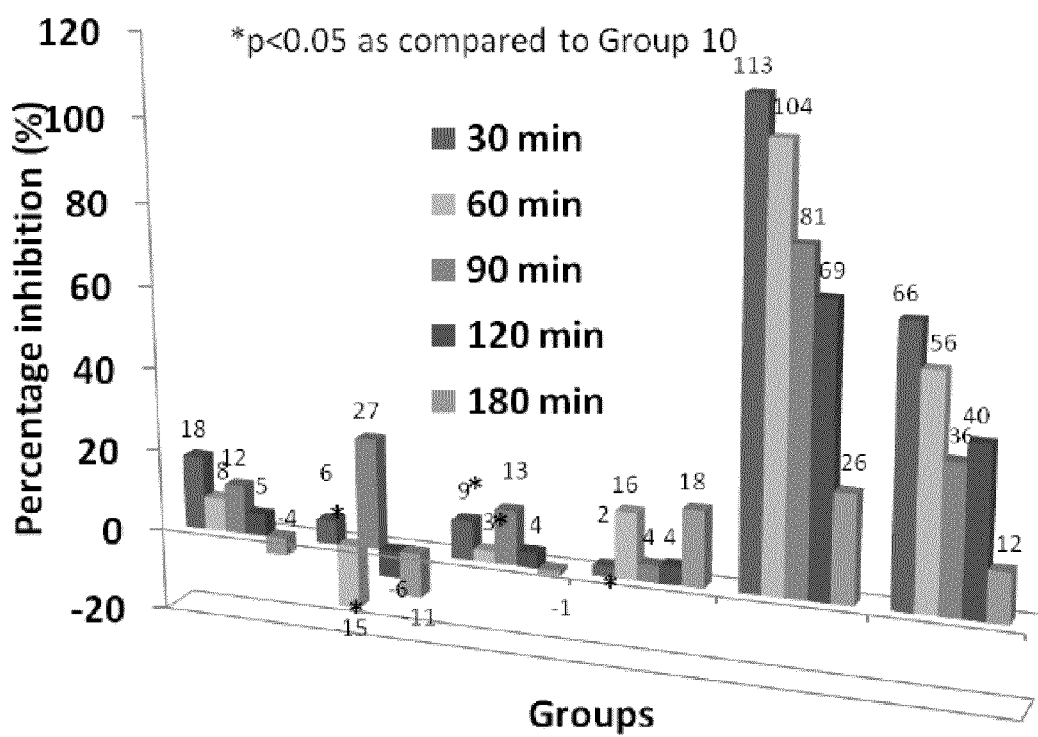
FIG. 16 is a bar graph showing percentage MPE in tail flick test with NJ3 (1:1 mix of turmeric oil distillate 115° C.-120° C./high vacuum (~100 torr)+omega-3 DHA/EPA—fish oil). Groups are as shown in Table 4.
Figure 17A:
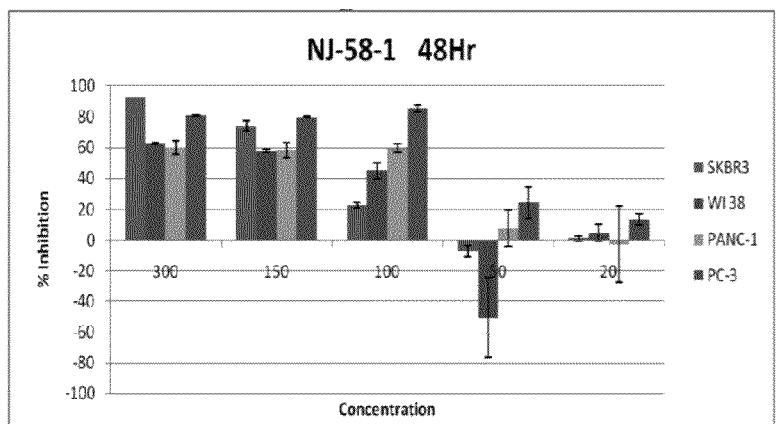
FIGS. 17A and 17B are bar graph (FIG. 17A) and line graph (FIG. 17B) showing % cellular inhibition of various cell lines breast (SKBR3), pancreatic (Panc1), and prostate (PC-3) with NJ-58-1 (diacetylcurcumin) at 48 hours. Non-cancer cell line WI-38 was used as a control.
Figure 17B:
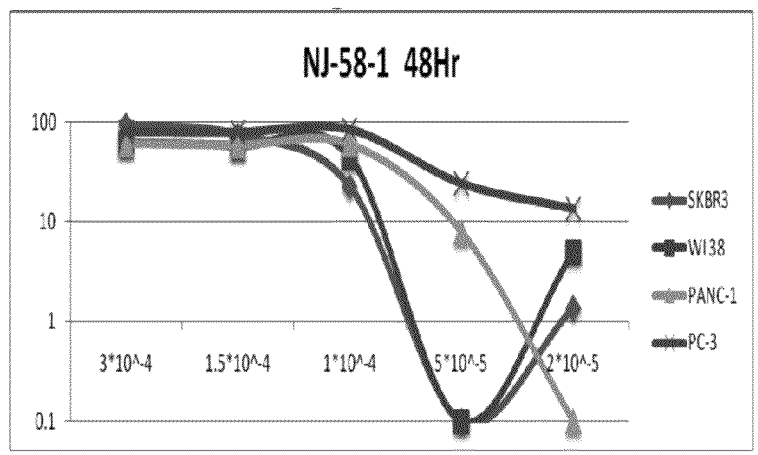
Figure 18A:
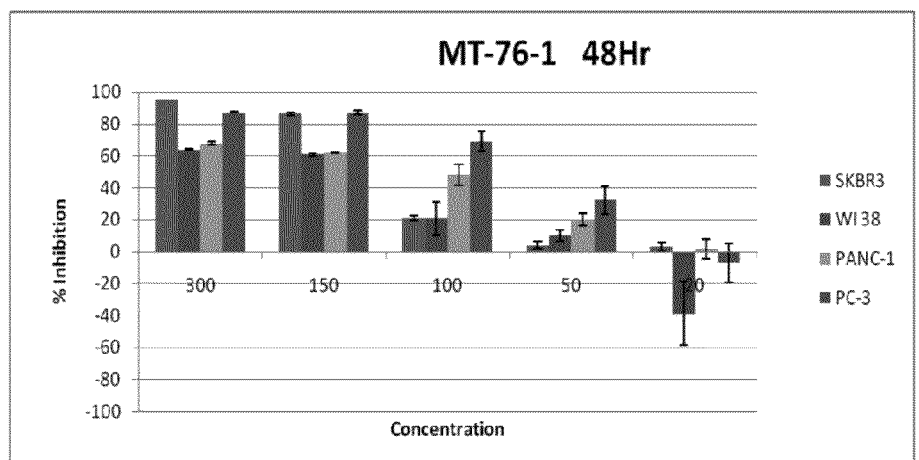
FIGS. 18A and 18B are bar graph (FIG. 18A) and line graph (FIG. 18B) showing % cellular inhibition of various cell lines breast (SKBR3), pancreatic (Panc1), and prostate (PC-3) with MT-76-1 (curcumin-glutarate) at 48 hours. Non-cancer cell line WI-38 was used as a control.
Figure 18B:
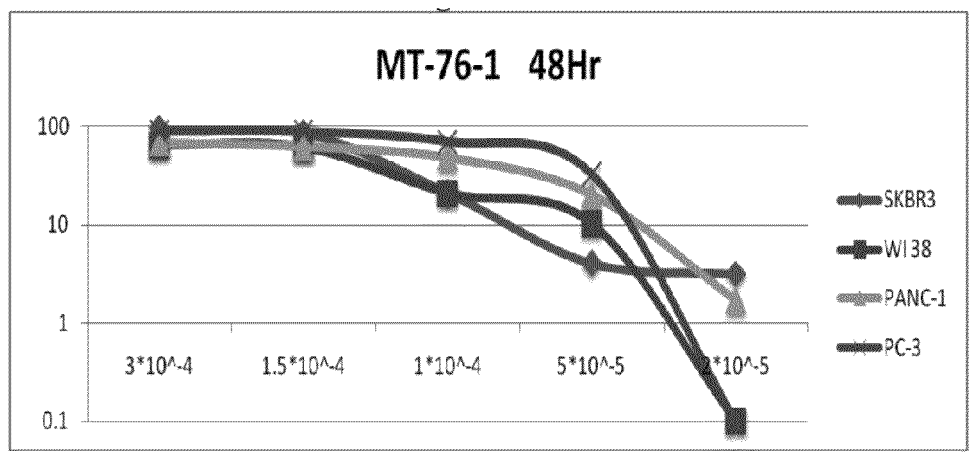
Figure 19A:
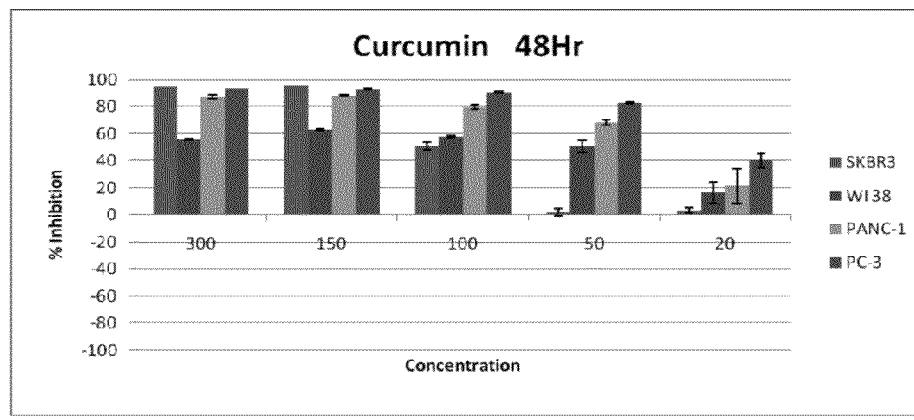
FIGS. 19A and 19B are bar graph (FIG. 19A) and line graph (FIG. 19B) showing % cellular inhibition of various cell lines breast (SKBR3), pancreatic (Panc1), and prostate (PC-3) with curcumin at 48 hours. Non-cancer cell line WI-38 was used as a control.
Figure 19B:
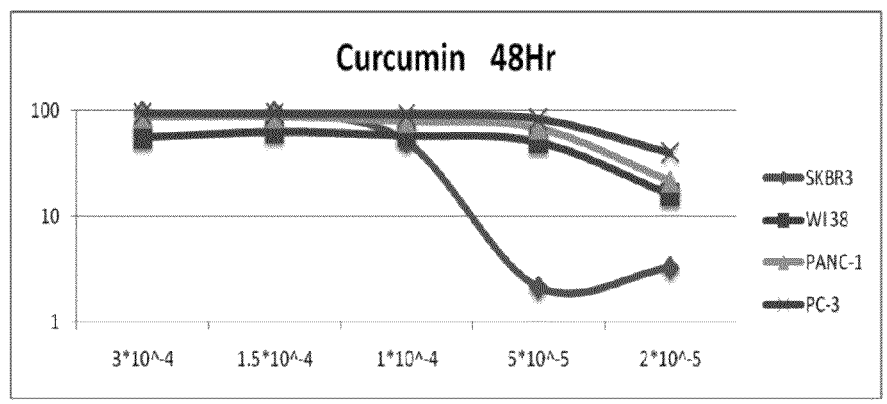
Figure 20A:
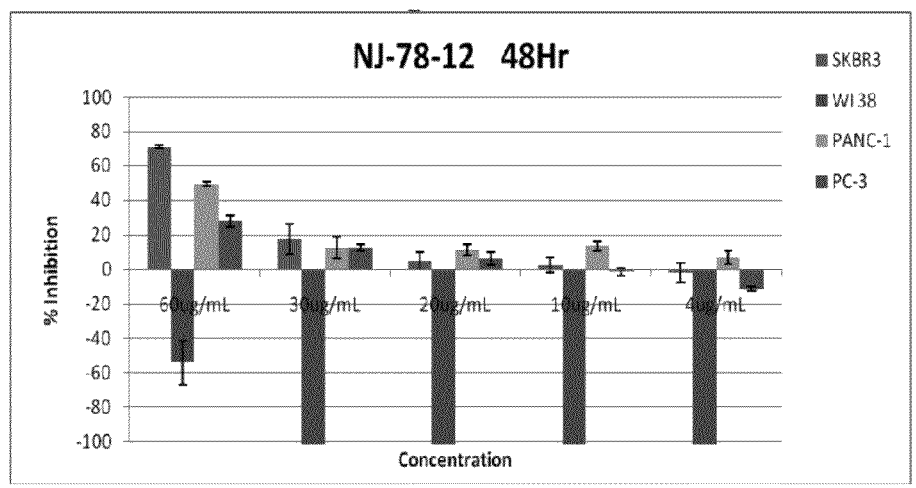
FIGS. 20A and 20B are bar graph (FIG. 20A) and line graph (FIG. 20B) showing % cellular inhibition of various cell lines breast (SKBR3), pancreatic (Panc1), and prostate (PC-3) with NJ-78-12 (turmeric oil distillate) at 48 hours. Non-cancer cell line WI-38 was used as a control.
Figure 20B:
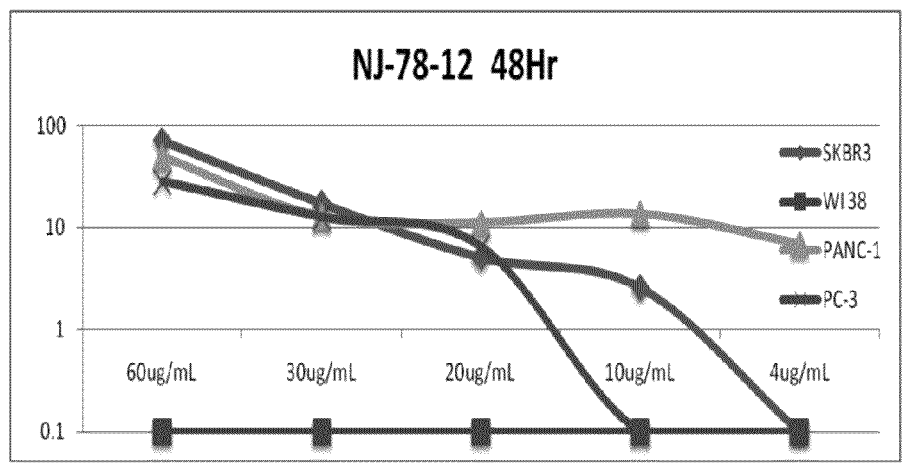
Figure 21A:
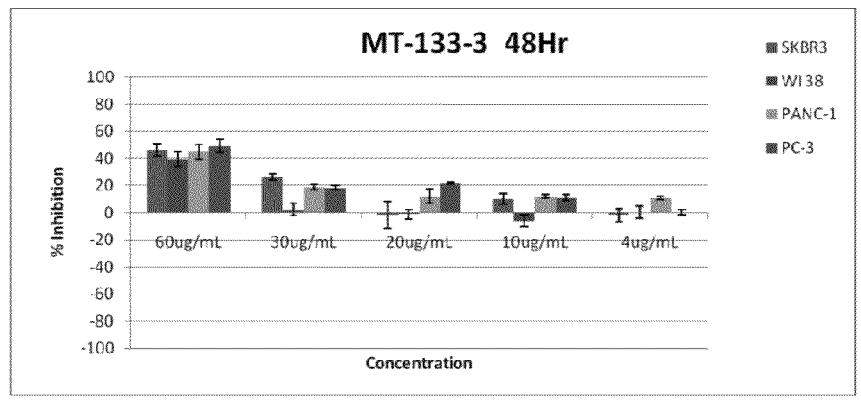
FIGS. 21A and 21B are bar graph (FIG. 21A) and line graph (FIG. 21B) showing % cellular inhibition of various cell lines breast (SKBR3), pancreatic (Panc1), and prostate (PC-3) with MT-133-3 (turmeric oil distillate fraction). Non-cancer cell line WI-38 was used as a control. Cells were treated with MT-133-3 for 48 hours.
Figure 21B:
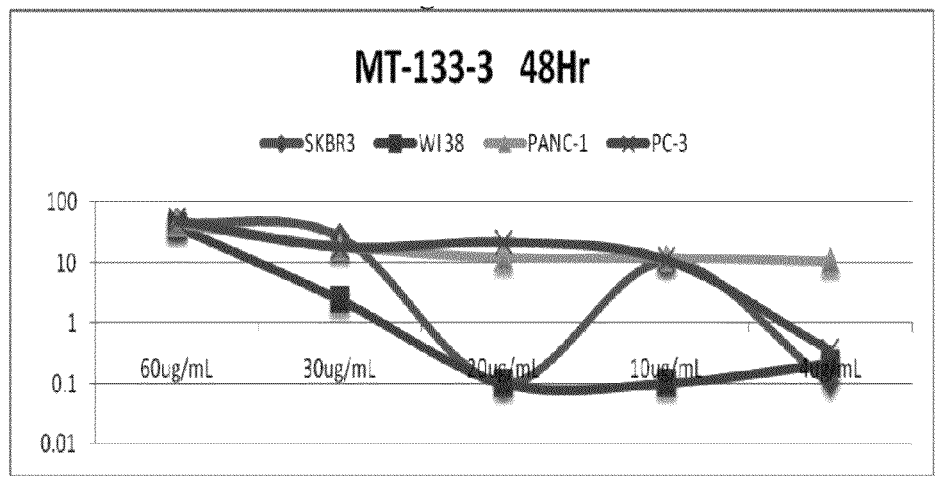
Figure 22A:
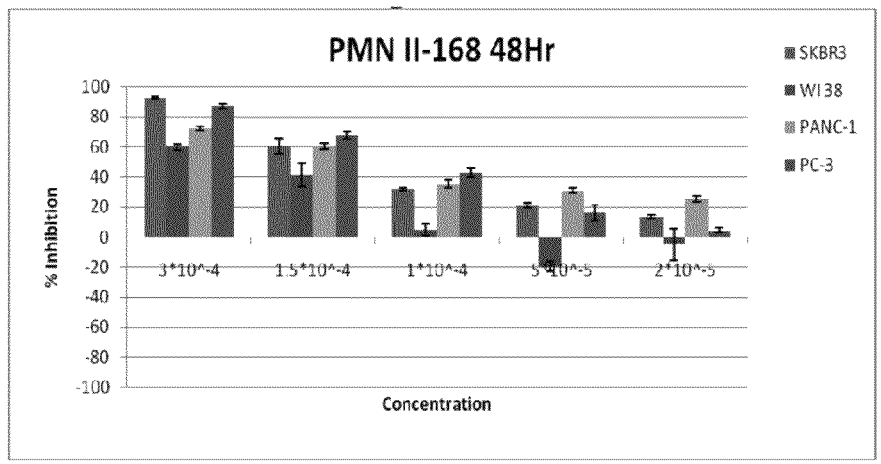
FIGS. 22A and 22B are bar graph (FIG. 22A) and line graph (FIG. 22B) showing % cellular inhibition of various cell lines breast (SKBR3), pancreatic (Panc1), and prostate (PC-3) with PMN II-168 (glucose-aspirin) at 48 hours. Non-cancer cell line WI-38 was used as a control.
Figure 22B:
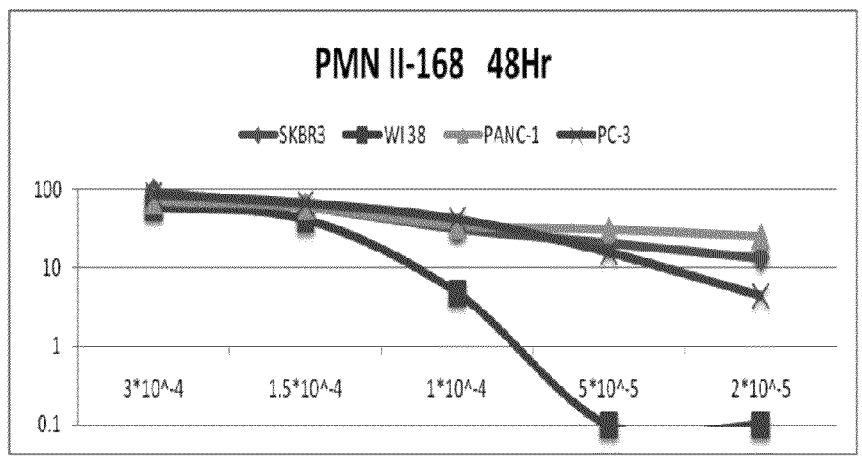
Figure 23A:
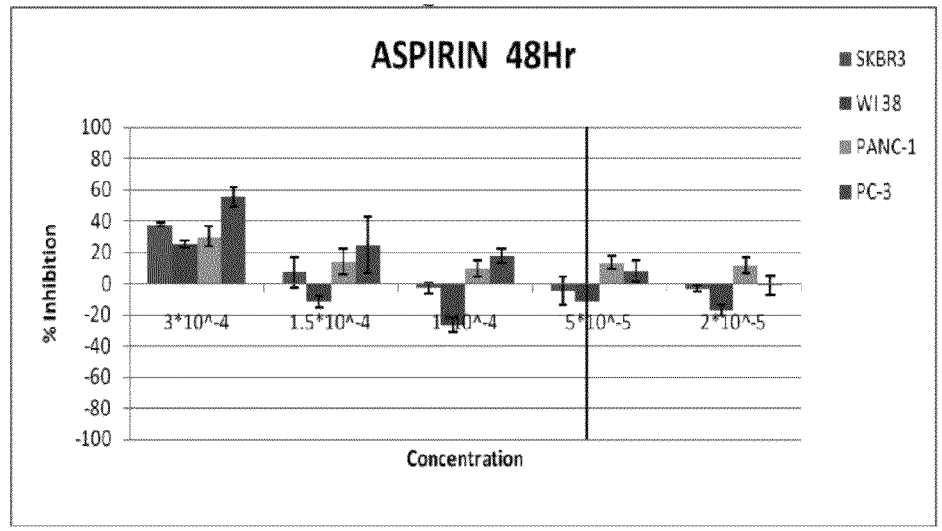
FIGS. 23A and 23B are bar graph (FIG. 23A) and line graph (FIG. 23B) showing % cellular inhibition of various cell lines breast (SKBR3), pancreatic (Panc1), and prostate (PC-3) with aspirin at 48 hours. Non-cancer cell line WI-38 was used as a control.
Figure 23B:
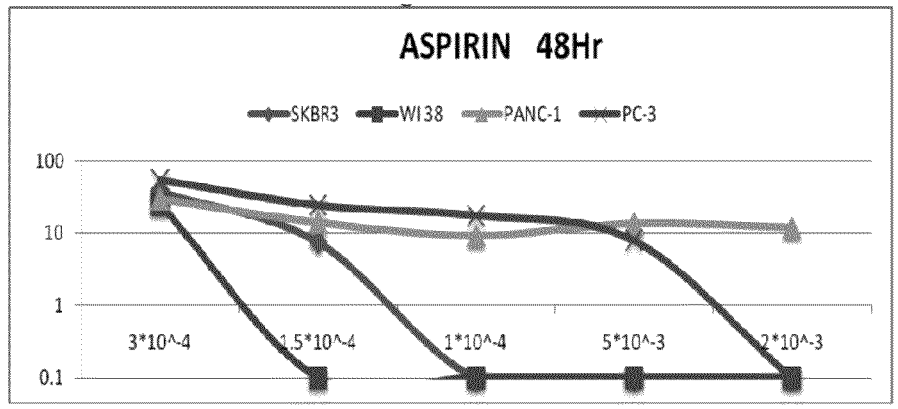
Figure 24A:
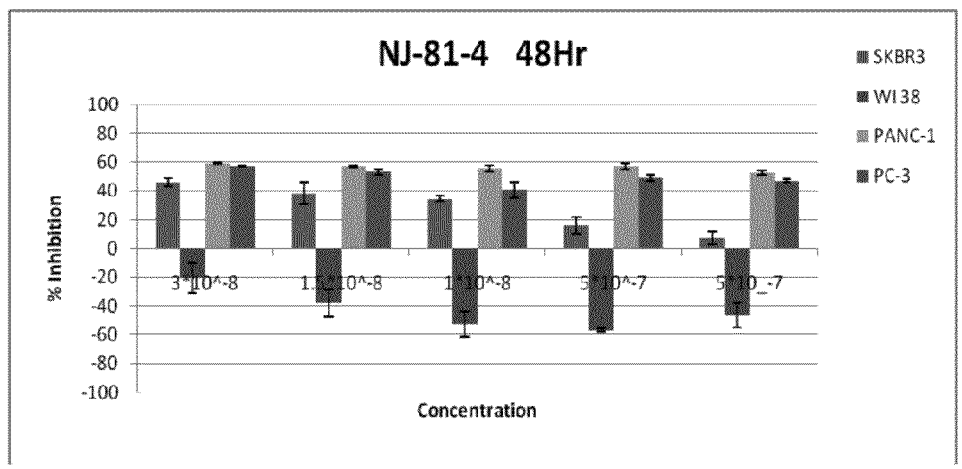
FIGS. 24A and 24B are bar graph (FIG. 24A) and line graph (FIG. 24B) showing % cellular inhibition of various cell lines breast (SKBR3), pancreatic (Panc1), and prostate (PC-3) with NJ-81-4 (mixture of turmeric oil distillation fraction NJ-78-12 (10 mg) and Paclitaxel (taxol) (1 mg)) at 48 hours. Non-cancer cell line WI-38 was used as a control.
Figure 24B:
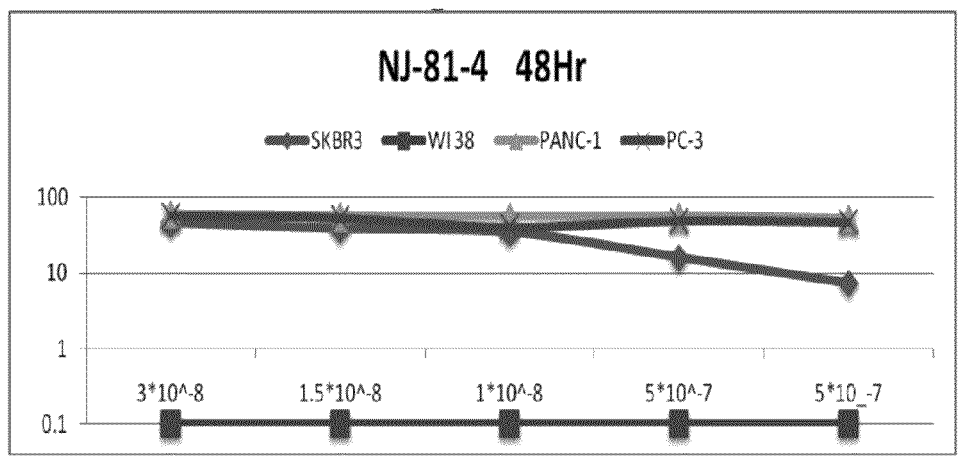
Figure 25A:
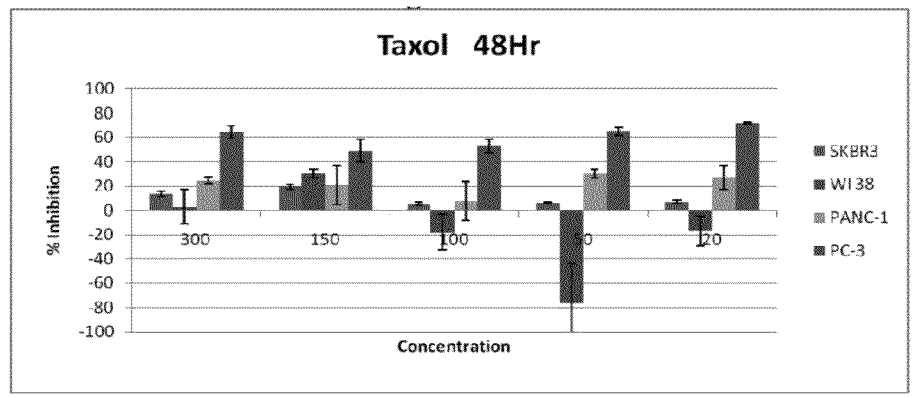
FIGS. 25A and 25B are bar graph (FIG. 25A) and line graph (FIG. 25B) showing % cellular inhibition of various cell lines breast (SKBR3), pancreatic (Panc1), and prostate (PC-3) with taxol at 48 hours. Non-cancer cell line WI-38 was used as a control.
Figure 25B:
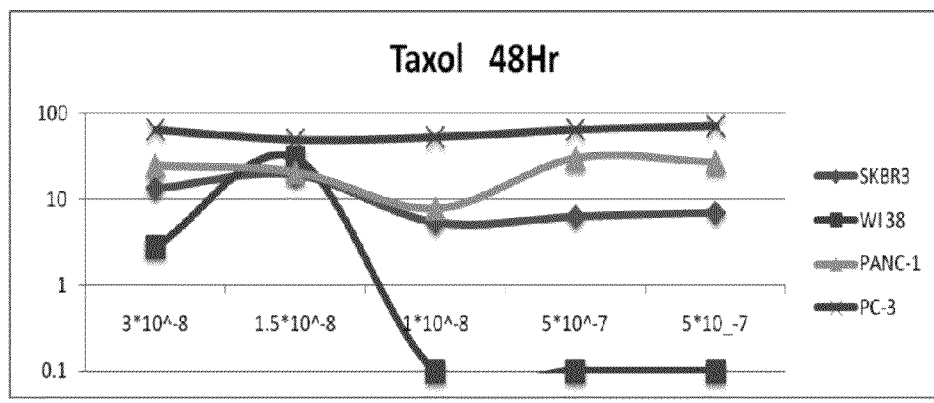
Figure 26A:
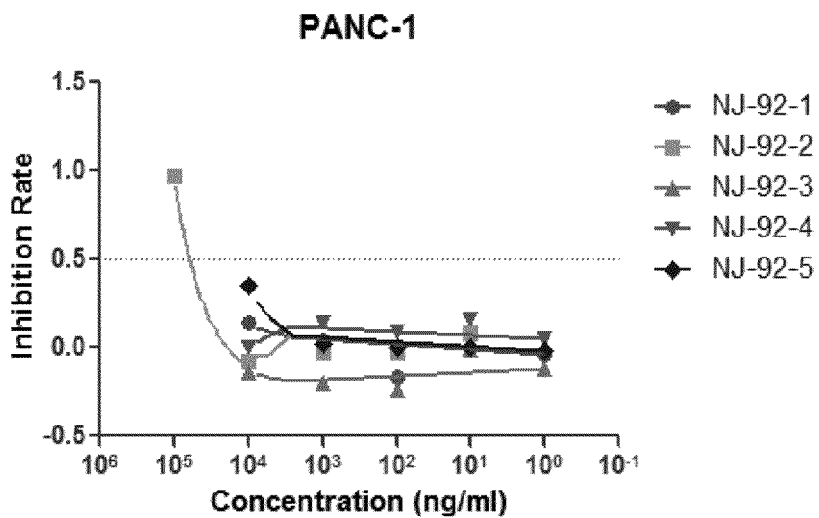
FIGS. 26A-26D are line graphs showing inhibition rate of NJ-92-1 (gemcitabine), NJ-92-2 (MT-133-3), NJ-92-3 (gemcitabine (1 mg)+MT-133-3 (10 mg)), NJ-92-4 (Paclitaxel), and NJ-92-5 (Paclitaxel (1 mg)+MT-133-3 (10 mg)) on cancer cell lines PANC-1 (FIG. 26A), PC3 (FIG. 26B) and SK- BR-3 (FIG. 26C). Non-cancer cell line WI38 (FIG. 26D) was used as a control. No $LD_{50}$ (lethal dose 50%) was observed for the tested compounds; thus, demonstrating that these compounds were not cytotoxic under the testing conditions.
Figure 26B:
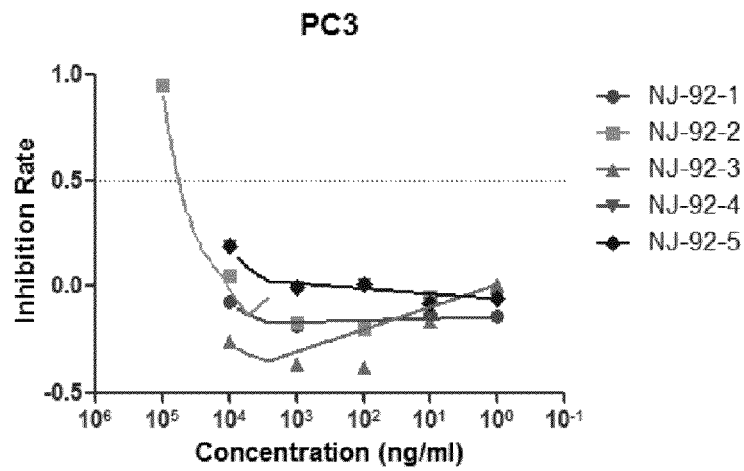
Figure 26C:
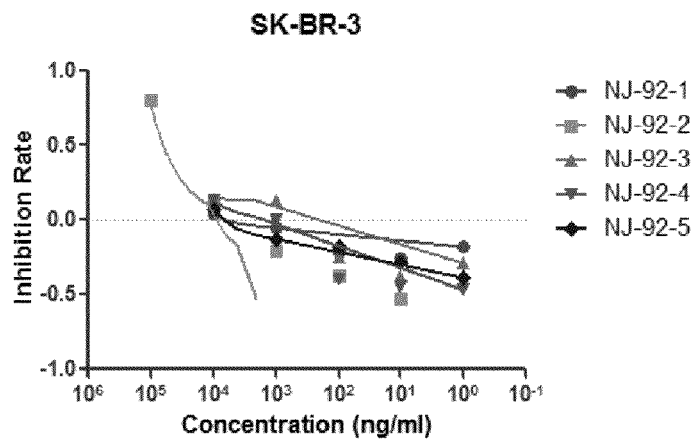
Figure 26D:
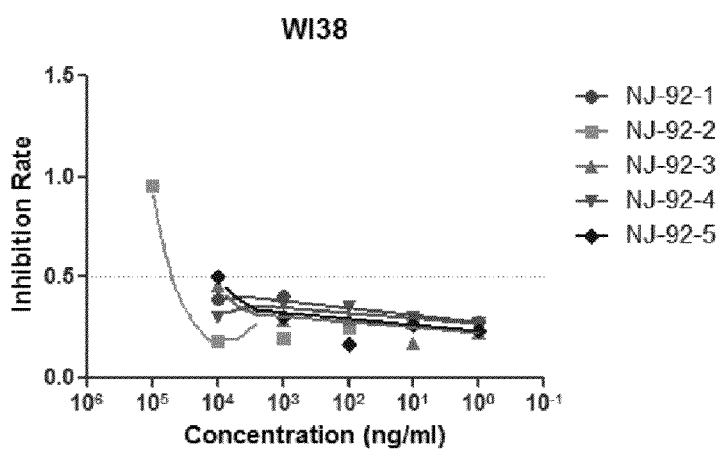
Figure 27A:
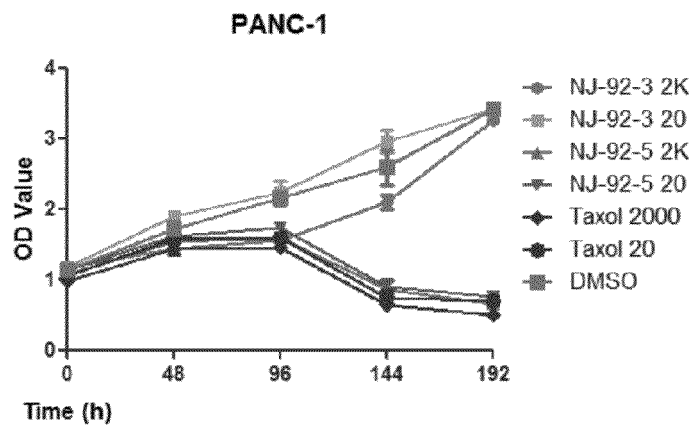
FIGS. 27A-27D are line graphs showing inhibition rate of NJ-92-3 2K (2,000 ng/ml) (gemcitabine (1 mg)+MT-133-3 (10 mg)), NJ-92-3 20 (20 ng/ml), NJ-92-5 2K (2000 ng/ml) (Paclitaxel (1 mg)+MT-133-3 (10 mg)), NJ-92-5 20 (20 ng/ml), Taxol 2K (2000 ng/ml), Taxol 20 (20 ng/ml), and DMSO on cancer cell lines PANC-1 (FIG. 27A), PC3 (FIG. 27B) and SK-BR-3 (FIG. 27C). Non-cancer cell line WI38 (FIG. 27D) was used as a control.
Figure 27B:
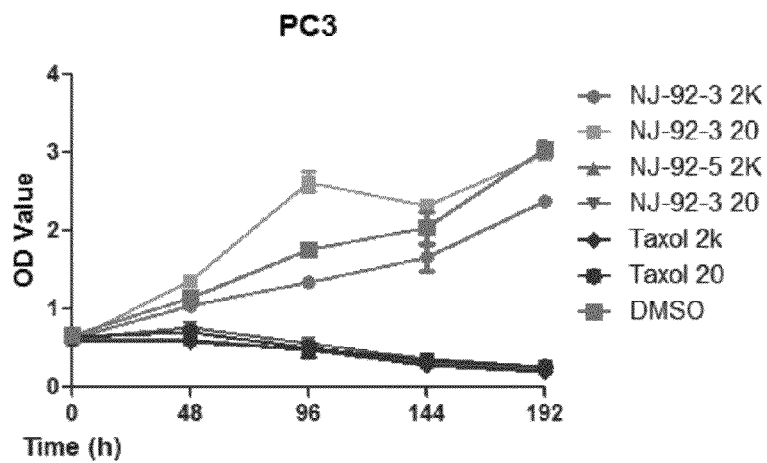
Figure 27C:
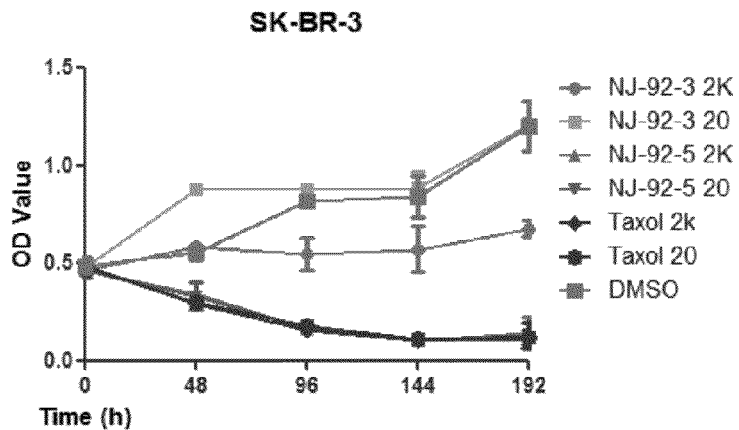
Figure 27D:
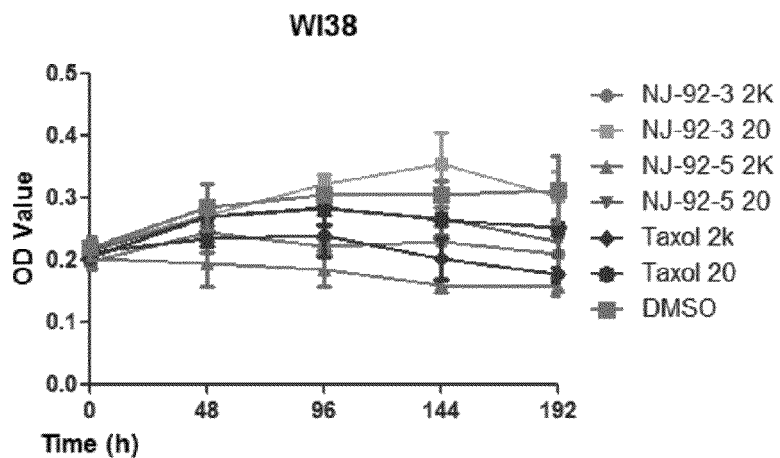
Figure 28A:
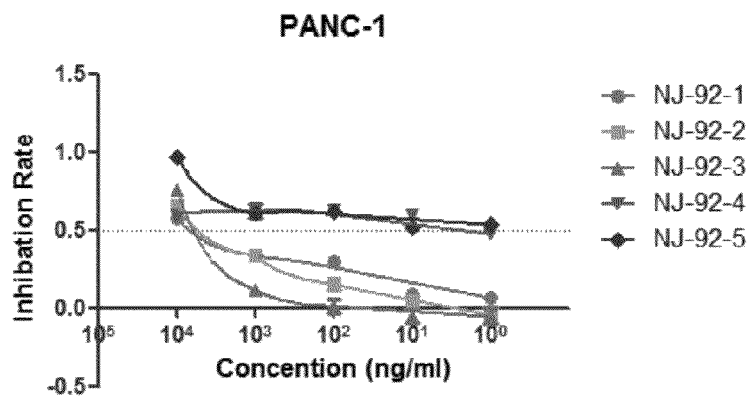
FIGS. 28A-28D are line graphs showing inhibition rate of NJ-92-1 (gemcitabine), NJ-92-2 (MT-133-3, NJ-92-3 (gemcitabine (1 mg)+MT-133-3 (10 mg)), NJ-92-4 (Paclitaxel), and NJ-92-5 (Paclitaxel (1 mg)+MT-133-3 (10 mg)) on cancer cell lines PANC-1 (FIG. 28A), PC3 (FIG. 28B) and SK-BR-3 (FIG. 28C). Non-cancer cell line WI38 (FIG. 28D) was used as a control.
Figure 28B:
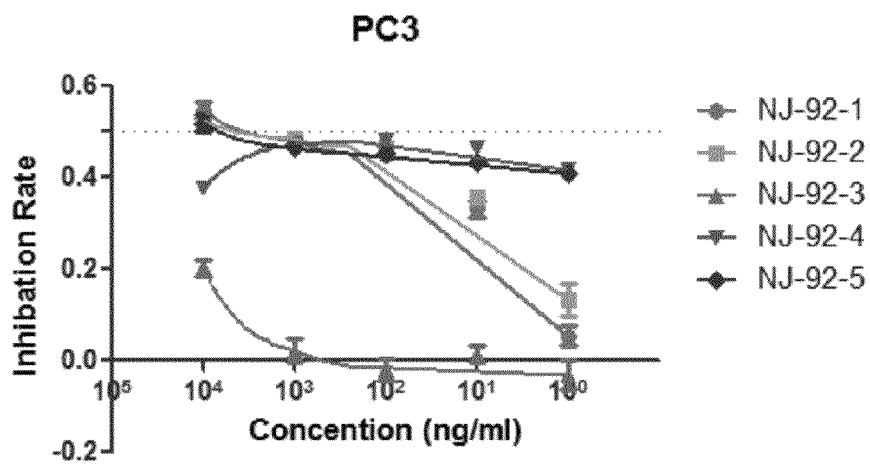
Figure 28C:
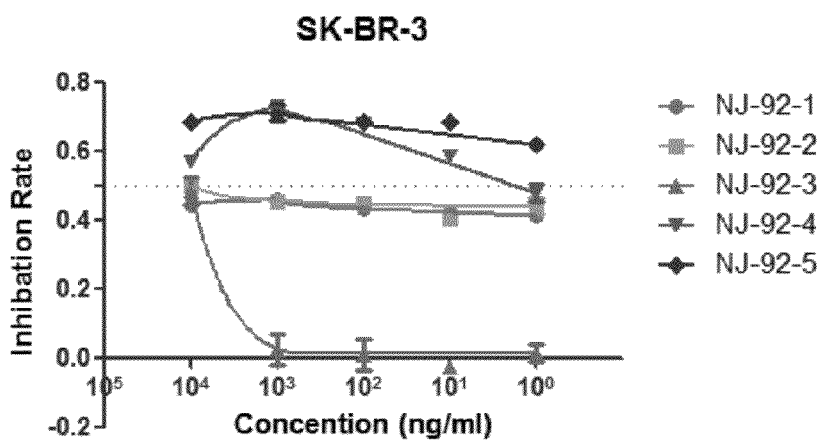
Figure 28D:
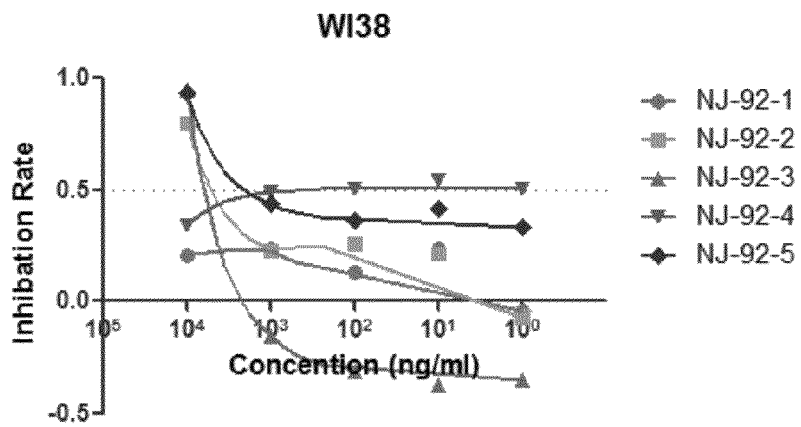
Figure 29A:
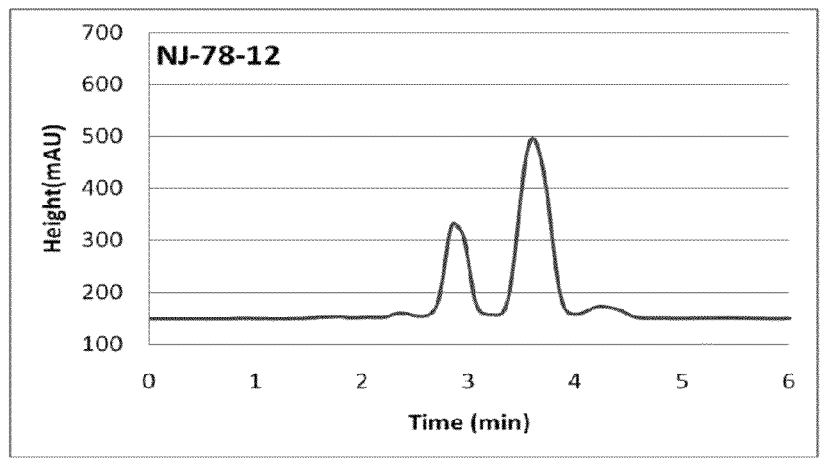
FIGS. 29A and 29B show HPLC spectra of turmeric oil extracts NJ-78-12 (FIG. 29A) and MT-133-3 (FIG. 29B). HPLC conditions: X-Terra C-18 column (4.6×150 mm, 5 µm), acetonitrile/water (85/15), 1 mL/min, UV detector @ 254 nm.
Figure 29B:
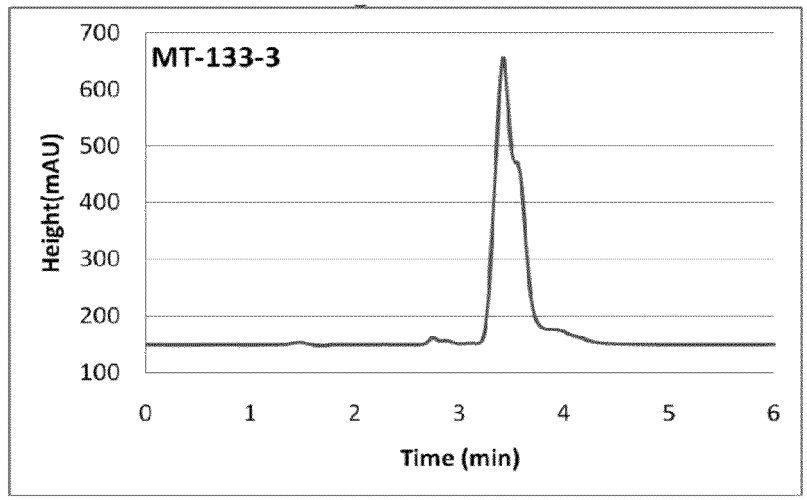

Tail Flick:

The increase no increase in tail flick latency in group 0 and 12 (control groups) verifying the usefulness of the method (Table 6). There was significant increase in tail flick latency (seconds) with some drugs. The % MPE was significantly more with aspirin as compared to control groups (FIG. 13) confirming the validity of the method (FIG. 5). The % MPE was significantly more with formulation NJ1 (50 mg/kg) at 180 minutes as compared to DMSO (FIG. 14). The % MPE was less with NJ2 and NJ3 as compared to aspirin at all dose levels and at all times (FIG. 15). The % MPE with NJ3 was less as compared to aspirin (FIG. 16).

TABLE 6

Tail flick latency time (seconds) in various groups

| Groups | 0 min | 30 min | 60 min | 90 min | 120 min | 180 min |
|---|---|---|---|---|---|---|
| 0 | 2.02 ± 0.26 | 2.37 ± 0.39 | 2.13 ± 0.38 | 2.24 ± 0.33 | 2.10 ± 0.70 | 1.915 ± 0.13 |
| 1 | 1.33 ± 0.24 | 1.46 ± 0.43 | 2.26 ± 0.38* | 1.50 ± 0.20* | 1.39 ± 0.18 | 1.105 ± 0.13 |
| 2 | 1.295 ± 0.22 | 1.39 ± 0.21 | 2.50 ± 0.13* | 1.38 ± 0.24 | 1.55 ± 0.37 | 1.125 ± 0.25 |
| 3 | 1.65 ± 0.27 | 2.27 ± 0.54* | 2.51 ± 0.39* | 3.47 ± 0.43* | 2.76 ± 0.75* | 1.85 ± 0.30 |
| 4 | 1.71 ± 0.54 | 2.40 ± 0.58 | 2.36 ± 0.15 | 2.105 ± 0.13 | 1.96 ± 0.10 | 2.22 ± 0.23 |
| 5 | 1.79 ± 0.22 | 1.97 ± 0.33 | 1.83 ± 0.13 | 2.01 ± 0.70 | 1.855 ± 0.26 | 1.76 ± 0.14 |
| 6 | 1.76 ± 0.30 | 1.80 ± 0.29 | 1.97 ± 0.70 | 1.79 ± 0.69 | 1.78 ± 0.17 | 1.98 ± 0.31 |
| 7 | 1.63 ± 0.22 | 1.21 ± 0.20 | 1.68 ± 0.18 | 1.67 ± 0.71 | 1.45 ± 0.17 | 1.29 ± 0.49 |
| 8 | 1.77 ± 0.47 | 1.63 ± 0.51 | 2.00 ± 0.29 | 1.66 ± 0.53 | 1.61 ± 0.53 | 1.43 ± 0.29 |
| 9 | 2.29 ± 0.72 | 2.31 ± 0.46 | 1.82 ± 0.53 | 2.65 ± 0.93 | 1.89 ± 0.57 | 1.89 ± 0.16 |
| 10 | 1.64 ± 0.27 | 3.28 ± 0.26* | 3.28 ± 0.57* | 2.88 ± 0.26* | 2.73 ± 0.48* | 2.05 ± 0.76 |
| 11 | 2.32 ± 0.46 | 3.46 ± 0.77* | 3.46 ± 0.17* | 3.03 ± 0.42 | 3.12 ± 0.30 | 2.53.45 |
| 12 | 2.36 ± 0.38 | 2.377 ± 0.17 | 2.37 ± 0.39 | 2.28 ± 0.18 | 1.90 ± 0.24 | 2.41 ± 0.34 |

*$p < 0.05$ as compared to 0 minutes

Carrageenan-induced hind paw edema is the standard experimental model of acute inflammation. Carrageenan is the agent of choice for testing anti-inflammatory drugs as it is not known to be antigenic and is devoid of apparent systemic effects. Moreover, the experimental model exhibits a high degree of reproducibility. Carrageenan-induced edema is a biphasic response. The first phase is mediated through the release of histamine, serotonin and kinins whereas the second phase is related to the release of prostaglandin and slow reacting substances which peak at 3 hour. See for example, Vinegar, R., Schreiber, W. & Hugo R., *J. Pharmacol. Exp. Ther.*, 1969, 166: 96-103.

The increase in the paw volume following carrageenan administration in the control and aspirin treated group corresponds with the findings of previous workers. NJ1 produced significant inhibition of carrageenan-induced paw edema. The effect produced is equivalent to the effect of aspirin indicating similar efficacy. The effect with NJ1 was more at lower dose. However NJ1 showed dose dependant analgesic activity on tail flick test, higher dose showing more effect. NJ2 and NJ3 did not show any significant activity, in fact their effect was lower than the aspirin. Thus, these results demonstrated that NJ1 has significant anti-inflammatory and analgesic activity in animal models.

Example 7

Anti-Cancer Activity of Turmeric Oil Distillation Fraction and Curcumin Analogs

Assays were performed with 3 cancer cell lines: breast (SKBR3), pancreatic (Panc1), prostate (PC-3) and 1 normal (nor-cancer) cell line (WI-38). Compounds were delivered to the cells after dissolving in DMSO. Five dilutions per compound were tested on a total of 4 cell lines in 96 well plates. Cellular inhibition was measured using Alamar Blue. After addition of compound a 24 hour and 48 hour time point using fluorescent plate reader was taken. Data from plate reader was analyzed in the following way: % inhibition bar graphs, % inhibition line graphs and $IC_{50}$ growth inhibition values. The results of the experiments are shown in FIGS. 17A-25B. $IC_{50}$ values are summarized in Tables 7-14. In Tables 7-14, $IC_{50}$ units are Molar (M).

TABLE 7

Summary of $IC_{50}$ values for NJ-58-1, MT-76-1 and curcumin (24 hours)

| Compound | Cell line | $IC_{50}$ |
|---|---|---|
| NJ-58-1 24 | SKBR3 | 1.71E−04 |
| NJ-58-1 24 | WI38 | 4.39E−03 |
| NJ-58-1 24 | PANC1 | 2.68E−04 |
| NJ-58-1 24 | PC3 | 9.61E−05 |
| MT-76-1 24 | SKBR3 | 1.69E−04 |
| MT-76-1 24 | WI38 | 2.98E−04 |
| MT-76-1 24 | PANC1 | 3.54E−05 |
| MT-76-1 24 | PC3 | 1.27E−04 |
| Curcumin 24 | SKBR3 | 8.41E−05 |
| Curcumin 24 | WI38 | 1.00E−03 |
| Curcumin 24 | PANC1 | 4.15E−05 |
| Curcumin 24 | PC3 | 2.95E−05 |

TABLE 8

Summary of $IC_{50}$ values for NJ-78-12 and MT-133-1 (24 hours)

| Compound | Cell line | $IC_{50}$ |
|---|---|---|
| NJ-78-12 | SKBR3 | 5.77E−03 |
| NJ-78-12 | WI38 | 1.40E+03 |
| NJ-78-12 | PANC1 | 2.95E−03 |
| NJ-78-12 | PC3 | 1.36E−03 |
| MT-133-3 | SKBR3 | 3.43E−04 |
| MT-133-3 | WI38 | 3.24E−04 |
| MT-133-3 | PANC1 | 3.95E−04 |
| MT-133-3 | PC3 | 3.27E−04 |

TABLE 9

Summary of $IC_{50}$ values for PMN II-168 and Aspirin (24 hours)

| Compound | Cell line | $IC_{50}$ |
|---|---|---|
| PMN II-168 | SKBR3 | 2.01E−04 |
| PMN II-168 | WI38 | 3.76E−04 |
| PMN II-168 | PANC1 | 3.99E−04 |
| PMN II-168 | PC3 | 8.32E−05 |
| ASPIRIN | SKBR3 | 7.31E−04 |
| ASPIRIN | WI38 | 6.19E−04 |
| ASPIRIN | PANC1 | 9.75E−04 |
| ASPIRIN | PC3 | 7.71E−04 |

TABLE 10

Summary of $IC_{50}$ values for NJ-81-4 and Taxol (24 hours)

| Compound | Cell line | $IC_{50}$ |
|---|---|---|
| NJ-81-4 | SKBR3 | 5.54E−07 |
| NJ-81-4 | WI38 | 4.13E−07 |
| NJ-81-4 | PANC1 | 9.90E−08 |
| NJ-81-4 | PC3 | 6.48E−08 |
| Taxol 24 | SKBR3 | 6.94E−07 |
| Taxol 24 | WI38 | 1.91E−05 |
| Taxol 24 | PANC1 | 1.53E−07 |
| Taxol 24 | PC3 | 5.81E−08 |

TABLE 11

Summary of $IC_{50}$ values for NJ-58-1, MT-76-1 and curcumin (48 hours)

| NJ-58-1 48 | SKBR3 | 1.25E−04 |
|---|---|---|
| NJ-58-1 48 | WI38 | 1.55E−04 |
| NJ-58-1 48 | PANC1 | 1.33E−04 |
| NJ-58-1 48 | PC3 | 6.70E−05 |
| MT-76-1 48 | SKBR3 | 1.18E−04 |
| MT-76-1 48 | WI38 | 1.66E−04 |
| MT-76-1 48 | PANC1 | 1.23E−04 |
| MT-76-1 48 | PC3 | 7.16E−05 |
| Curcumin 48 | SKBR3 | 9.94E−05 |
| Curcumin 48 | WI38 | 8.99E−05 |
| Curcumin 48 | PANC1 | 3.82E−05 |
| Curcumin 48 | PC3 | 2.42E−05 |

TABLE 12

Summary of $IC_{50}$ values for NJ-78-12 and MT-133-1 (48 hours)

| Compound | Cell line | $IC_{50}$ |
|---|---|---|
| NJ-78-12 | SKBR3 | 2.33E−04 |
| NJ-78-12 | WI38 | 2.98E−03 |
| NJ-78-12 | PANC1 | 3.22E−04 |
| NJ-78-12 | PC3 | 4.98E−04 |
| MT-133-3 | SKBR3 | 3.18E−04 |
| MT-133-3 | WI38 | 3.28E−04 |
| MT-133-3 | PANC1 | 4.02E−04 |
| MT-133-3 | PC3 | 3.34E−04 |

TABLE 13

Summary of $IC_{50}$ values for PMN II-168 and Aspirin (48 hours)

| Compound | Cell line | $IC_{50}$ |
|---|---|---|
| PMN II-168 | SKBR3 | 8.78E−05 |
| PMN II-168 | WI38 | 3.10E−04 |
| PMN II-168 | PANC1 | 9.05E−05 |
| PMN II-168 | PC3 | 8.14E−05 |
| ASPIRIN | SKBR3 | 6.93E−04 |
| ASPIRIN | WI38 | 5.01E−04 |
| ASPIRIN | PANC1 | 7.45E−04 |
| ASPIRIN | PC3 | 7.82E−04 |

TABLE 14

Summary of $IC_{50}$ values for NJ-81-4 and Taxol (48 hours)

| Compound | Cell line | $IC_{50}$ |
|---|---|---|
| NJ-81-4 | SKBR3 | 3.09E−07 |
| NJ-81-4 | WI38 | 8.12E−04 |
| NJ-81-4 | PANC1 | 4.60E−09 |
| NJ-81-4 | PC3 | 1.76E−08 |
| Taxol 48 | SKBR3 | 3.23E−06 |
| Taxol 48 | WI38 | 8.00E−05 |
| Taxol 48 | PANC1 | 1.80E−07 |
| Taxol 48 | PC3 | 8.03E−08 |

Glucose Aspirin (PMN II-168) Vs. Aspirin:

Examining the bar graphs at 24 hours, showed that PMN-II-168 had a modest 20% inhibition of cancer cell growth for the four lower concentrations while aspirin did not seem to inhibit growth by any significant means at 24 hours. $IC_{50}$ for PMN-II-168 were found to be 2.01E−04, 3.76E−04, 3.99E−04 and 8.32E−05 for SKBR3, WI38 PANC1 and PC-3 cells respectively. $IC_{50}$ for aspirin were found to be 7.31E−04, 6.19E−04, 9.75E−04 and 7.71E−04 for SKBR3, WI38 PANC1 and PC-3 cells respectively. $IC_{50}$ values are in Molar (M).

PMN-II-168 at 300 uM did inhibit cancer cell growth very well (up to 60% inhibition) while not playing a significant inhibitory role with the normal WI-38 cell lines. This was consistent at the various concentrations. Aspirin however did not have the same selectivity as PMN-II-168 as WI-38 cells as they were the most efficiently growth repressed at 24 hours. At 48 hours, while there was little change in aspirin inhibition (except for the highest 300 uM concentration), PMN-II-168 did significantly better. PMN-II-168 inhibited breast cancer line (skbr3) proliferation most efficiently (approximately 90% and 60% inhibition at the 300 uM and 150 uM concentration respectively). It also inhibited Panc-1 (~70% and 60%) and PC-3 (~85% and 65%) for the two highest concentrations, 300 uM and 150 uM respectively. Even at the lower concentrations, PMN-II-168 performed significantly better than aspirin.

Paclitaxel (Taxol) (1 mg) Vs. NJ-81-4 (Mixture of Turmeric Oil Distillation Fraction NJ-78-12 (10 mg) and Paclitaxel (1 mg)) at 48 Hours:

Taxol at the 48 hour treatment point was effective in inhibiting prostate (PC-3) cancer cells at all concentrations (~60 inhibition) and at the 300 and 150 nM concentrations inhibited the other cancer cell lines more modestly. On the other hand, at the same doses, NJ-81-4 was more effective as it inhibited Panc-1 and PC-3 by approximately ~60% at all concentrations when compared to untreated cells. SKBR3 cell growth proliferation was also inhibited with NJ-81-4 albeit more modestly up to (45% inhibition). In addition to the better inhibition, NJ-81-4 did not affect normal cell growth (WI-38). Taxol however did have some effect on normal cell growth.

Turmeric Oil Fraction NJ-78-12 and MT-133-3:

At the 48 hour time point bar graphs, NJ-78-12 at the higher dose inhibited the cancer cell lines, but at none of the doses affected the normal tissue WI-38 cell line. Thus, this compound is specific and lacks a general toxicity to cells or tissue. MT-133-3 behaved similar to NJ-78-12 except that it inhibited WI-38 growth. NJ-81-4 also did very nicely giving good inhibition of cancer cells but not the WI-38 cells.

Curcumin Derivatives Diacetyl Curcumin (NJ-58-1) and Curcumin-Glutarate (MT-76-1):

The curcumin levels of inhibition were generally higher than NJ-58-1 and MT-76-1. An exception was with skbr3 breast cancer cells at 300 uM. All three compounds gave a similar response at 24 hours with skbr3. At 24 hours, NJ-58-1 was more specific to cancer cells than curcumin. The $IC_{50}$ data for 24 and 48 hour time points is shown in Tables 8 and 12. At 24 hours, NJ-58-1 did very well in inhibiting PANC-1 and PC-3 at doses greater than 50 uM. It inhibited skbr3 cancer lines at greater than 150 uM doses. MT-76-1 at 24 hours behaved similarly except that at the lower doses it more specifically inhibited the PANC-1 cell line. Both compounds at 24 hours didn't have a very significant affect on the WI-38 cell line, which is a normal cell line, i.e. not a cancerous cell line. At 24 hours with NJ-58-1, normal lung cells (WI-38) actually grew or were inhibited less than 10%, while with curcumin levels of inhibition at 100, 150 and 300 uM were just over 20%. Accordingly, these results demonstrate that NJ-58-1 is more specific than MT-76-1 and curcumin because normal cells behaved similar to cancer cells treated with curcumin.

Example 8

Evaluation of Anti-Cancer Activity of Compounds

The following compounds and combinations were used in this experiment: Gemcitabine.HCl (NJ-92-1), MT-133-3 (NJ-92-2), Gemcitabine.HCl (2 mg)+MT-133-3 (20 mg) (NJ92-3), Paclitaxel (NJ-92-4) and Paclitaxel 2 mg+MT-133-3 (20 mg) (NJ-92-5).

Determine LD50 (Lethal Dose, 50%) of Testing Compounds:

Cytotoxicity of the compounds on three different cancer cell lines and one normal cell line was tested. Four human cell lines including both cancer cell lines (SK-BR-3, PANC-1, PC3) and normal cell line (WI38) were initially employed. The cells (20,000 cells/well) were plated onto a 96-well plate for 24 hours before treatment. The compounds were diluted in the medium and added to the cells at different concentrations for additional 24 hours from 1 ng/ml to 10 ug/ml. MTT assay was then performed.

LD50 was not observed for all these compounds under testing concentrations, demonstrating that these compounds do not have cytotoxicity under the testing conditions (FIGS. 26A-26D).

Determination of Inhibitory Effect of Compounds on Cell Proliferation:

The compounds were tested for cancer cell proliferation inhibition. Based on the data derived from in vitro cytotoxicity, evaluation of cell proliferation was under taken. Four cell lines were plated onto a 96 well plate for 24 hours before adding the compounds. Two different doses (20 ng/ml and 2,000 ng/ml) were employed up to 8 days followed by MTT assay. DMSO and Taxol were used as negative control and positive controls. Results are shown in FIGS. 27A-27D.

Compound #5 (NJ-92-5) displayed inhibitory effect on PANC-1 cell proliferation after 48 h treatment; the compound #5 inhibited PC3 cell proliferation at early treatment, similar to Taxol; the compound #5 showed cytotoxicity on SK-BR-3 cells. No significant difference of Compound #5 was noted on normal WI38 cells.

Compound #3 (NJ-92-3) had minimal effect on cancer cell proliferation. Significant effect occurred only under high concentration (2,000 ng/ml).

These results indicate that the mechanism of action of compound #5 (NJ-92-4) is through inhibition of cancer cell proliferation, but not cytotoxiticy.

Determination of $GI_{50}$ (50% Inhibition of Cell Growth):

Since the compounds displayed inhibitory effect on cell proliferation, a $GI_{50}$ experiment was performed. The cells were plated onto a 96 well plate and treated with different concentrations of the compounds from 1 ng/ml to 10 ug/ml for 72 hours followed by MTT assay. The results are shown in FIGS. 28A-28D and $GI_{50}$ values summarized in Table 15.

TABLE 15

$GI_{50}$ values of compounds for various cell lines

| Cell line | NJ-92-1 | NJ-92-2 | NJ-92-3 | NJ-92-4 | NJ-92-5 |
|---|---|---|---|---|---|
| PANC-1 | 7180 ng/ml | 5641 ng/ml | 6411 ng/ml | 1.8 ng/ml | 0.6 ng/ml |
| PC3 | 3847 ng/ml | 4616 ng/ml | NA | 258 ng/ml | 6923 ng/ml |
| SK-BR-3 | NA | 9743 ng/ml | 9999 ng/ml | 1.15 ng/ml | 0.25 ng/ml |
| WI38 | NA | 5385 ng/ml | 6411 ng/ml | 514 ng/ml | 2052 ng/ml |

Example 8

In Vivo Effect of Curcumin, Turmeric Oil and Fish Oil Combinations

Materials and Methods: The study protocol was approved by IAEC. Albino rats obtained from the central animal house of the institute were used in the study. The animals were kept under 12 hour day night cycle. Animals were given standard diet and water was provided ad libitum. All animals were acclimatized for at least one week before the experimental session.

Animals were divided into eight groups in the carrageenan induced paw edema and tail flick method. Each group consisted of 6 animal each. The groups received various chemicals as given in Table 16 by oral administration with food. The following methods were used to evaluate the activity of the compositions:

Carrageenan Induced Rat Paw Edema:

Pedal inflammation in albino rats of either sex was produced according to the method of Winter et al. (*Proc. Soc. Exp. Biol. Med.*, 1963, 111: 544-547). An injection was made with 0.1 ml of 1% carrageenan (SIGMA) suspension into the right hind foot of each rat in the plantar region. The various chemicals were given 30 minutes before carrageenan injection. Increase in linear paw circumference was measured by tying a piece of cotton thread round the rat's paw, and noting the point of intersection of two ends on a meter scale. This was taken as an index of increase in paw volume, which is a measure of edema (Bamgbose, S. O. A. & Noamesi, B. K., *Planta. Med.*, 1981, 42: 392-396). Measurements were taken immediately before and at 1, 2 and 3 hours after carrageenan injection. The inhibitory activity was calculated according to the following formula (Awe S O, Olajide O A, Adeboye J O, Makinde J M. *Indian J. Pharmacol.*, 1998; 30: 38-42):

$$\text{Percent inhibition} = \frac{(Ct - Co)\ \text{control} - (Ct - Co)\ \text{treated}}{(Ct - Co)\ \text{control}} \times 100$$

Ct-Linear paw circumference 3 hours after carrageenan injection and Co-Linear paw circumference before carrageenan injection.

Tail flick test: Analgesic activity was measured by the tail flick method, using the analgesiometer (Techno, Lucknow, India) as described by D'Armour and Smith (*J. Pharmacol. Exp. Ther.*, 1941, 72: 74-79). Rats were screened for tail flip reaction with a cut-off time of 5 seconds. For each animal, the tail flick latency was obtained thrice before drug administration and mean was used as pre-drug latency. The tail flick latencies were measured at 0, 0.5, 1, 1.5, 2 and 3 h after administration of chemicals. For animals that did not respond within the cut-off time of 10 seconds, the value of the cut-off time was considered as latency period for that animal (Ramabadran, K. & Bansinath, M. *Pharmaceutical. Res.*, 1986, 3: 263-270).

Results are expressed as % maximum possible effect (MPE) (Bishnoi, et al., *Indian J. Pharmacol.*, 2005, 37: 255-256)

$$\% MPE = \frac{(\text{post treatment latency} - \text{pretreatment latency})}{\text{Pretreatment latency}} \times 100$$

Statistical Analysis:

Data were analyzed using analysis of variance (ANOVA) and t-test. $P < 0.05$ was considered as statistically significant.

TABLE 16

| Groups | Drug | Dose/volume |
|---|---|---|
| 1 | Normal saline | 0.3 ml |
| 2 | Curcumin | 100 mg/kg |
| 3 | Curcumin + fish oil (1:1) | 100 mg/kg |
| 4 | Curcumin + turmeric oil, BR-132-4 (1:1) | 100 mg/kg |
| 5 | Curcumin + fish oil + lecithin (4:2.5:1) | 100 mg/kg |
| 6 | Turmeric oil fraction, BR-132-4 | 100 mg/kg |
| 7 | Aspirin | 100 mg/kg |
| 8 | Sod. Bicard. | 0.3 ml |

Figure 30:
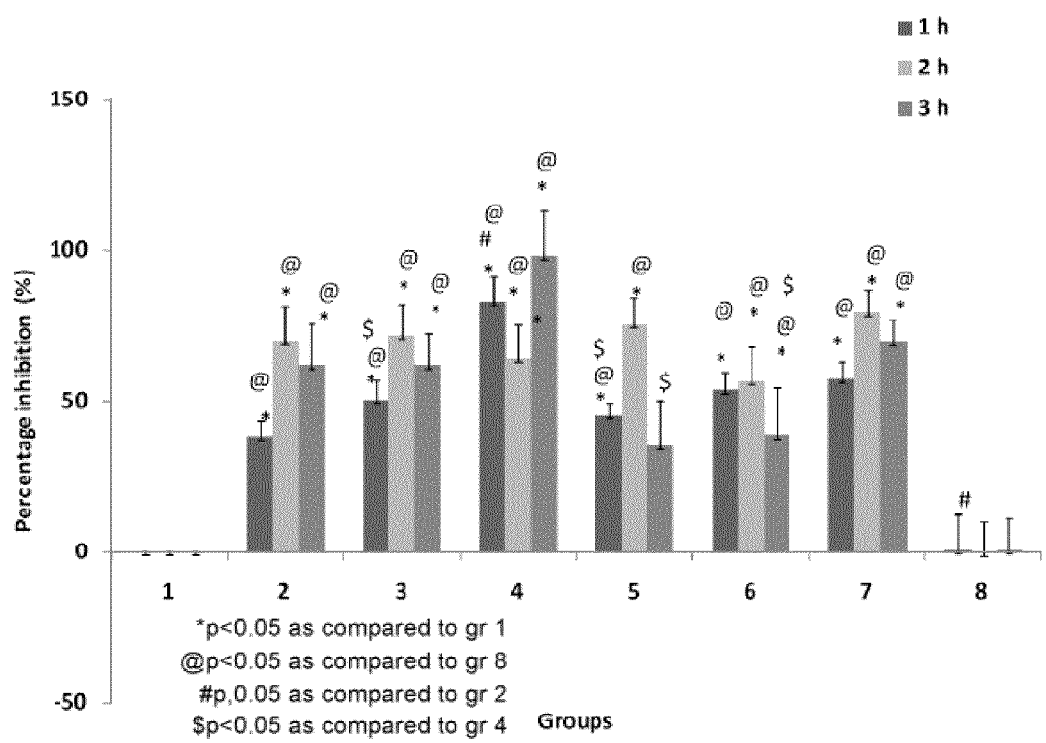
FIG. 30 is a bar graph showing % inhibition of paw edema.

Results for paw edema inhibition are shown in Table 17 and FIG. 30. For paw edema inhibitory activity curcumin and turmeric oil mixture (group 4) at 1 and 3 hours exhibited the maximum activity at a dose of 50 mg/kg for each of the compounds and this was higher than that of curcumin (group 2) and turmeric oil (group 6) alone at 100 mg/kg doses. At 2 hours a combination of curcumin, fish oil and lecithin (group 5) in which curcumin is ~53 mg/kg, had stronger activity than that of curcumin alone at 100 mg/kg. At all time points the combination of curcumin and fish oil (group 3) in which curcumin was at 50 mg/kg, had similar or slightly stronger activity than curcumin at 100 mg/kg.

TABLE 17

Paw circumference (mm) in various groups

| Groups | 0 h | 1 h | 2 h | 3 h |
|---|---|---|---|---|
| 1 | 3.17 | 3.77 | 3.45 | 3.5 |
| 2 | 3.2 | 3.68 | 3.45 | 3.53 |
| 3 | 3.37 | 3.53 | 3.68 | 3.39 |
| 4 | 3.17 | 3.7 | 3.38 | 3.73 |
| 5 | 3.17 | 3.57 | 3.5 | 3.65 |
| 6 | 2.47 | 3.43 | 3.35 | 3.33 |
| 7 | 3.4 | 3.82 | 3.58 | 3.67 |
| 8 | 2.47 | 3.43 | 3.35 | 3.33 |

*$p < 0.05$ as compared to 0 hour- in all significant except at 1 hour in group 4

Figure 31:
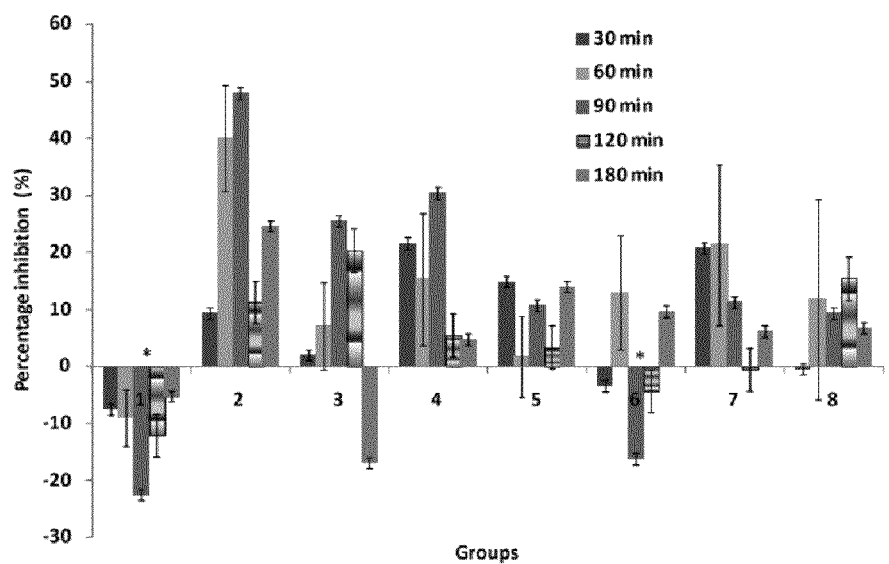
FIG. 31 is a bar graph showing % MPE in tail flick test with controls. *P<0.05 as compared to Group 2.
Figure 32:
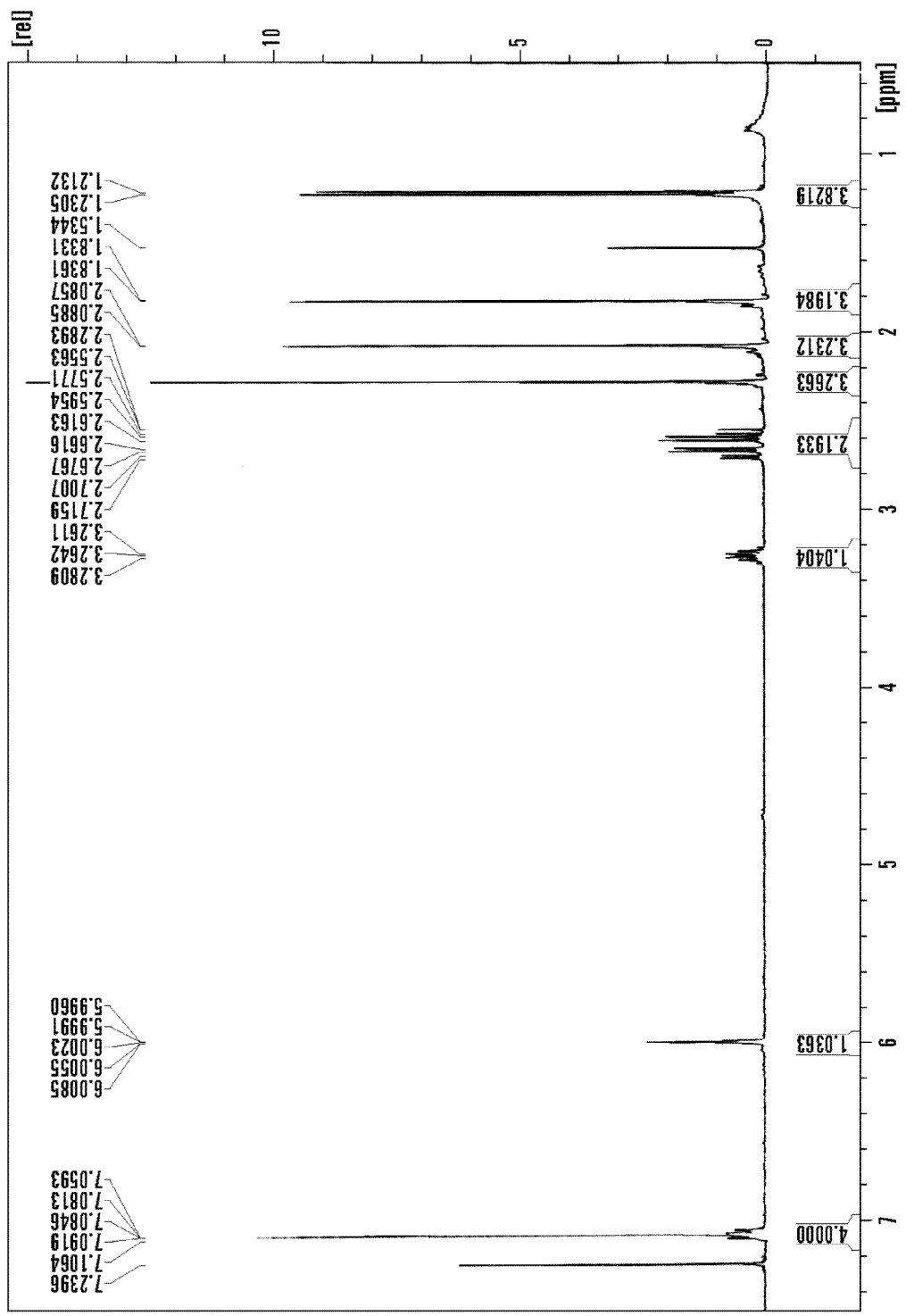
FIGS. 32-38 show the NMR spectra of turmeric oil extract fractions NJ-106-1 (FIG. 32), NJ-106-1 (FIG. 33), MT-133-1 (FIG. 34), MT-133-3 (FIG. 35), MT-133-4 (FIG. 36), MT-133-5 (FIG. 37), and MT-133-8 (FIG. 38).
Figure 33:
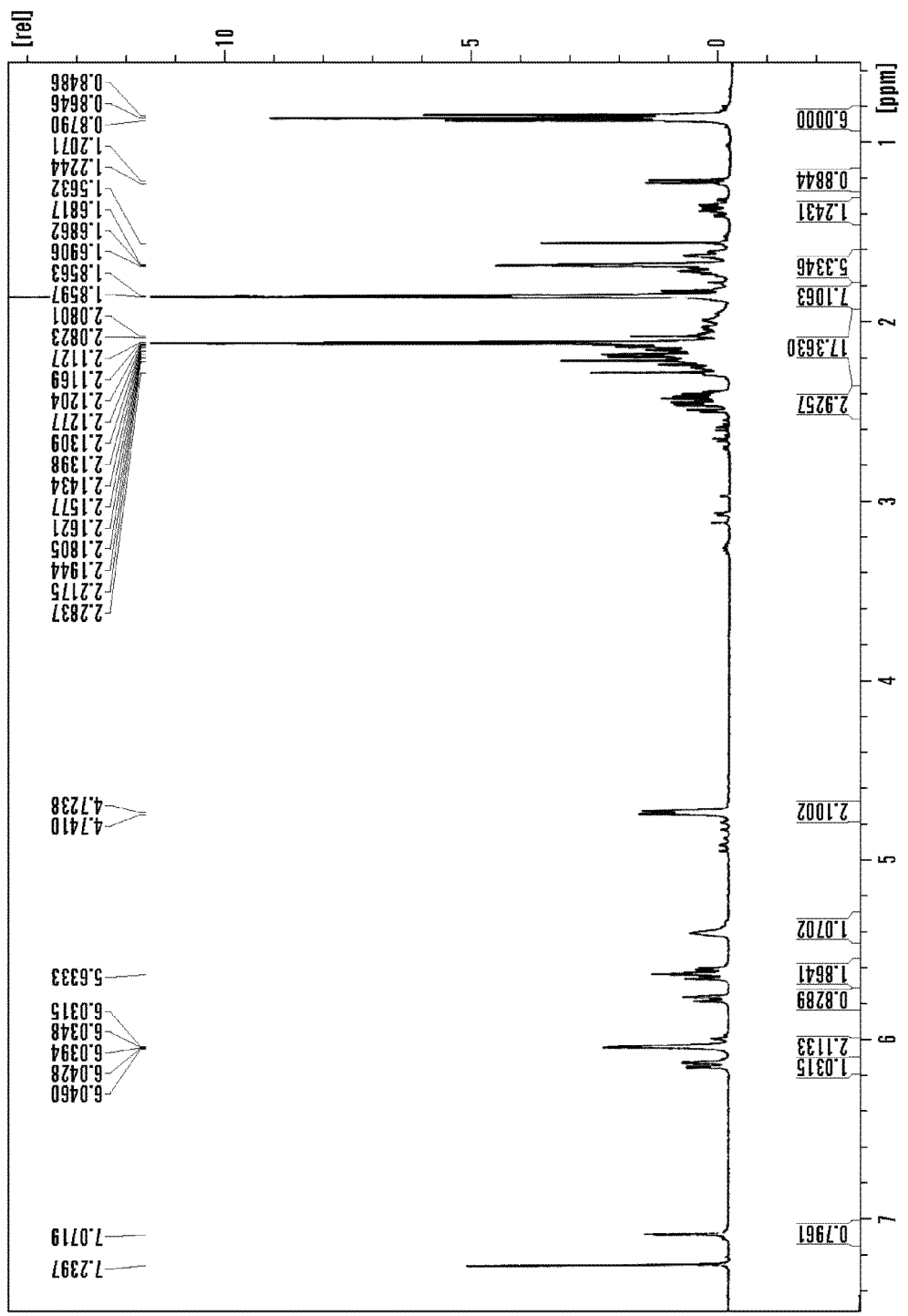
Figure 34:
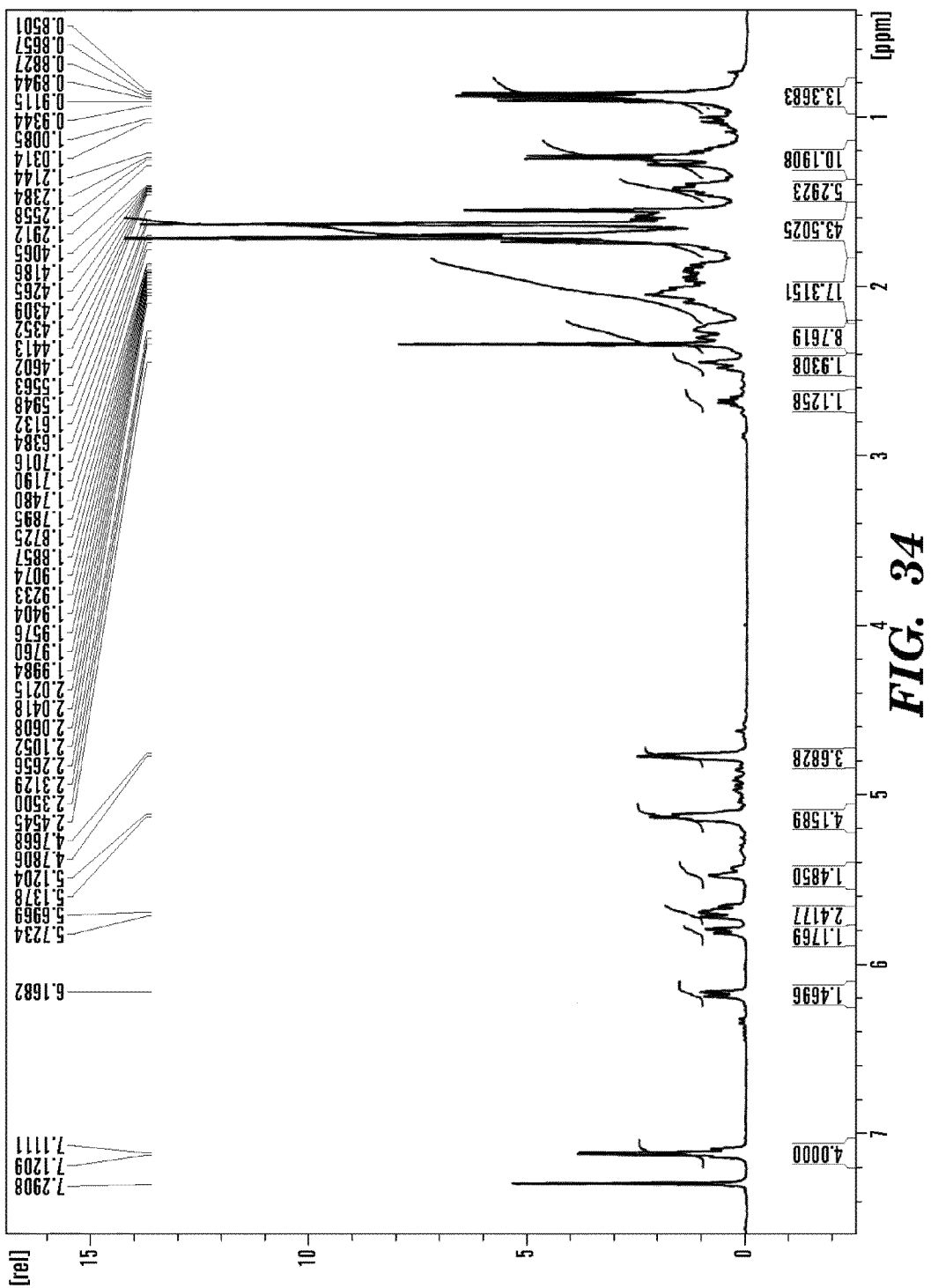
Figure 35:
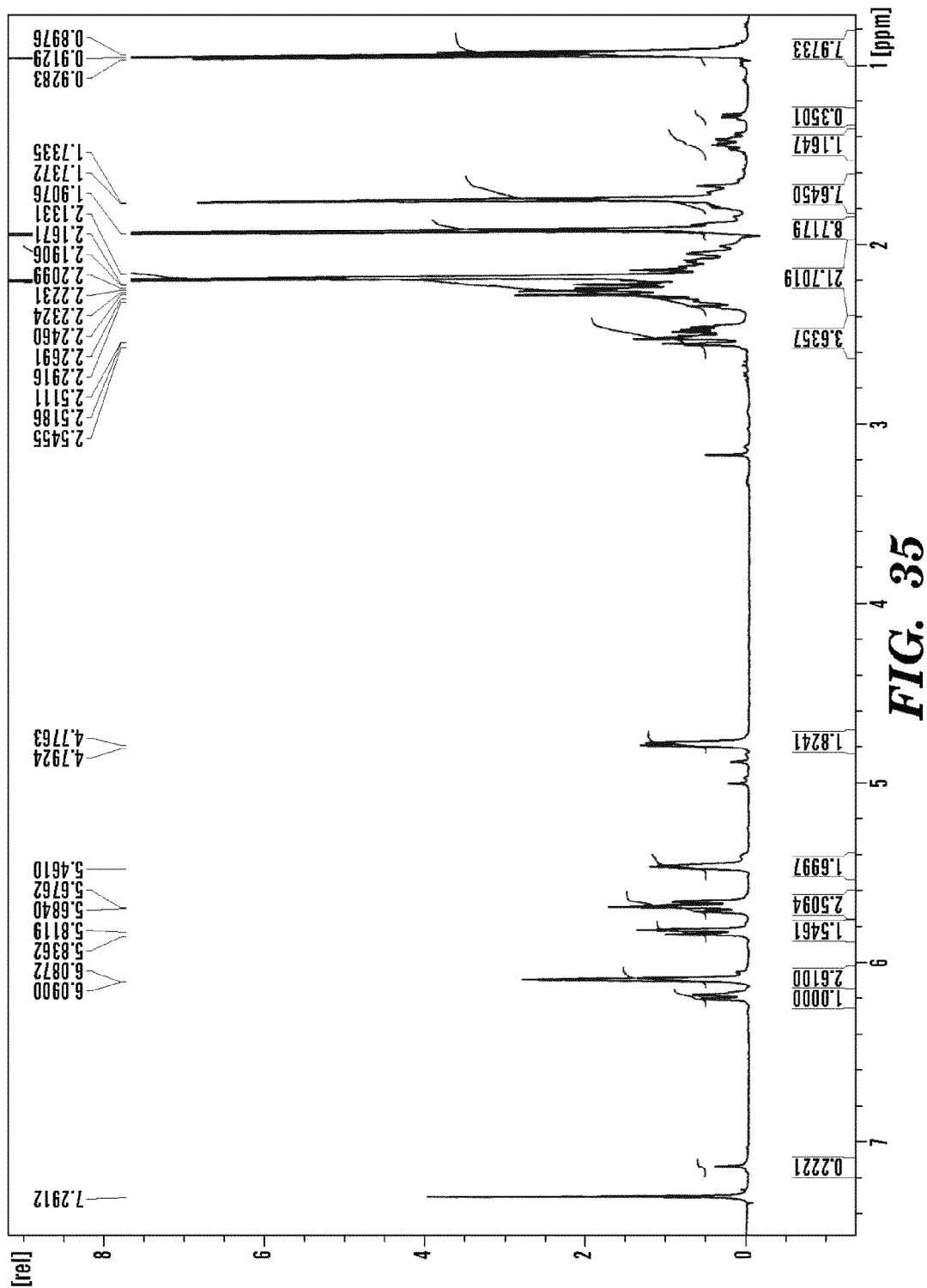
Figure 36:
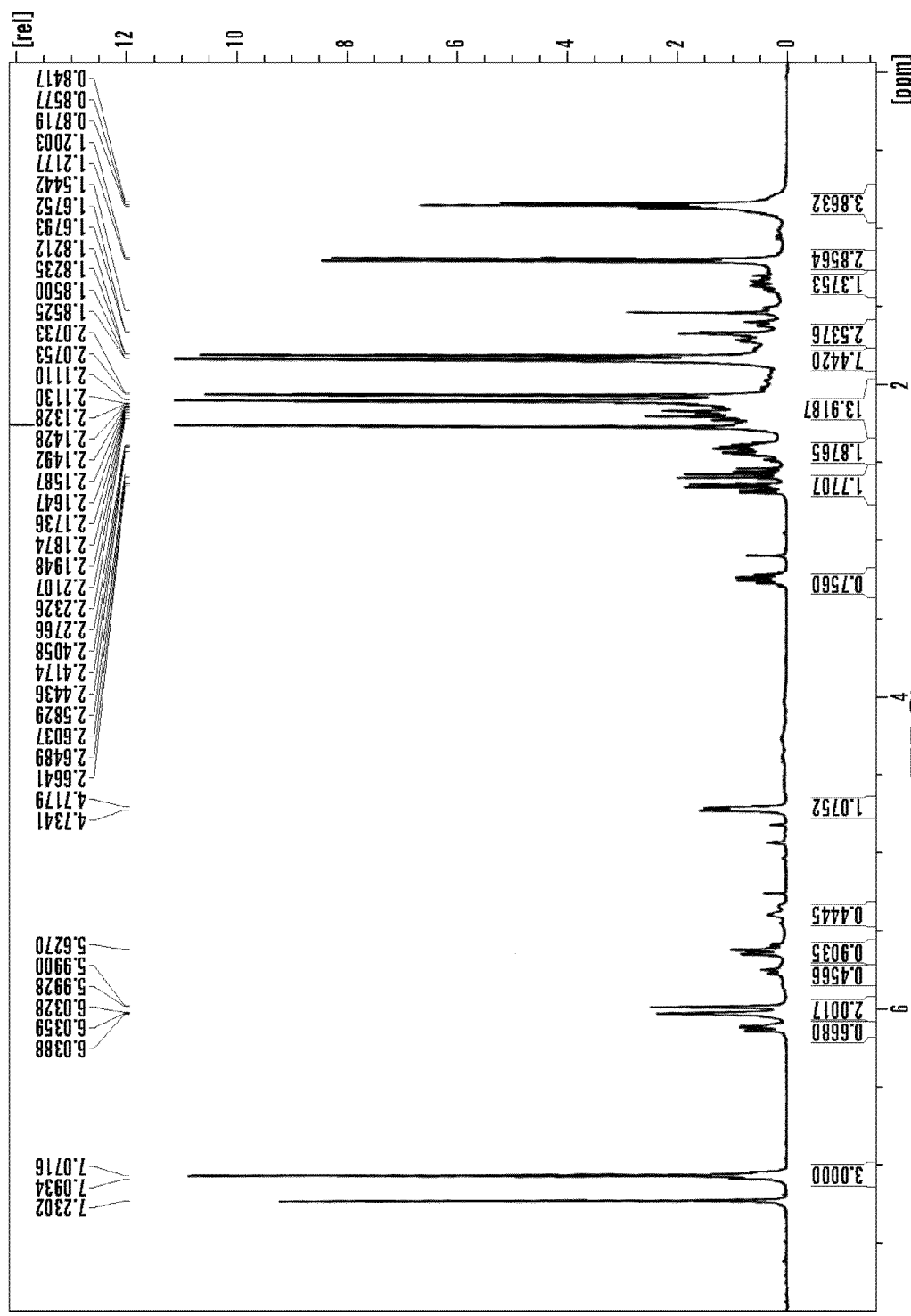
Figure 37:
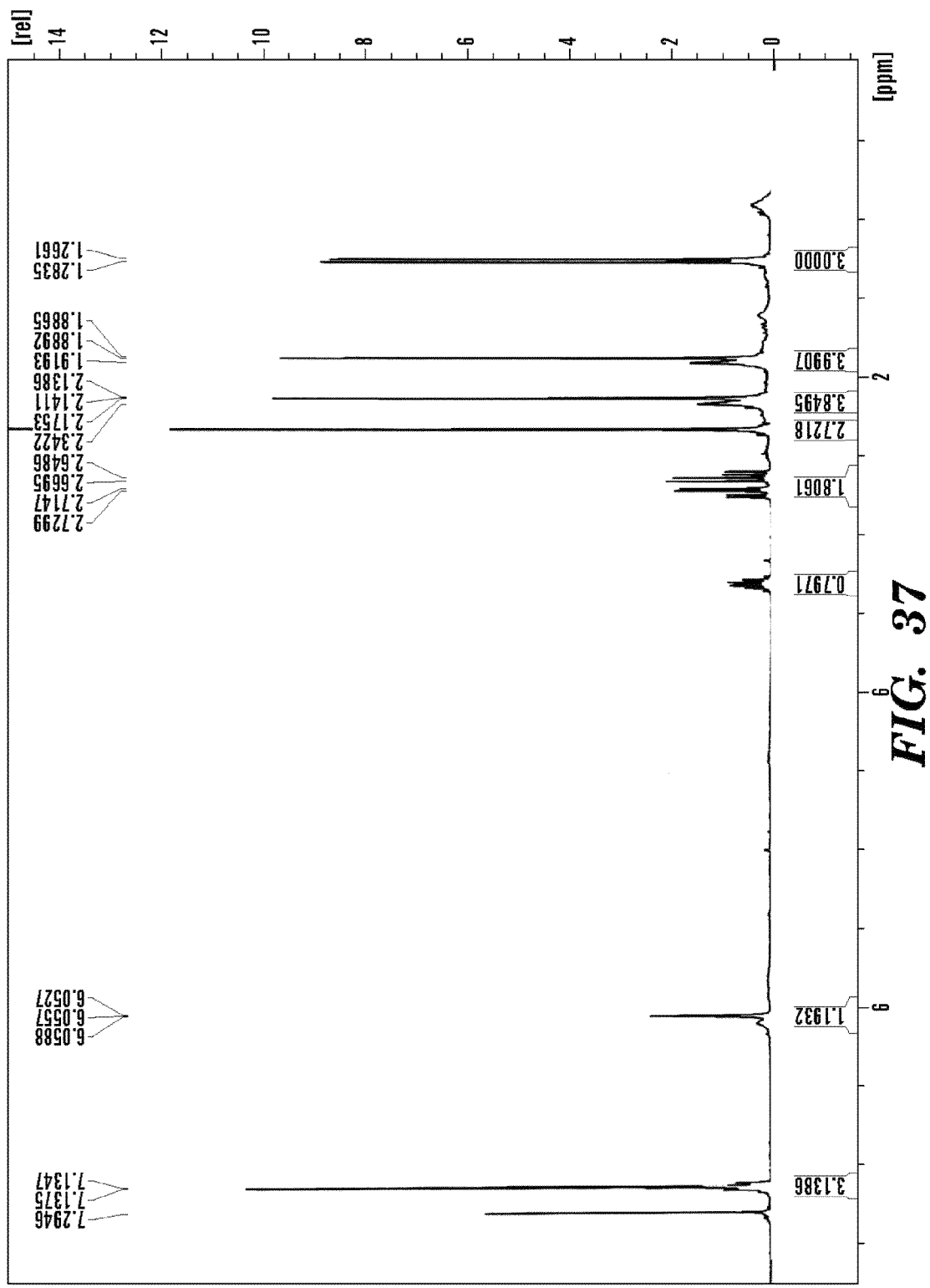

Results for tail flick latency are shown in Table 18 and FIG. 31. For tail flick experiment curcumin at 100 mg/kg had stronger activity at 60 and 90 minutes compared to the other drugs while the combination of curcumin and turmeric oil fraction at 50 mg/kg each had higher activity than turmeric oil or aspirin alone at 100 mg/kg at 90 minutes.

TABLE 18

Tail flick latency time (seconds) in various groups
(*$p < 0.05$ as compared to 0 minutes)

| Groups | 0 min | 30 min | 60 min | 90 min | 120 min | 180 min |
|---|---|---|---|---|---|---|
| 1 | 2.19 | 2.4 | 3.07 | 3.23* | 2.47* | 2.68 |
| 2 | 2.67 | 2.58 | 2.8* | 3.18* | 3.03 | 2.68 |
| 3 | 2.17 | 2.5 | 2.4 | 2.68 | 2.15 | 2.18 |
| 4 | 2.48 | 2.87 | 2.5 | 2.77 | 2.57 | 2.83 |
| 5 | 2.48 | 2.38 | 2.75 | 2.07 | 2.38 | 2.77 |
| 6 | 1.75 | 1.9 | 1.88 | 1.58 | 1.87 | 1.93 |
| 7 | 2.37 | 2.75* | 2.68 | 2.57 | 2.23 | 2.37 |
| 8 | 2.87 | 2.67 | 2.97 | 2.88 | 3.05 | 2.82 |

These data show that the combination of curcumin and fish oil at 50 mg/kg each had strong anti inflammatory activity while curcumin and turmeric oil combination acted as analgesic at 50 mg/kg under the experimental conditions used.

Example 9

Comparison of Anti-Inflammatory and Analgesic Activities of Fish Oil, Turmeric Oil, Curcumin Diacetate, Curcumin Diglutarate and Aspirin Fish oil, a distillation fraction of turmeric oil and two derivatives of curcumin (NJ-104-1 to NJ-104-5) were used in this study to determine the anti-inflammatory and analgesic activities of these drugs by oral administration and these were compared to aspirin. Anti-inflammatory was evaluated by carrageenan induced paw edema and analgesic activity by tail flick method in rats.

Albino rats obtained from the central animal house of the institute were used in the study. The animals were kept under 12 hour day night cycle. Animals were given standard diet and water was provided ad libium. All animals were acclimatized for at least one week before the experimental session.

Animals were divided into six groups in the carrageenan induced paw edema and tail flick method. Each group consisted of 8 animals each. The groups received various drugs orally mixed with food, as given in Table 19. Carrageenan-induced rat paw edema and Tail flick test were performed as discussed above in Example 8. Data were analyzed using analysis of variance (ANOVA) with Posthoc Bonferroni multi-comparisons. $P<0.05$ was considered as statistically significant.

TABLE 19

Drugs given to various groups

| Group | Drug | Dose/Volume |
|---|---|---|
| 1 | Normal Saline | 0.3 mL |
| 2 | NJ-104-1 (Fish oil) | 100 mg/kg |
| 3 | NJ-104-2 (Turmeric oil fraction, NJ-100-9) | 100 mg/kg |
| 4 | NJ-104-3 (Fish oil + turmeric oil fraction NJ-100-9) (1:1) | 100 mg/kg |
| 5 | NJ-104-4 (Curcumin diacetate) | 100 mg/kg |
| 6 | NJ-104-5 (Curcumin diglutarate) | 100 mg/kg |
| 7 | Aspirin | 100 mg/kg |

NJ-100-9: Turmeric oil distillation fraction which distilled mostly at 105 to 118° C./high vacuum Carrageenan-induced hind paw edema is the standard experimental model of acute inflammation. Carrageenan is the agent of choice for testing anti-inflammatory drugs as it is not known to be antigenic and is devoid of apparent systemic effects. Moreover, the experimental model exhibits a high degree of reproducibility (Winter, et al., *Proc. Soc. Exp. Biol. Med.*, 1962; 111: 544-547). Carrageenan-induced edema is a biphasic response. The first phase is mediated through the release of histamine, serotonin and kinins whereas the second phase is related to the release of prostaglandin and slow reacting substances which peak at 3 hour (Vinegar R, Schreiber W, & Hugo R., *J. Pharmacol. Exp. Ther.*, 969; 166: 96-10). The increase in the paw volume following carrageenan administration in the control and aspirin treated group corresponds with the findings of previous workers (Jana U, Chattopadhyay R N, & Shaw B P, *Indian J. Pharmacol.*, 1999; 31: 232-3 and Singh R K & Pandey B L. *Indian J. Physiology Pharmacol.*, 1996; 40: 355-8).

Figure 38:
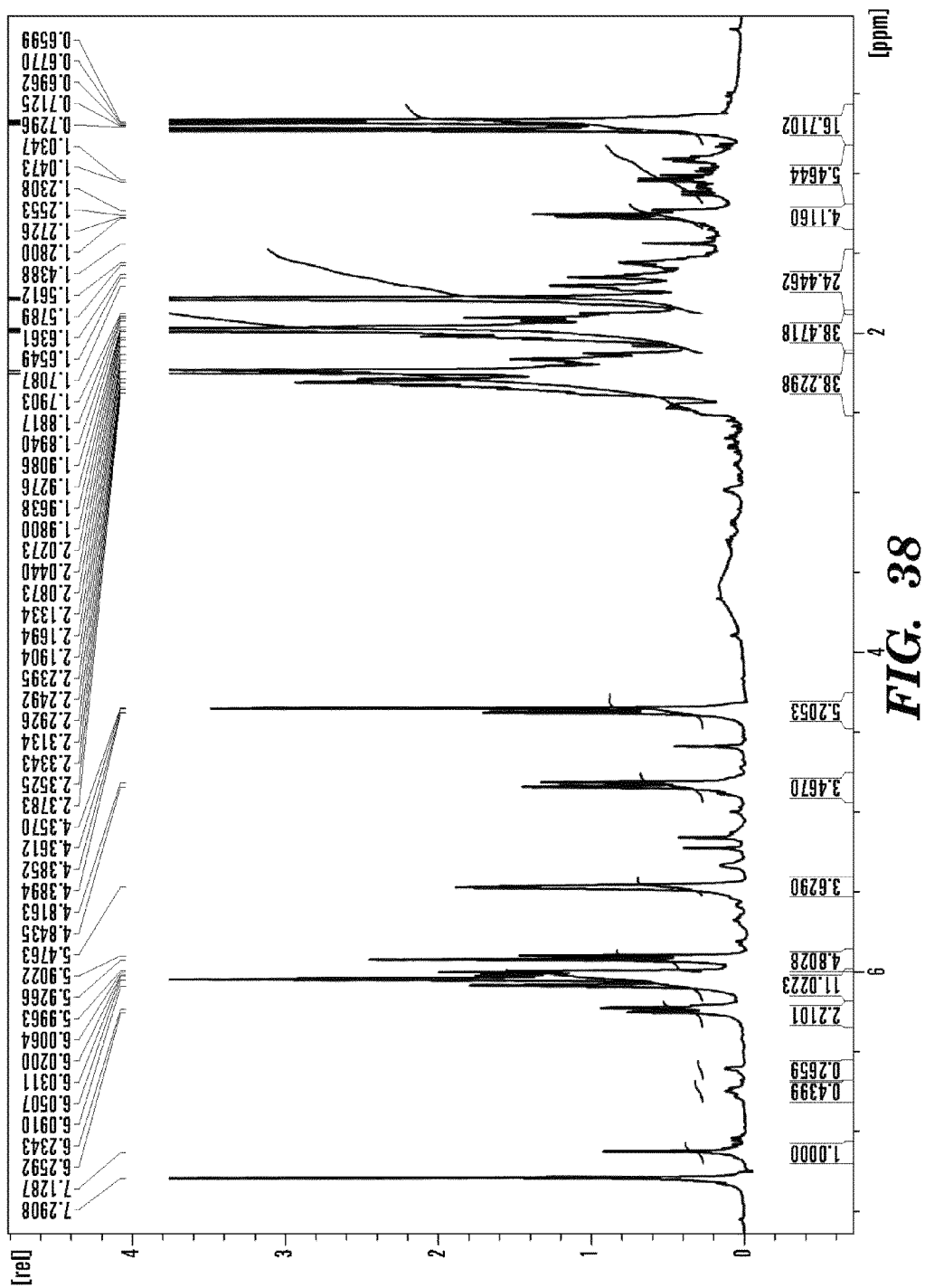
Figure 39:
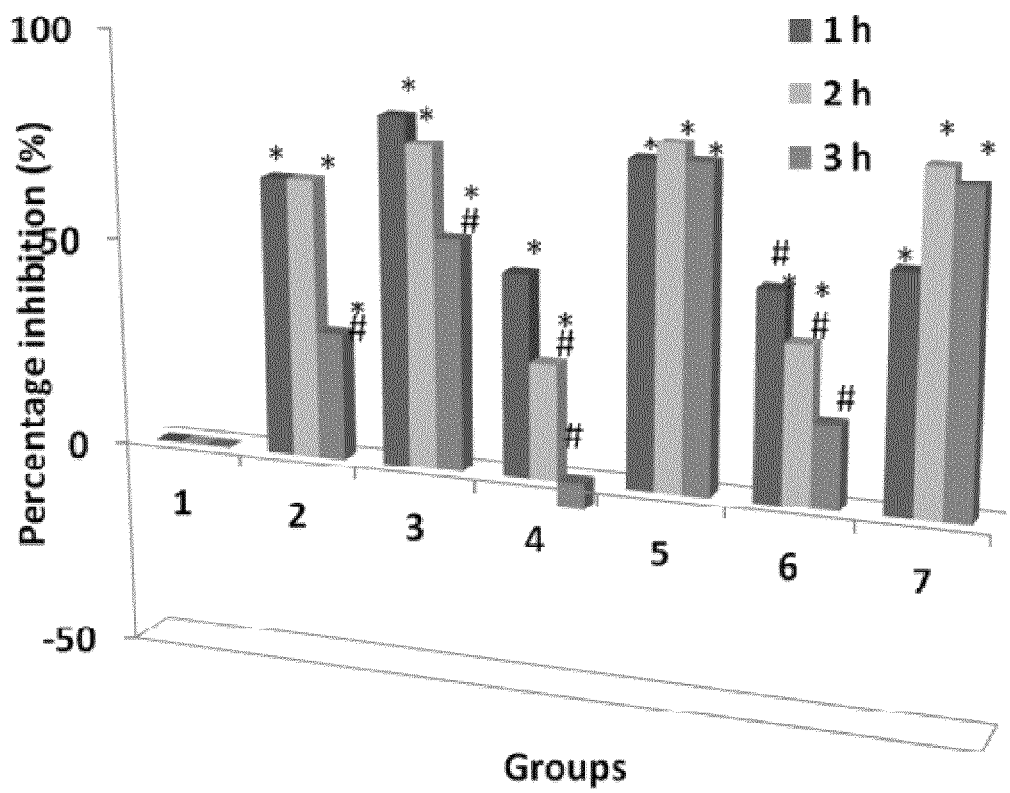
FIG. 39 is a bar graph showing % inhibition of paw edema.

Results for the Carrageen-induced paw edema assay are shown in Table 20 and FIG. 38. Anti-inflammatory activity study at 100 mg/kg showed that turmeric oil distillation fraction, NJ-100-9, had 82% and 76% inhibition of paw edema at 1 hour and 2 hours after drug administration. Curcumin diacetate was active at all three time points, (1 hr, 2 hr and 3 hr) by 76, 80 and 76% respectively. Fish oil inhibited paw edema by 66% at the initial time periods and went down to 30% by hour 3. Curcumin diglutarate and the mixture of fish oil and turmeric oil showed only modest activities (below 50%) at this dose.

TABLE 20

Percent inhibition of paw edema

| | Percent Inhibition (Std. Error) | | |
|---|---|---|---|
| Group | 1 hr | 2 hr | 3 hr |
| 1 | 0 | 0 | 0 |
| 2 | 66.58 (6.46) | 66.67 (9.38) | 30.23 (5.37) |
| 3 | 82.67 (3.10) | 76.39 (3.89) | 54.94 (5.12) |
| 4 | 48.12 (8.91) | 27.78 (9.14) | −6.10 (9.43) |
| 5 | 76.49 (8.35) | 80.56 (5.84) | 76.74 (8.22) |
| 6 | 49.26 (3.94) | 37.50 (5.11) | 20.05 (8.34) |
| 7 | 55.44 | 79.16 | 75.29 |

Figure 40:
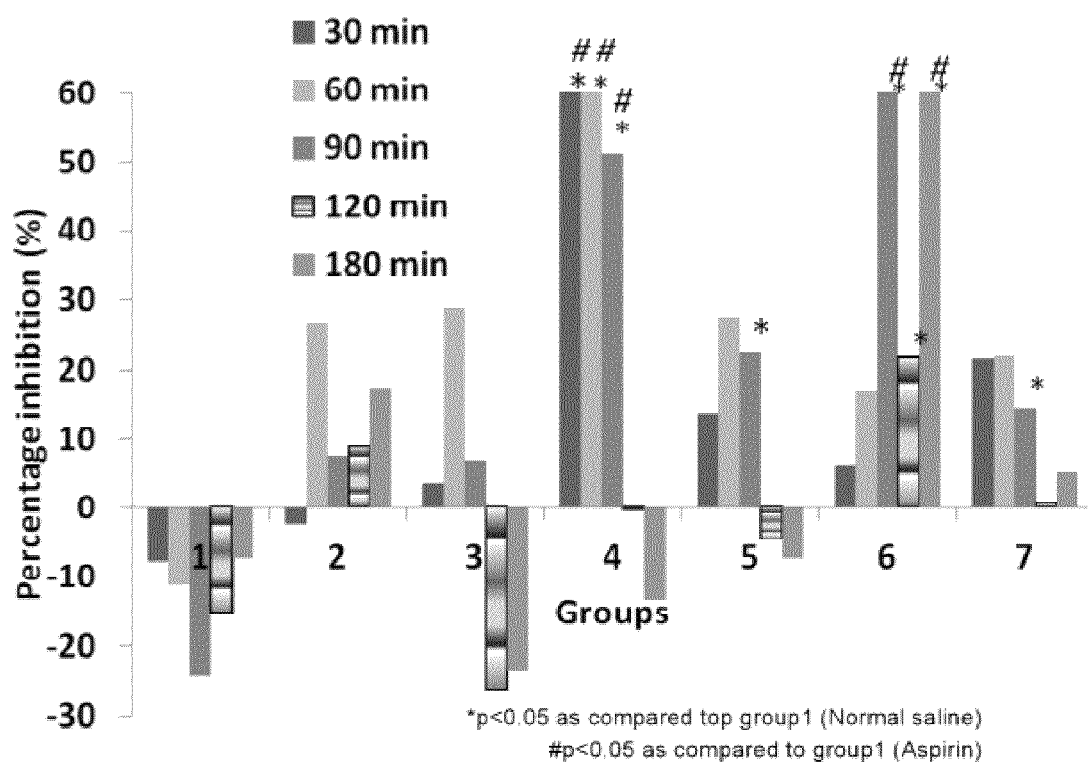
FIG. 40 is a bar graph showing % M PE in tail flick test with controls. MPE: P<0.05 as compared to control, at 60 min—with 4, 5, 6; at 90 min—with 6; at 120 min—with 6; at 180 min—with 6.
Figure 41:
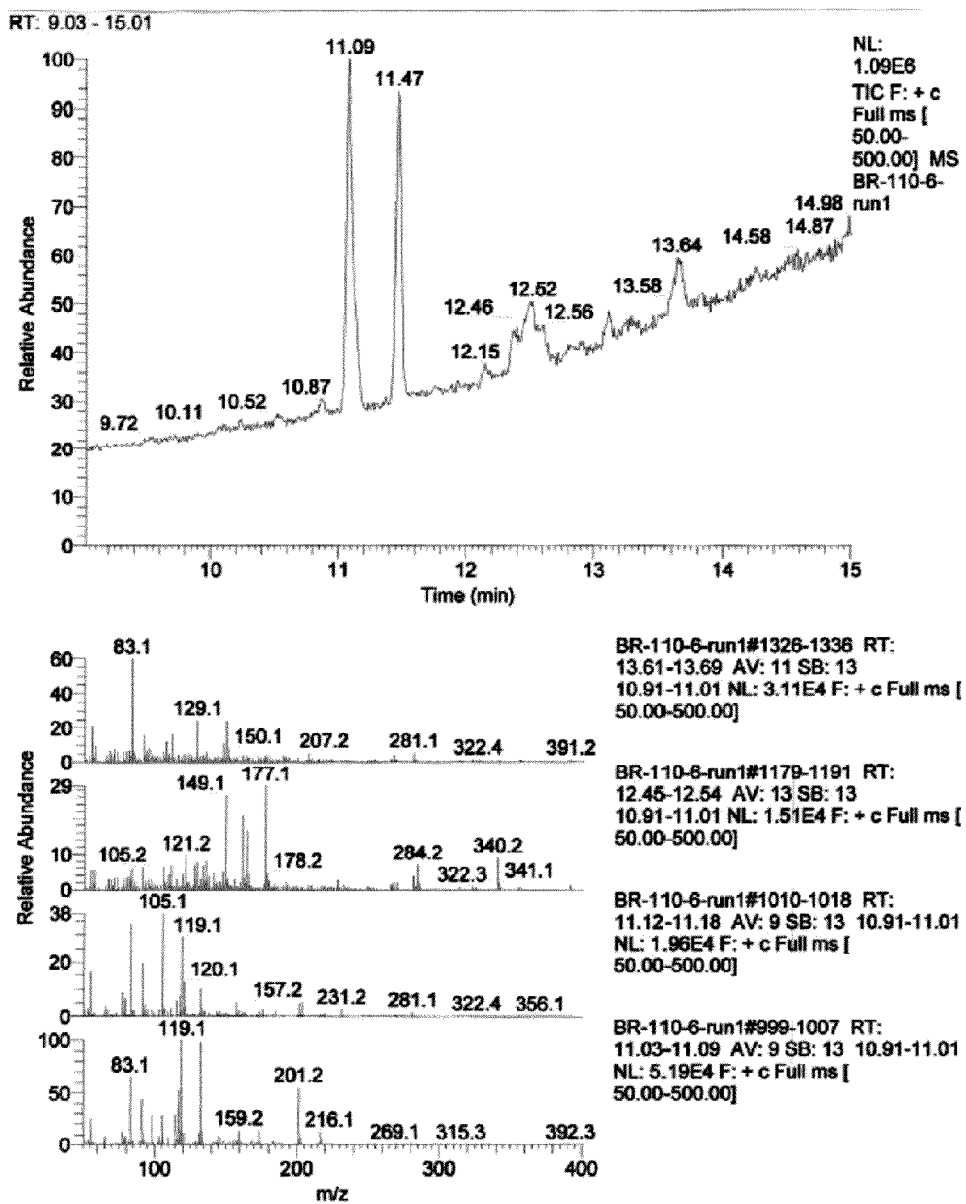
FIGS. 41-43 show GC mass spectra of turmeric oil extract fraction BR-110-6.
Figure 42:
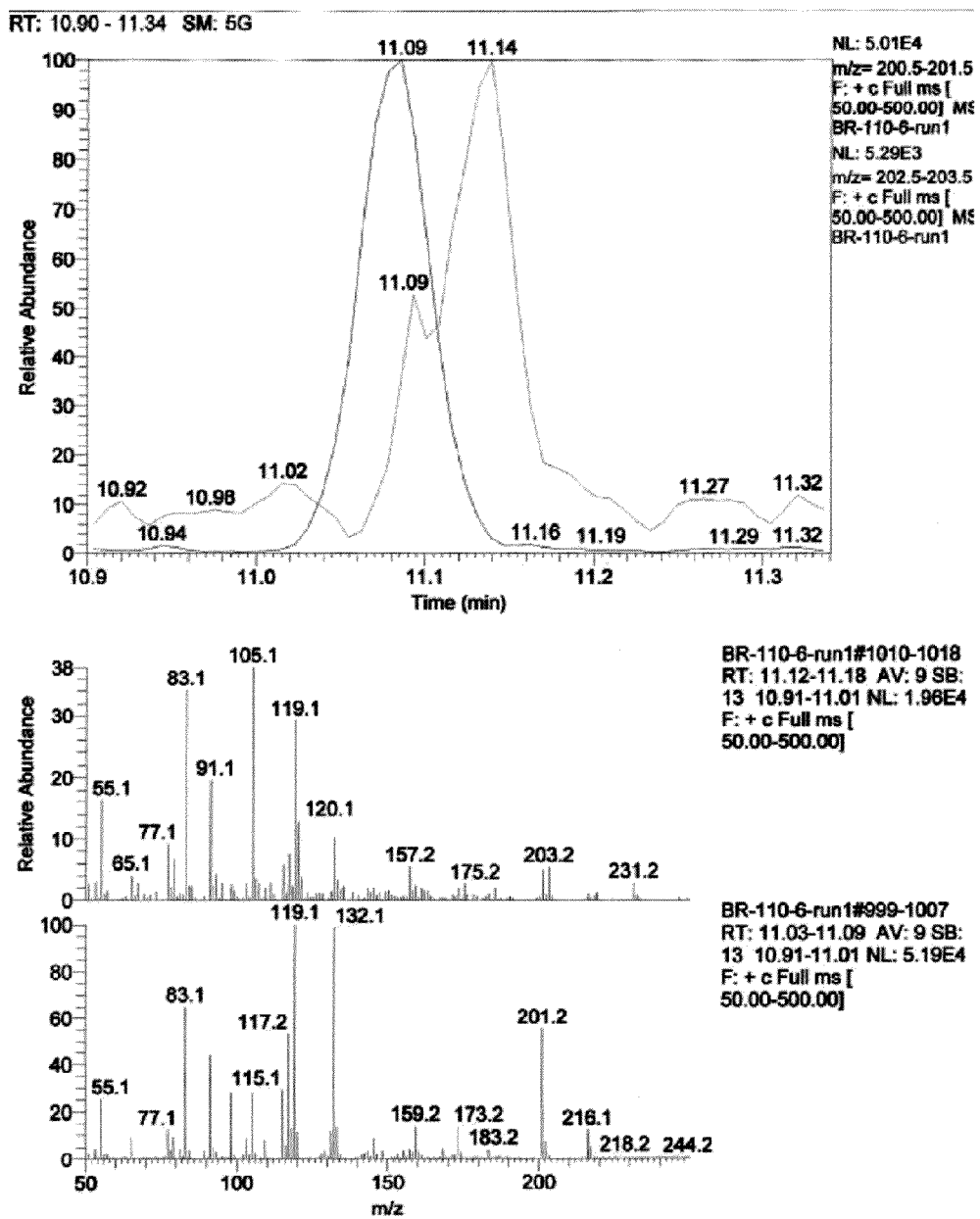
Figure 43:
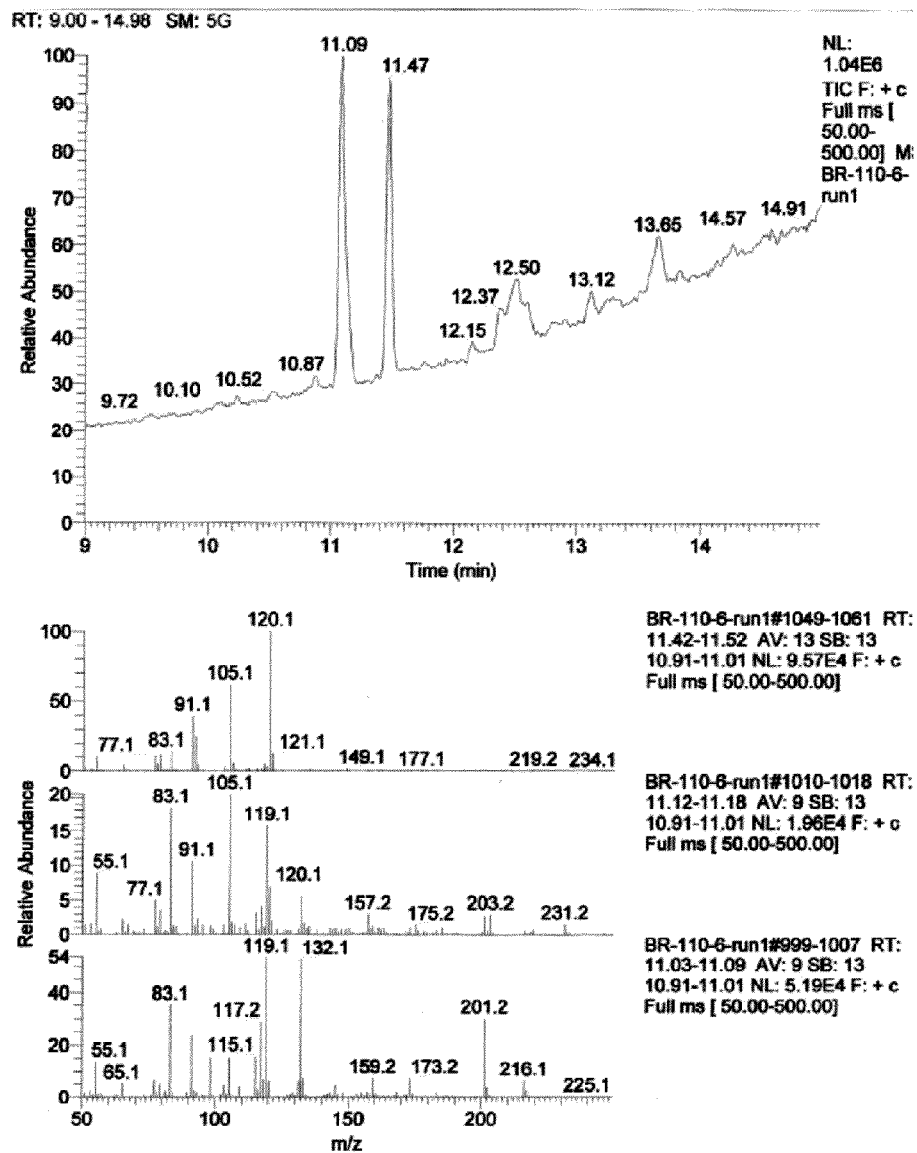
Figure 44A:
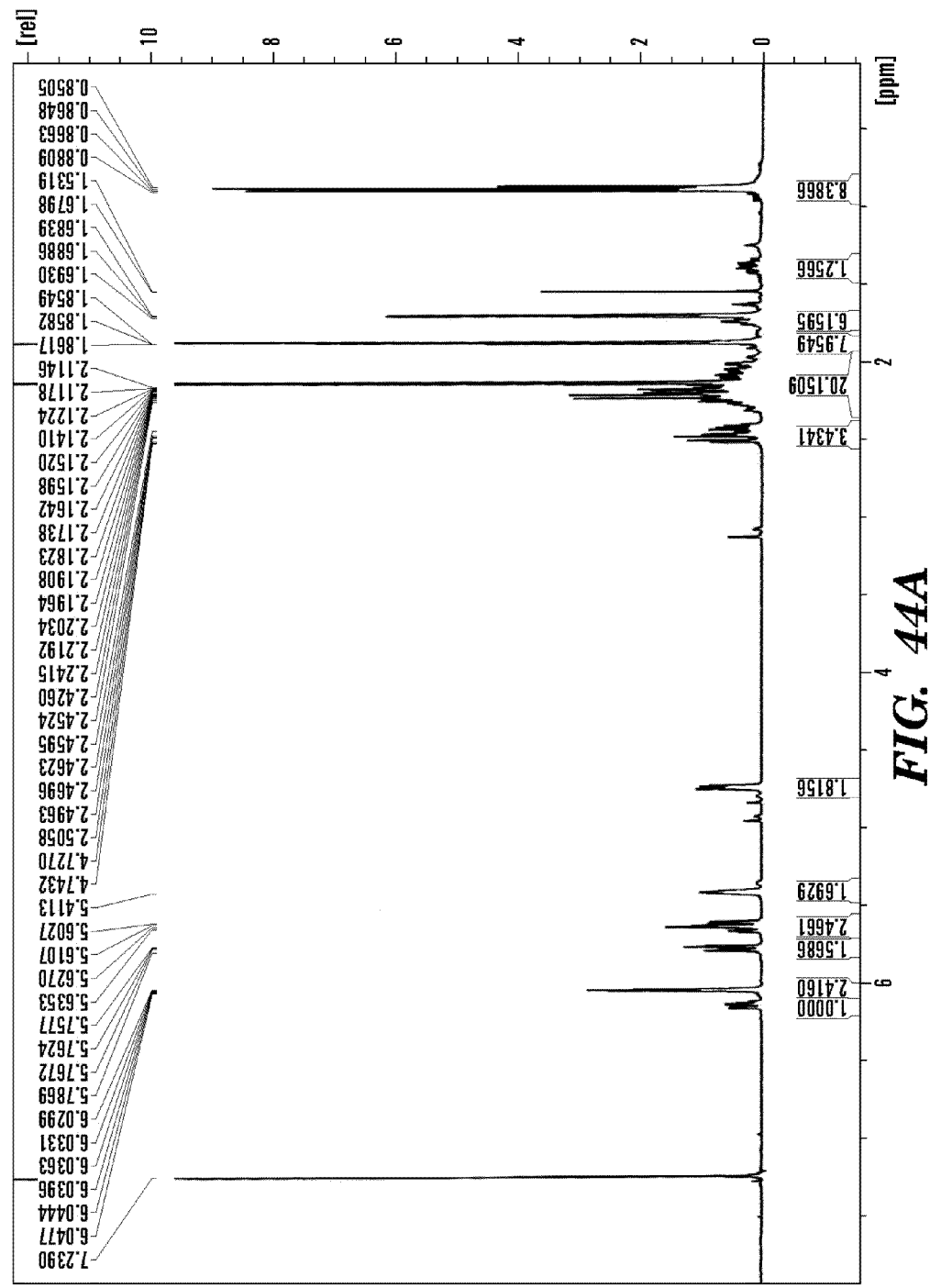
FIGS. 44A and 44B show the NMR spectra of the two fractions obtained from the turmeric oil extract fraction BR-110-4 after passing through a silica gel column and eluting with ethyl acetate and hexane.
Figure 44B:
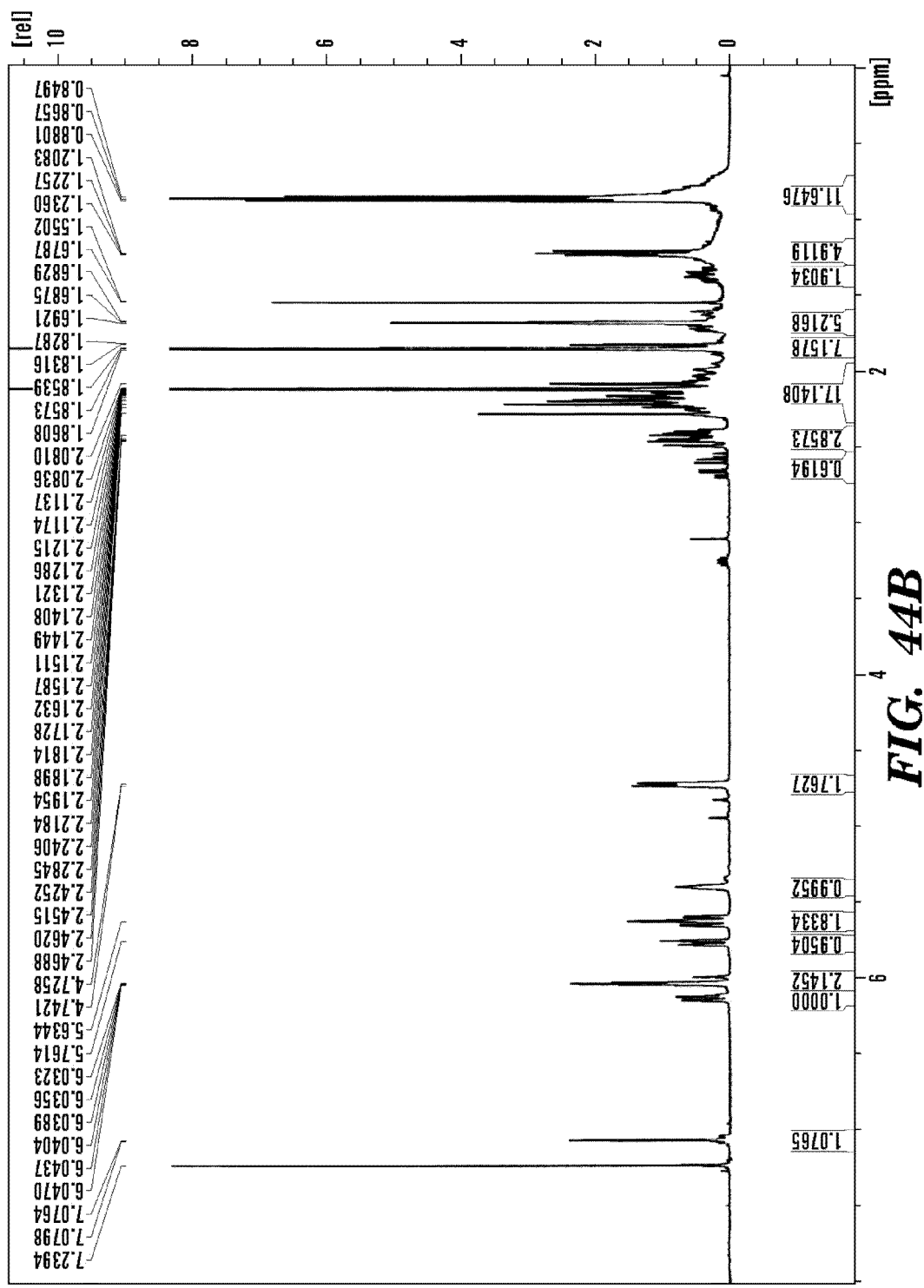
Figure 45:
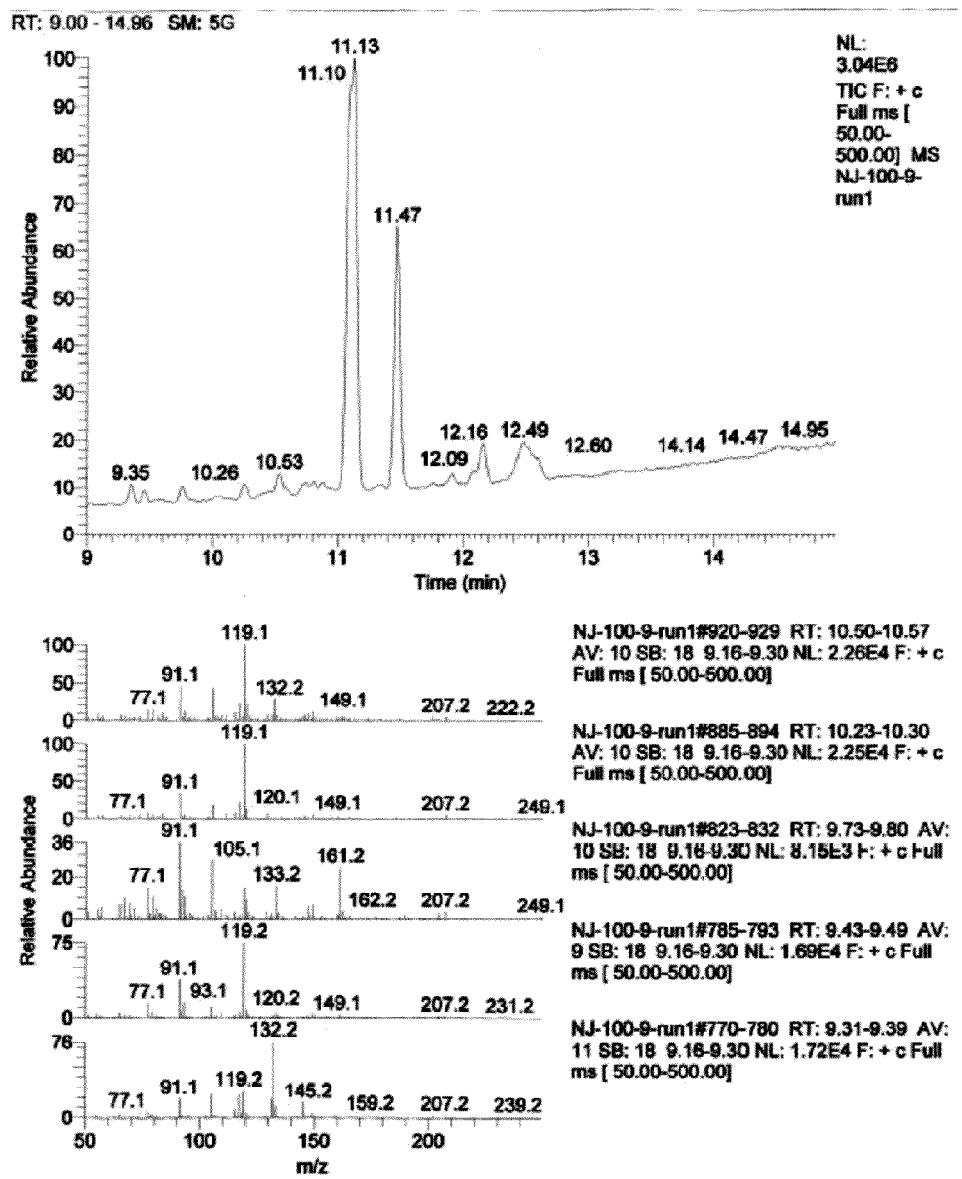
FIGS. 45-48 show GC mass spectra of turmeric oil extract fraction NJ-100-9.
Figure 46:
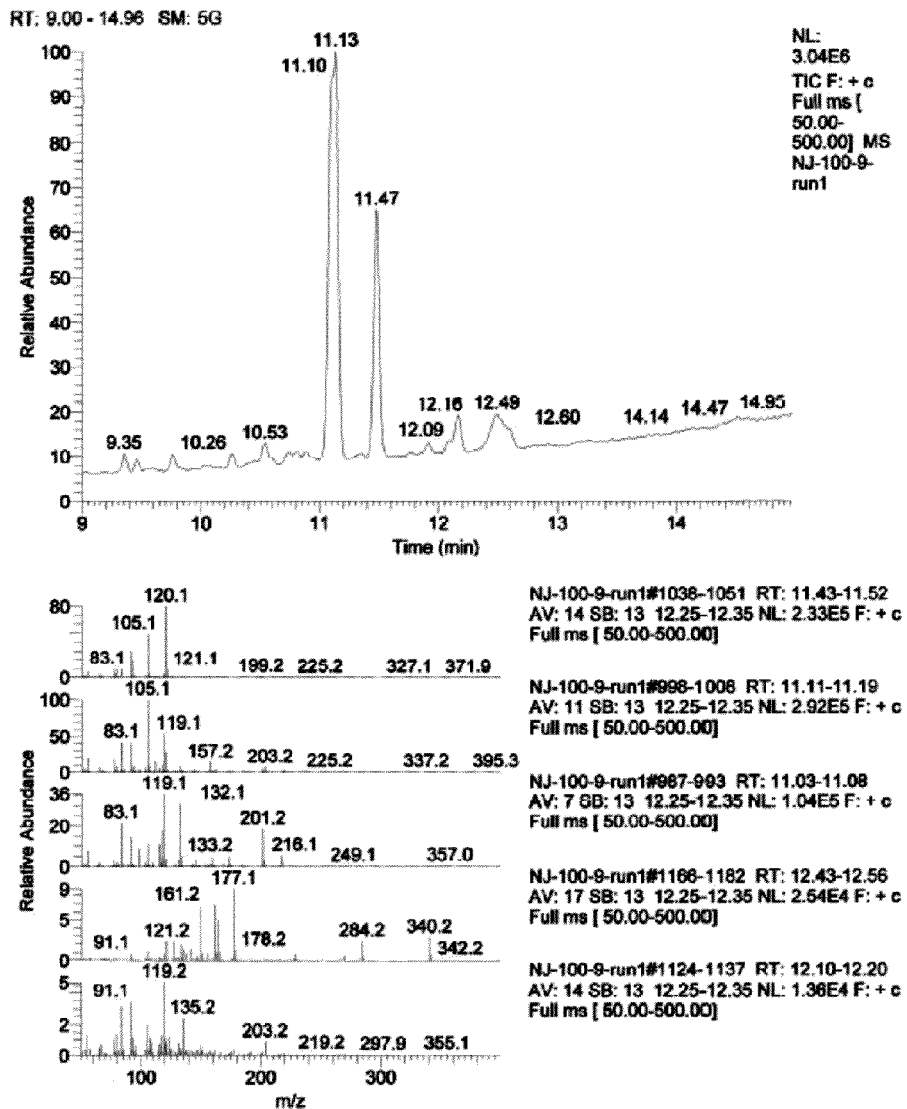
Figure 47:
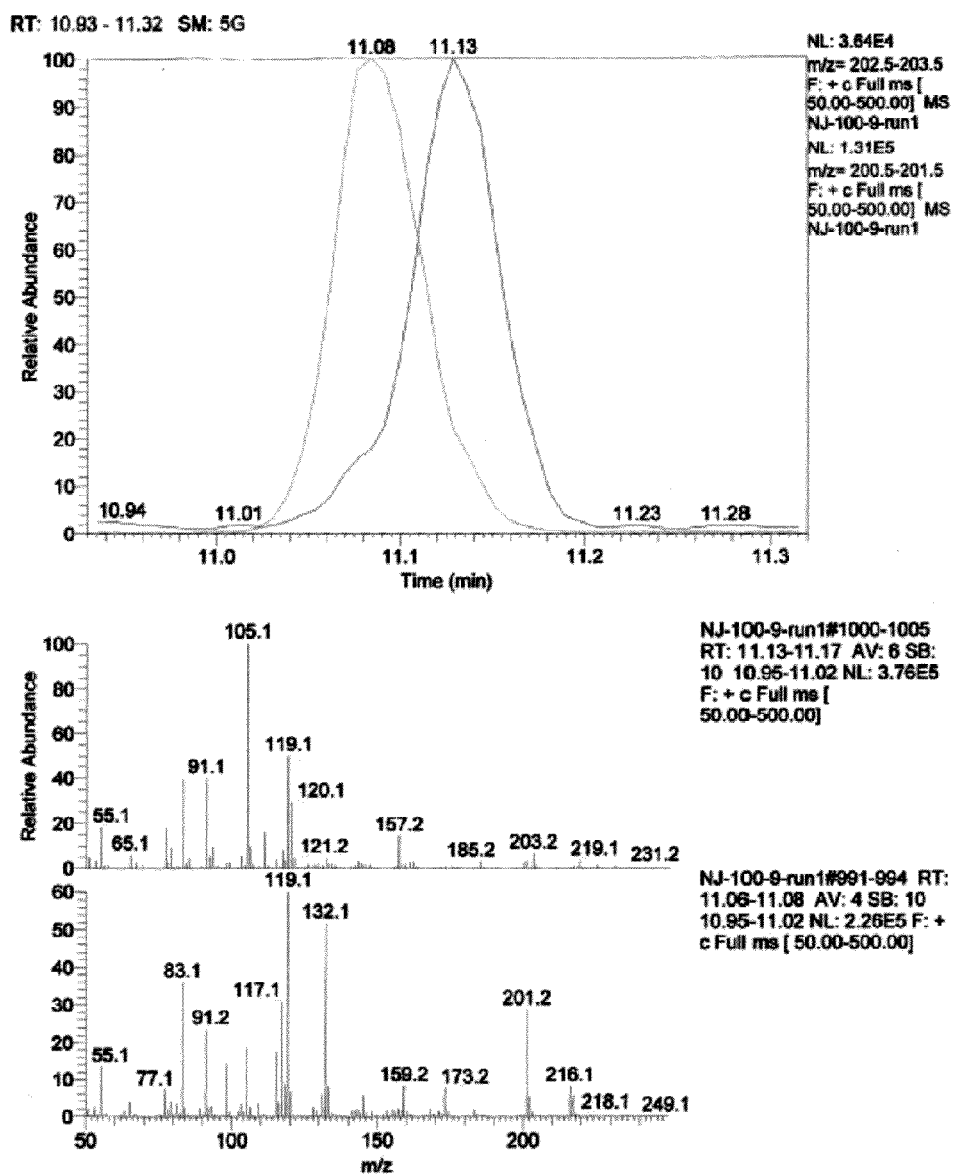
Figure 48:
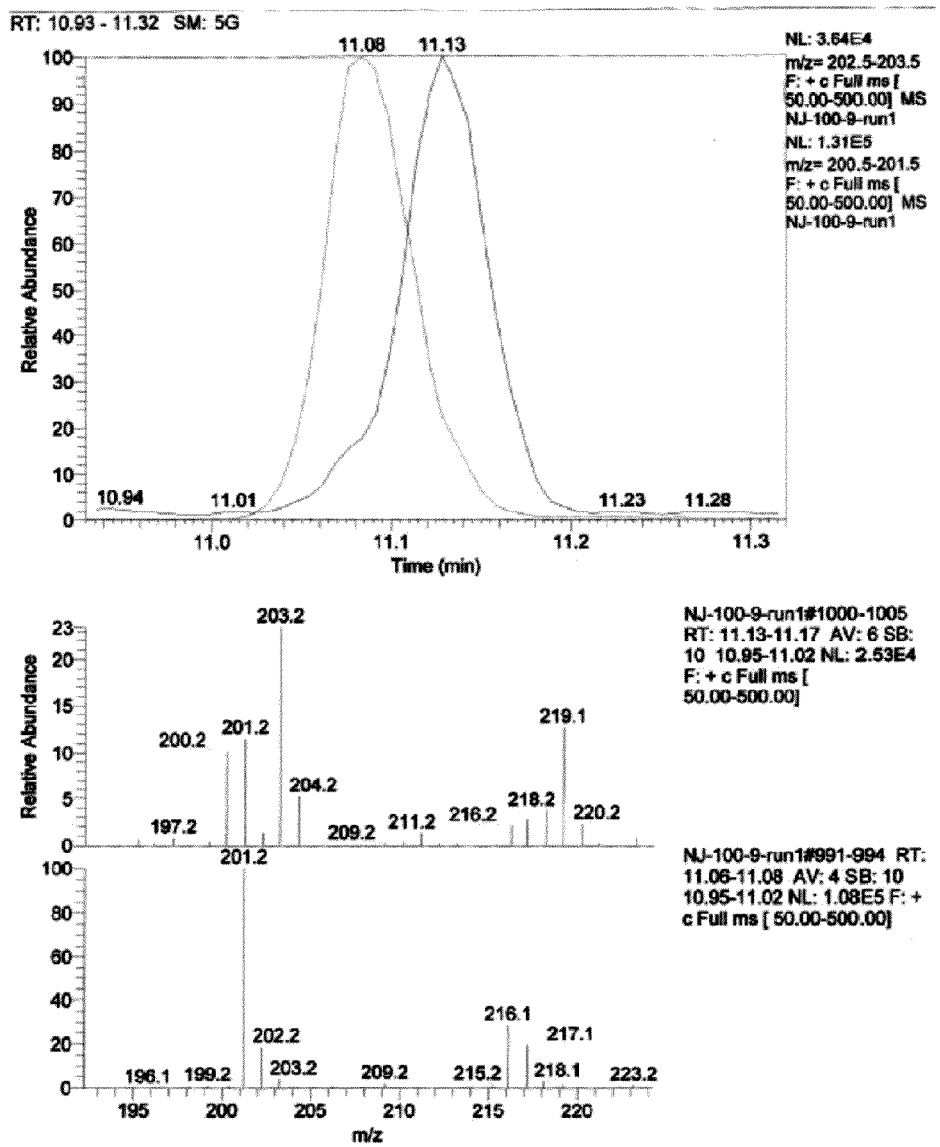

Results of the tail flick assay are shown in Table 21 and FIG. 40. The analgesic activity study showed that the combination of NJ-104-3, fish oil and the distillation fraction of turmeric oil (NJ-100-9) (combined at 50:50 ratio), at 100 mg/kg had strong activity during the initial time periods of 30, 60 and 90 minutes. The drugs, fish oil (NJ-104-1) and turmeric oil fraction (NJ-104-2) by themselves, were considerably less active then the combination (NJ-104-3). Curcumin diglutarate showed strong activity at 90 and 180 minutes. The activities of fish oil (NJ-104-1), turmeric oil (NJ-104-2) and curcumin diglutarate (NJ-104-5) were stronger than that of aspirin at 90 minutes at this dose.

TABLE 21

Tail flick latency time (seconds) in various groups

| Groups | min | 30 min | 60 min | 90 min | 120 min | 180 min |
|---|---|---|---|---|---|---|
| 1 | 2.4625 | 3.475 | 3.3625 | 3.325 | 2.4625 | 3.475 |
| 2 | 3.5375 | 3.875 | 3.8375 | 4.1375 | 3.5375 | 3.875 |
| 3 | 3.3875 | 3.5625 | 3.6 | 3.775 | 3.3875 | 3.5625 |
| 4 | 3.075 | 3.6 | 3.725 | 3.9875 | 3.075 | 3.6 |
| 5 | 3.4375 | 3.675 | 3.6125 | 3.6375 | 3.4375 | 3.675 |
| 6 | 3.05 | 3.5625 | 3.6125 | 3.7375 | 3.05 | 3.5625 |

The anti-inflammatory activity was strong for the turmeric oil fraction and for curcumin acetate whereas the combination of turmeric oil and fish oil showed strong analgesic activity. Curcumin diglutarate also seem to have strong analgesic activity under the test conditions of the present study.

Example 10

Extraction and Purification of Turmeric Oil (II)

Turmeric powder 500 g was extracted with 3 L hexane to get 27.8 g of crude turmeric oil. This was distilled under high vacuum and three fractions were obtained as follow: (i) BR-103-1<108° C., 0.156 g; (ii) BR-103-2, 108-122° C., 14.48 g; and (iii) BR-103-3 3.91 g.

Fraction BR-103-2 was purified on two flash columns connected to each other, with the first column containing 120 g of silica gel and the second column containing 200 g of silica gel. Eluted with hexane followed by 0.5% to 20% ethyl acetate, hexane as step gradients collecting 50 mL fractions as shown in Table 22.

TABLE 22

Fractions obtained in purification of turmeric oil extraction

| Fraction # | Amount (g) | Fraction label |
|---|---|---|
| 1 | 1.33 | BR-110-1 |
| 2 | 0.124 | BR-110-2 |
| 3 | 0.071 | BR-110-3 |
| 4 | 4.71 | BR-110-4 |
| 5 | 0.594 | BR-110-5 |
| 6 | 4.32 | BR-110-6 |
| 7 | 3.62 | BR-110-7 |
| 8 | 0.507 | BR-110-8 |
| 9 | 0.507 | BR-110-9 |

A mixture (8.23 g) of turmeric oil distillation fraction BR-103-3 (122-143° C./vac.) and column purified fraction BR-110-6 were combined and distilled to get BR-132-4 (6.59 g).

A portion of BR-132-4 (300 mg) was purified by column chromatography on silica gel (20 g), obtaining two TLC pure fractions, NJ-106-1 (16 mg) and NJ-106-2 (10 mg) for NMR spectra and the remaining as mixture.

Example 11

Extraction and Purification of Turmeric Oil (III)

Turmeric powder 500 g was extracted with 3 L hexane to get 27.8 g of crude turmeric oil. This was distilled under high vacuum and three fractions were obtained as follow: (i) BR-103-1<108° C., 0.156 g; (ii) BR-103-2, 108-122° C., 14.48 g; and (iii) BR-103-3 3.91 g.

Fraction BR-103-2 was purified on two flash columns connected to each other, with the first column containing 120 g of silica gel and the second column containing 200 g of silica gel. Eluted with hexane followed by 0.5% to 20% ethyl acetate, hexane as step gradients collecting 50 mL fractions as shown in Table 22.

Example 12

Synthesis of Curcumin Ether Derivatives

The curcumin ether derivatives were synthesized by the method described in Majhi, et al., "Binding of curcumin and its long chain derivatives to the activator binding domain of novel protein kinase C", *Bioorganic & Medicinal chemistry*, 2010, 18: 1591-1598.

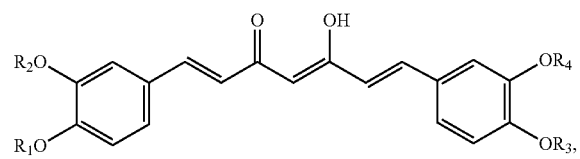

wherein $R_2=R_4=CH_3$ and $R_1=R_3$=alkyl or $R_1=H$, $R_3$=alkyl.

Specifically, a mixture of curcumin (2.21 g), bromooctadecance (1.83 mL), potassium carbonate (0.828 g) and acetone (60 mL) was refluxed overnight. The mixture was cooled, filtered and concentrated. The residue was washed with 100 mL of 10% ethyl acetate and hexane for 1 hour, filtered and concentrated to get 2.0 grams, the residue was purified over silica gel (40 grams) column, eluted with ethyl acetate (0 to 10%), hexane to get two fractions: (i) BR-114-1, 0.14 grams TLC $R_f$=0.78 (Ethyl acetate, hexane 1:1), NMR consistent with structure; and (ii) BR-114-2, 0.50 grams TLC $R_f$ 0.44 (Ethyl acetate, hexane 1:1), NMR consistent with structure.

Example 13

Extraction of Turmeric Oil

Hexane extract (27.7 g) obtained from 500 g of turmeric powder in 3 liters of hexane was distilled to obtain a distillate at 90°-405° C., 0.50 g (NJ-100-3) and a distillate at 105°-118° C., 15.5 g (NJ-100-9).

Example 14

Evaluation of Anti-Cancer Activity of Less-Purified Turmeric Oil Extract Fractions The following compounds and combinations were used in this experiment: a mix of 10 mg of NJ-100-3 and mg of Paclitaxel (NJ-102-2), a mix of 10 mg of NJ-100-9 and mg Paclitaxel (NJ-102-3), and Pacitaxel (NJ-102-4).

Determination of $EC_{50}$ of Testing Compounds:

Cytotoxicity of the compounds on three different cancer cell lines and one normal cell line was tested. Four human cell lines including both cancer cell lines (SK-BR-3, PANC-1, PC3) and normal cell line (WI38) were initially employed. The cells (20,000 cells/well) were plated onto a 96-well plate for 24 hours before treatment. The compounds were diluted in the medium and added to the cells at different concentrations for additional 48 hours from 0.04 ng/ml to 400 ng/ml. MTT assay was then performed. $EC_{50}$ values are summarized in Table 23.

TABLE 23

$EC_{50}$ values of compounds for various cell lines

| Cell line | NJ-102-2 | NJ-102-3 | NJ-102-4 |
|---|---|---|---|
| PANC-1 | 7.466 ng/ml | 22.53 ng/ml | 32.79 ng/ml |
| PC3 | 16.13 ng/ml | 28.11 ng/ml | 8.511 ng/ml |
| SK-BR-3 | 28.08 ng/ml | 26.92 ng/ml | 36.07 ng/ml |
| WI38 | 13.91 ng/ml | 16.24 ng/ml | 37.91 ng/ml |

Determination of $GI_{50}$ (50% Inhibition of Cell Growth):

Since the compounds displayed inhibitory effect on cell proliferation, a $GI_{50}$ experiment was performed. The cells were plated onto a 96 well plate and treated with different concentrations of the compounds from 0.04 ng/ml to 400 ng/ml for 72 hours followed by MTT assay. $GI_{50}$ values are summarized in Table 24.

TABLE 24

$GI_{50}$ values of compounds for various cell lines

| Cell line | NJ-102-2 | NJ-102-3 | NJ-102-4 |
|---|---|---|---|
| PANC-1 | 2.69 ng/ml | 2.599 ng/ml | 5.456 ng/ml |
| PC3 | 5.01 ng/ml | 1.55 ng/ml | 0.05 ng/ml |
| SK-BR-3 | 2.72 ng/ml | 0.41 ng/ml | 0.78 ng/ml |
| WI38 | 15.74 ng/ml | 14.68 ng/ml | 5.60 ng/ml |

Example 15

Characterization of Turmeric Oil Components

HPLC:
Hewlet Packard, model HP 1090 series II, column X-terra C-18 5 mm, 4.6×150 mm, Solvent A: acetonitrile/water 85-15, Solvent B: acetonitrile, methanol, water, phosphoric acid, 40-10-49-1.

NMR:
Brucker (400 MHz) (solvent $CDCl_3$ unless specified otherwise).

GC MS results were obtained on a Waters GCT Premier coupled with an Agilent 6890N GC. GC separation from a splitless injection was performed on a J&W Scientific DB-5MS column, 30 m×0.25 mm ID×25 micron film thickness, with He carrier gas at 1 ml/min. The temperature gradient was as follows: 50 C for 2 min, 25 C/min to 250 C, and 250 C for 4 min. Ions were generated via electron ionization, and mass spectra were recorded at a resolving power of 6,000.

LCMS:
LCMS results were acquired with a Bruker MicrOTOF-QII quadrupole time-of-flight mass spectrometer coupled with a Dionex Ultimate 3000 RSLC ultrahigh pressure LC. LC separation was performed on a Dionex Acclaim RSLC 120 C18 2.1 mm ID×100 mm column with 2.2 um particles and 120 angstrom pore size. The binary gradient consisted of solvent A (water with 0.1% formic acid) and solvent B (acetonitrile with 0.1% formic acid) at 0.5 ml/min initially at 90:10 (A:B) for 2 min ramped to 0:100 (A:B) at 12 min then held until 14 min. Ions were generated via electrospray ionization, and mass spectra were recorded at a resolving power of 10,000.

Figure 49:
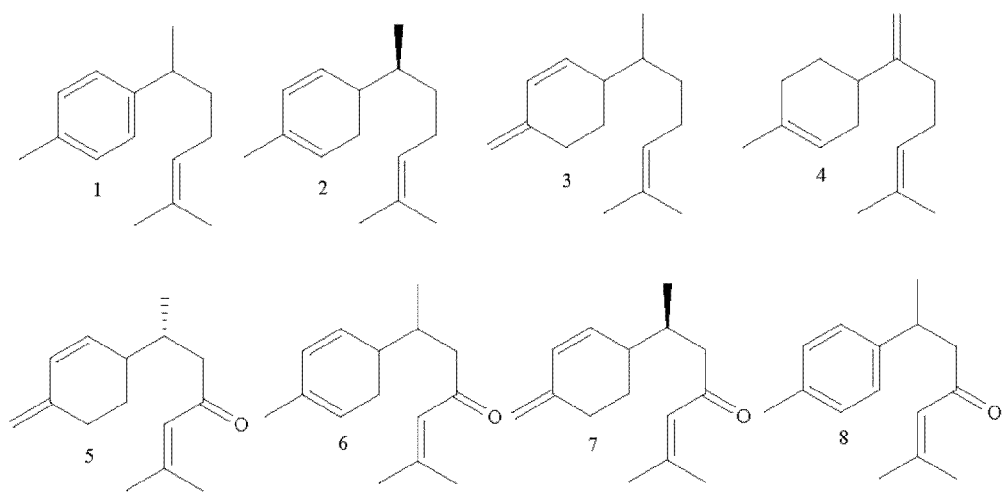
FIG. 49 shows structures of some exemplary sesquiterpene component s of turmeric oil fractions. Show are ar-curcumene (1), 7-epizingiberene (2), β-sesquiphellandrene (3), β-bisabolene (4), curlone (5), α-turmerone (6), β-turmerone (7), and ar-turmerone (8).

Separation and Characterization of Turmeric Oil Fractions:
Turmeric powder (500 g) was extracted with hexane to get 27.80 g of the crude extract. This was distilled under high vacuum to obtain a fraction (14.48 g) that distilled at 108-122° C. This was further purified with silica gel column chromatography using step gradient of hexane (100 to 95%) and ethyl acetate (0 to 5%). This gave several column fractions and the following were selected for the current study, CF-1, 1.33 g, CF-2, 0.071 g, CF-3, 4.71 g, and CF-4, 0.594 g. CF-1 (0.50 g) was further purified by a silica gel column eluting with hexane to give 0.25 g of CF-5. HPLC and mass spectral studies for these compounds indicated that they were sesquiterpenes (FIG. 49).

CF-1: HPLC (solvent A), RT (area), 5.67 min (8%), 7.88 min (48%) and 11.28 min (43%). GCMS, RT (m/z) 9.35 min (202.2) and 9.75 min (204.2). NMR (see structural identification in CF-5).

CF-2: HPLC (solvent A), RT 3.00 min (63%), 4.20 min (11.8%), 5.02 min (19.37%), GCMS, RT at 7.54 and 9.03 minutes and mass peak at 218.1664 corresponding to molecular formula, $C_{15}H_{22}O$. NMR, δ, 0.83-0.95 (m, 4H), 1.14-1.23 (m, 4H), 1.53-2.33 (m, 26H), 2.72 (q, 1H), 3.80 (bs, 0.65H), 5.20 (bs, 0.58H), 5.38 (bs, 1H), 5.98-6.1 (m, 1.8H) (unidentified mixture of turmerone isomers).

CF-3: HPLC (solvent A), RT, (2.87 min, 48.38%), 4.08 min (48.46%), GCMS, RT 11.08 min (m/z 216.1) 11.46 (m/z 218.2). The GC-mass spectral fragmentation peak confirms the structures, β-turmerone/curlone, α-turmerone, ar-turmerone (see supplementary information). NMR δ 0.75 (m), 0.0.88 (d, J=6.5 Hz), 0.89 (d, J=6.5 Hz), 0.95 (m), 1.07 (m), 1.24 (d, J=7 Hz), 1.38 (m), 1.6 (s=water), 1.64 (bs), 1.72 (q, J=1.8 Hz), 1.75 (m), 1.86 (d, J=1.3 Hz), 1.88 (d, J=1.5 Hz), 1.89 (d, J=1.5 Hz), 1.97-2.35 (m), 2.14 (d, J=1.1 Hz), 2.15 (d, J=1.1 Hz), 2.4-2.5 (m), 2.51 (dd, J=14.6, 4 Hz), 2.61 (dd, J=15.7, 6.0 Hz), 2.68 (dd, J=15.7, 6.0 Hz), 3.1 (m), 3.14 (q, J=1.2 Hz), 3.28 (m), 4.75 (bs), 4.77 (bs), 4.82 (br m), 4.86 (q, J=1.2 Hz), 4.95 (br m), 5.38 (br m), 5.43 (bs), 5.64 (dd, J=10, 3.2 Hz), 5.69 (br m), 5.8 (ddd, J=9.8, 2.4, 1.5 Hz), 6.02 (t, J=1.4 Hz), 6.06 (m), 6.14 (t, J=1.3 Hz), 6.17 (dd, J=10, 2.5 Hz), 7.1 (br d, J=1.7 Hz). CF-2 was analyzed by $^1$H NMR and determined to be a mixture of β-turmerone/curlone (53%), α-turmerone (36%), ar-turmerone (4%), and an unidentified components (7%) by comparison with published NMR data. Percentages were calculated from relative integration values of the resolved peaks of each as a function of the whole sample including the unidentified component(s).

CF-4: HPLC (solvent B), (RT 1.96 min, 84%), 3.26 min (15%). GCMS, RT 8.45 min, m/z 216.1493, corresponds to molecular formula, $C_{15}H_{20}O$. NMR δ 1.24 (3H, d, J=7 Hz), 1.6 (s=water), 1.85 (3H, d, J=1.3 Hz), 2.11 (3H, s), 2.3 (3H, s), 2.61 (1H, dd, J=15.7, 8.3 Hz), 2.68 (1H, dd, J=15.6, 6.1 Hz), 3.28 (1H, m), 6.02 (1H, t, J=1.4 Hz), 7.08 (4H, br d, J=1.7 Hz), (corresponds to ar-turmerone).

CF-5: HPLC, RT 5.64 min (3.88%), 7.93 min (49.46%), 11.27 min (46.62%), GCMS, RT 10.15 min (m/z 202, 145, 132, 119, 105, 91), RT 10.31 min (m/z 204, 161, 119, 109, 93), RT 10.43 min (m/z 204, 161, 133, 120, 109, 93). The GC-MS and mass spectral fragmentation peaks confirmed the structures (data not shown). NMR δ 0.86 (d, J=6.9 Hz), 0.88 (d, J=6.8 Hz), 1.19 (m), 1.23 (d, J=6.9 Hz), 1.41 (m), 1.5-1.7 (br m), 1.62 (s), 1.68 (s), 1.7 (s), 1.73 (m), 1.83-2.18 (br m), 2.23 (m), 2.29 (m), 2.44 (dt, J=14.9, 4.3 Hz), 2.67 (q, J=7.2 Hz), 4.75 (br s), 5.1 (m), 5.12 (br t, J=7.1 Hz), 5.46 (br s), 5.65 (dd, J=9.9, 3.1 Hz), 5.69 (d, J=9.7 Hz), 5.78 (dt, J=9.6, 2.0 Hz), 6.16 (dd, J=10, 2.7 Hz), 7.09 (m). CF-5 was analyzed by $^1$H and 1D TOCSY NMR and determined to be a mixture of β-sesquiphellandrene (50.3%), 7-epi-zingiberene (30.7%) and ar-curcumene (19%) by comparison with published NMR data (Breedan, D. C. & Coates, R. M. Tetrahedron, 1994, 50, 11123; McBrien et al., J. Chem Ecol., 2002, 28, 1797; and Takigawa et al., Appl. Environ. Microbio. 1993, 58, 1336). Percentages were calculated from relative integration values of the resolved peaks of each of the 3 major components. Comparison of 1H NMR shifts for various components of turmeric oil fractions are shown in Tables 25-28.

TABLE 25

Comparison of 1H NMR Shifts for α-turmerone and β-turmerone/curlone.

| $^1$β-turmerone/curlone (δ) | $^2$β-turmerone (δ) | $^1$α-turmerone (δ) | $^2$α-turmerone (δ) |
| --- | --- | --- | --- |
| 6.17 (1H, dd, J = 10, 2.5 Hz) | 6.16 (1H, dd, J = 10, 2.3 Hz) | 6.06 (1H, t, J = 1.3 Hz) | 6.06 (1H, t, J = 1.3 Hz) |
| 6.06 (1H, m) | 6.07 (1H, dd, J = 1.2, 1.0 Hz) | 5.78 (1H, ddd, J = 9.8, 2.4, 1.5 Hz) | 5.8 (1H, ddd, J = 9.6, 1.9, 1.7 Hz) |
| 5.68 (1H, m) | 5.67 (1H, brd, J = 10.7 Hz) | 5.64 (1H, dd, J = 10, 3.2 Hz) | 5.64 (1H, dd, J = 9.6, 3.1 Hz) |
| 4.77 (1H, br s) | 4.77 (1H, br s) | 5.43 (1H, br s) | 5.43 (1H, br s) |
| 4.75 (1H, br s) | 4.75 (1H, br s) | 2.5 (1H, dd, J = 14.6, 4 Hz) | 2.5 (1H, dd, J = 14.5, 3.9 Hz) |
| 2.5-2.4 (2H, m) | 2.5-2.4 (2H, m) | 2.3-2.0 (5H, m) | 2.3-2.0 (5H, m) |
| 2.35-2.15 (3H, m) | 2.35-2.15 (3H, m) | 2.14 (3H, d, 1.1 Hz) | 2.14 (3H, d, J = 1.3 Hz) |

TABLE 25-continued

Comparison of 1H NMR Shifts for α-turmerone and β-turmerone/curlone.

| $^1$β-turmerone/curlone (δ) | $^2$β-turmerone (δ) | $^1$α-turmerone (δ) | $^2$α-turmerone (δ) |
|---|---|---|---|
| 2.14 (3H, d, J = 1.1 Hz) | 2.14 (3H, d, J = 1.0 Hz) | 1.88 (3H, d, J = 1.5 Hz) | 1.88 (3H, d, J = 1.3 Hz) |
| 2.04 (1H, m) | 2.03 (1H, m) | 1.71 (3H, d, J = 1.7 Hz) | 1.71 (3H, d, J = 1.7 Hz) |
| 1.88 (3H, d, J = 1.5 Hz) | 1.88 (3H, d, J = 1.2 Hz) | 0.88 (3H, d, J = 6.5 Hz) | 0.88 (3H, d, J = 6.5 Hz) |
| 1.64 (1H, m) | 1.64 (1H, m) | | |
| 1.38 (1H, m) | 1.38 (1H, m) | | |
| 0.89 (3H, d, J = 6.6 Hz) | 0.88 (3H, d, J = 6.3 Hz) | | |

$^1$NMR shifts are referenced to CDCl3 (δ 7.27) at 300K.
$^2$NMR shifts from (*Biol. Pharm. Bull.* 26(8) 1135-1143 (2003).

TABLE 26

Comparison of $^1$H NMR Shifts for ar-turmerone

| $^1$ar-turmerone (δ) | $^2$ar-turmerone (δ) | Unidentified Resonances (δ) |
|---|---|---|
| 7.1 (4H, br d, J = 1.7 Hz) | 7.1 (4H, br d, J = 1.7 Hz) | 6.14 (t, J = 1.3 Hz) |
| 6.02 (1H, br t, J = 1.4 Hz) | 6.02 (1H, t, J = 1.2 Hz) | 5.38 (br) |
| 3.28 (1H, br m) | 3.28 (1H, ddd, J = 8.4, 6.7, 6.0 Hz) | 4.98 (t, J = 1.2 Hz) |
| 2.68 (1H, dd, J = 15.6, 6.1 Hz) | 2.68 (1H, dd, J = 15.7, 6.0 Hz) | 4.95 (br m) |
| 2.61 (1H, dd, 15.7, 8.3 Hz) | 2.6 (1H, dd, J = 15.7, 8.4 Hz) | 4.86 (q, J = 1.2 Hz) |
| 2.3 (3H, s) | 2.3 (3H, s) | 4.82 (br m) |
| 2.11 (3H, d, J = 1.3 Hz) | 2.10 (3H, d, J = 1.2 Hz) | 3.14 (d, 1.2 Hz) |
| 1.85 (3H, d, J = 1.3 Hz) | 1.85 (3H, d, J = 1.2 Hz) | 3.1 (m) |
| 1.24 (3H, d, J = 7 Hz) | 1.24 (3H, d, J = 6.8 Hz) | 1.98 (m) |
| | | 1.92 (m) |
| | | 1.75 (m) |
| | | 1.26 (br) |
| | | 1.07 (m) |
| | | 0.95 (m) |
| | | 0.75 (m) |

$^1$NMR shifts are referenced to CDCl3 (δ 7.27) at 300K.
$^2$NMR shifts from (*Biol. Pharm. Bull.* 26(8) 1135-1143 (2003).

TABLE 27

Comparison of $^1$H NMR Shifts for β-sesquiphellandrene and zingiberene.

| $^1$β-sesquiphellandrene (δ) | $^2$β-sesquiphellandrene (δ) | $^1$7-epi-zingiberene (δ) | $^3$7-epi-zingiberene (δ) |
|---|---|---|---|
| 6.16 (1H, dd, J = 10, 2.7 Hz) | 6.16 (1H, dd, J = 9.9, 2.5 Hz) | 5.78 (1H, dt, J = 9.6, 2.0 Hz) | 5.78 (1H, dt, J = 9.8, 2.0 Hz) |
| 5.69 (1H, d, 9.7 Hz) | 5.70 (d, 1H, J D 9.7 Hz) | 5.65 (1H, dd, J = 9.9, 3.1 Hz) | 5.64 (1H, dd, J = 9.8, 2.9 Hz) |
| 5.12 (1H, m) | 5.12 (1H, m) | 5.46 (1H, br s) | 5.45 (1H, br s) |
| 4.75 (2H, br s) | 4.75 (2H, br s) | 5.12 (1H, br t, J = 7.1 Hz) | 5.11 (1H, br t, J = 7.6 Hz) |
| 2.44 (1H, dt, J = 14.9, 4.3 Hz) | 2.44 (1H, dt, J = 16.5, 4.6 Hz) | 2.27 (1H, br m) | 2.28 (1H, m) |
| 2.29 (1H, m) | 2.3 (1H, m) | 2.04 (2H, m) | 2.04 (2H, m) |
| 2.23 (1H, m) | 2.23 (1H, m) | 2.01 (2H, m) | 2.03 (2H, m) |
| 2.01 (2H, m) | 2.0 (2H, m) | 1.7 (3H, br s) | 1.72 (3H, d, J = 1.7 Hz) |
| 1.73 (1H, m) | 1.74 (1H, m) | 1.68 (3H, br s) | 1.68 (3H, s) |
| 1.70 (3H, s) | 1.70 (3H, s) | 1.62 (3H, s) | 1.61 (3H, s) |
| 1.62 (3H, s) | 1.62 (3H, s) | 1.19 (1H, m) | 1.18 (1H, m) |
| 1.56 (1H, m) | 1.57 (1H, m) | 0.88 (3H, d, J = 6.8 Hz) | 0.87 (3H, d, J = 6.8 Hz) |
| 1.41 (2H, m) | 1.40 (2H, m) | | |
| 1.19 (1H, m) | 1.22 (1H, m) | | |
| 0.86 (3H, d, J = 6.9 Hz) | 0.86 (3H, d, J = 8 Hz) | | |

$^1$NMR shifts are referenced to CDCl3 (δ 7.24) at 300K.
$^2$NMR shifts from *Biol. Pharm. Bull.* 26(8) 1135-1143 (2003).
$^3$NMR shifts from *Tetrahedron* Vol. 50, No. 38, pp. 11123-11132. 1994.

TABLE 28

Comparison of 1H NMR Shifts for α-curcumene.

| [1]α-curcumene (δ) | [2]α-curcumene (δ) |
|---|---|
| 7.09 (4H, br d, J = 4 Hz) | 7.05 (4H, br s) |
| 5.1 (1H, br) | 5.09 (1H, t, J = 7.7 Hz) |
| 2.67 (1H, q, J = 7.2 Hz) | 2.63 (1H, m) |
| 1.89 (2H, br m) | 1.9-1.8 (2H, m) |
| 1.7-1.5 (2H, m) | 1.7-1.5 (2H, m) |
| 1.68 (3H, s) | 1.66 (3H, s) |
| 1.54 (3H, s) | 1.51 (3H, s) |
| 1.23 (3H, d, J = 6.9 Hz) | 1.21 (3H, d, J = 6.9 Hz) |

All patents and other publications identified in the specification are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A curcumin derivative having a structure of formula (I): wherein:
   $R^1$ and $R^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)$R^3$, —C(O)O$R^3$, or —C(O)N$R^3R^3$, provided that at least one of $R^1$ and $R^2$ is a linking group conjugated with a glyceryl lipid and wherein the lipid is a fatty acid or a fatty alkyl group; and
   $R^3$ is independently for each occurrence H, optionally substituted alkyl, optionally substituted alkenyl, optionally substituted alkynyl, optionally substituted cyclyl, optionally substituted heterocyclyl, optionally substituted aryl, or optionally substituted heteroaryl.

2. The curcumin derivative of claim 1, wherein one of $R^1$ and $R^2$ of Formula (I) is selected from the group consisting of acetyl, myristoleoyl, palmitoleoyl, sapienoyl, oleoyl, linoleoyl, α-linoleoyl, α-linolenoyl, γ-linolenoyl, arcchidionoyl, eicosapentaenoyl, erucoyl, docosahexaenoyl, lauroyl, myrsitoyl, palmitoyl, stearoyl, arachidoyl, behenoyl, lignoceroyl, certoyl and any combinations thereof.

3. The curcumin derivative of claim 1, wherein one of $R^1$ and $R^2$ of Formula (I) is —C(O)$R^3$ and $R^3$ is an optionally substituted aryl.

4. The curcumin derivative of claim 1, wherein the curcumin derivative is selected from the group consisting of curcumin-glutarate-lipid, curcumin-diglutarate-mono-lipid, and curcumin-diglutrate-dilipid.

5. A composition comprising a curcumin derivative and a compound selected from the group consisting of an anti-cancer compound, an anti-inflammatory agent, fish oil, fish oil extract, aspirin, a salicylic acid conjugate, and any combinations thereof, wherein the salicylic acid conjugate is of formula (II):
   wherein $R^8$ is a carbohydrate; $R^9$ is H, optionally substituted alkyl, optionally substituted alkenyl, optionally substituted alkynyl, or optionally substituted acyl; or analogs, derivatives, isomers, prodrugs, or pharmaceutically acceptable salts thereof, and wherein the curcumin derivative is a curcumin derivative of claim 1.

6. The composition of claim 5, wherein $R^8$ is selected from the group consisting of glucose, glyceraldehydes, erythrose, threose, ribulose, xylulose, ribose, arabinose, deoxyribose, xylose, lyxose, psicose, fructose, sorbose, tagatose, allose, altrose, mannose, gulose, idose, galactose, talose, fucose, fuculose, rhamnose, sedoheptulose, octose, and nonose (Neuraminic acid).

7. The composition of claim 5, wherein the composition comprises a curcumin derivative and aspirin; a curcumin derivative and a salicylic acid conjugate; a curcumin derivative and curcumin.

8. The composition of claim 5, wherein the anti-cancer agent is selected from the group consisting of composition consisting of paclitaxel (taxol); docetaxel; 2'-(glucose-succinoyl)paclitaxel; 2'-(glucose-glutamyl)paclitaxel; 2'-(glucosamide-GABA-succinoyl)paclitaxel; 2'-(glucoseamide-succinoyl)paclitaxel; 2'-(glucoseamide-glutamyl)paclitaxel; 7-(GABA-succinoyl)paclitaxel; 7-(glucose-GABA-succinoyl)paclitaxel; 7-(glucose-succinoyl)paclitaxel; 7-(glucose-glutamyl)paclitaxel; 7-(glucosamide-GABA-succinoyl)paclitaxel; 7-(glucoseamide-succinoyl)paclitaxel; 7-(glucoseamide-glutamyl)paclitaxel; and any combinations thereof.

9. A method of treating inflammation or an inflammatory disease or condition in a subject, the method comprising: administering a therapeutically effective amount of:
   (A) a curcumin derivative, or
   (B) a composition comprising: (a) a curcumin derivative, and (b) a compound selected from the group consisting of an anti-cancer compound, an anti-inflammatory agent, fish oil, fish oil extract, aspirin, a salicylic acid conjugate, a curcumin ether derivative and any combinations thereof, to a subject in need thereof, wherein the salicylic acid conjugate is of formula (II):
   wherein $R^8$ is a carbohydrate; $R^9$ is H, optionally substituted alkyl, optionally substituted alkenyl, optionally substituted alkynyl, or optionally substituted acyl; or analogs, derivatives, isomers, prodrugs, or pharmaceutically acceptable salts thereof, and wherein the curcumin derivative is a curcumin derivative of claim 1.

10. A method of treating cancer or a metastasis in a subject, the method comprising: administering a therapeutically effective amount of:
    (A) a curcumin derivative, or
    (B) a composition comprising: (a) a curcumin derivative, and (b) a compound selected from the group consisting of an anti-cancer compound, an anti-inflammatory agent, fish oil, fish oil extract, aspirin, a salicylic acid conjugate, a curcumin ether derivative and any combinations thereof, to a subject in need thereof, wherein the salicylic acid conjugate is of formula (II):
    wherein $R^8$ is a carbohydrate; $R^9$ is H, optionally substituted alkyl, optionally substituted alkenyl, optionally substituted alkynyl, or optionally substituted acyl; or analogs, derivatives, isomers, prodrugs, or pharmaceutically acceptable salts thereof, and wherein the curcumin derivative is a curcumin derivative of claim 1.

11. The composition of claim 10, wherein the composition comprises a curcumin derivative and an anti-cancer agent, wherein the anti-cancer agent is selected from the group consisting of paclitaxel; docetaxel; 2'-(glucose-succinoyl)paclitaxel; 2'-(glucose-glutamyl)paclitaxel; 2'-(glucosamide-GABA-succinoyl)paclitaxel; 2'-(glucoseamide-succinoyl) paclitaxel; 2'-(glucoseamide-glutamyl)paclitaxel; 7-(GABA-succinoyl)paclitaxel; 7-(glucose-GABA-succinoyl)

paclitaxel; 7-(glucose-succinoyl)paclitaxel; 7-(glucose-glutamyl)paclitaxel; 7-(glucosamide-GABA-succinoyl)paclitaxel; 7-(glucoseamide-succinoyl)paclitaxel; 7-(glucoseamide-glutamyl)paclitaxel; and any combinations thereof.

12. The curcumin derivative of claim 1, wherein the fatty acid is a mono or poly unsaturated fatty acid.

13. The curcumin derivative of claim 12, wherein the fatty acid is an omega three fatty acid.

14. A curcumin derivative having a structure of formula (I): wherein:
$R^1$ and $R^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)$R^3$, —C(O)O$R^3$, or —C(O)N$R^3R^3$, provided that at least one of $R^1$ and $R^2$ is a linking group conjugated with a glyceryl lipid and wherein the glyceryl lipid comprises one or two lipids conjugated with glycerol; and
$R^3$ is independently for each occurrence H, optionally substituted alkyl, optionally substituted alkenyl, optionally substituted alkynyl, optionally substituted cyclyl, optionally substituted heterocyclyl, optionally substituted aryl, or optionally substituted heteroaryl.

15. The curcumin derivative of claim 14, wherein the lipid is linked to glycerol with an ester group or an ether group.

16. The curcumin derivative of claim 1, wherein the curcumin derivative is curcumin-diglutarate-distearin monoester.

17. A curcumin derivative having a structure of formula (I): wherein:
$R^1$ and $R^2$ are independently H, optionally substituted alkyl, optionally substituted alkenyl, optionally substituted alkynyl, optionally substituted cyclyl, optionally substituted heterocyclyl, optionally substituted aryl, optionally substituted heteroaryl, a peptide, —C(O)$R^3$, —C(O)O$R^3$, or —C(O)N$R^3R^3$, provided that at least one of $R^1$ and $R^2$ is a linking group conjugated with a glyceryl lipid and wherein the linking group is a succinoyl group, glutaryl group, or ether group; and
$R^3$ is independently for each occurrence H, optionally substituted alkyl, optionally substituted alkenyl, optionally substituted alkynyl, optionally substituted cyclyl, optionally substituted heterocyclyl, optionally substituted aryl, or optionally substituted heteroaryl.

* * * * *

UNITED STATES PATENT AND TRADEMARK OFFICE
CERTIFICATE OF CORRECTION

PATENT NO.         : 9,012,411 B2
APPLICATION NO.    : 13/537814
DATED              : April 21, 2015
INVENTOR(S)        : James N. Jacob It is certified that error appears in the above-identified patent and that said Letters Patent is hereby corrected as shown below:

In the Claims

In Claim 1, column 71, between lines 28 and 29, after "a structure of formula (I):" there should be the following formula:

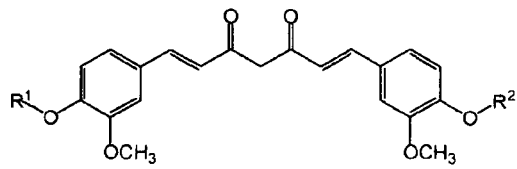

Formula (I)

In Claim 5, column 71, between lines 63 and 64, after "the salicylic acid conjugate is of formula (II):" there should be the following formula:

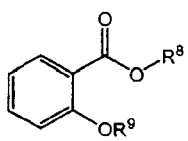

Formula (II)

In Claim 9, column 72, between lines 36 and 37, after "the salicylic acid conjugate is of formula (II):" there should be the following formula:

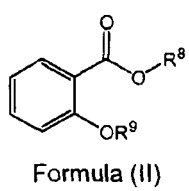

Formula (II)

Signed and Sealed this
First Day of September, 2015

Michelle K. Lee
*Director of the United States Patent and Trademark Office*

In Claim 10, column 72, between lines 53 and 54, after "the salicylic acid conjugate is of formula (II):" there should be the following formula:

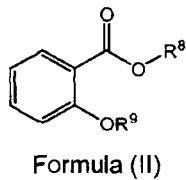

Formula (II)

In Claim 14, column 73, between lines 10 and 11, after "a structure of formula (I):" there should be the following formula:

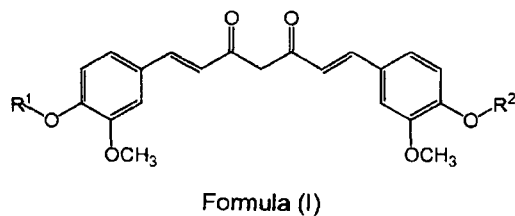

Formula (I)

In Claim 17, column 74, between lines 8 and 9, after "a structure of formula (I):" there should be the following formula:

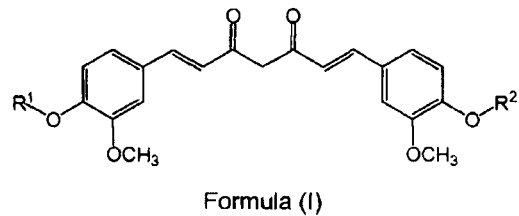

Formula (I)